United States Patent
Abbot et al.

(10) Patent No.: US 9,198,938 B2
(45) Date of Patent: Dec. 1, 2015

(54) AMNION DERIVED ADHERENT CELLS

(71) Applicant: Anthrogenesis Corporation, Warren, NJ (US)

(72) Inventors: Stewart Abbot, Warren, NJ (US); James W. Edinger, Belford, NJ (US); Aleksandar Francki, Annandale, NJ (US); Aleksandr Kaplunovsky, Budd Lake, NJ (US); Vladimir Jankovic, New York, NY (US); Kristen Labazzo, Springfield, NJ (US); Eric Law, East Brunswick, NJ (US); Neerav Padliya, Scotch Plains, NJ (US); Jennifer Paredes, Bloomfield, NJ (US); Jia-Lun Wang, Cherry Hill, NJ (US)

(73) Assignee: ANTRHOGENESIS CORPORATION, Warren, NJ (US)

( * ) Notice: Subject to any disclaimer, the term of this patent is extended or adjusted under 35 U.S.C. 154(b) by 38 days.

(21) Appl. No.: 13/727,217

(22) Filed: Dec. 26, 2012

(65) Prior Publication Data

US 2013/0315875 A1  Nov. 28, 2013

Related U.S. Application Data

(63) Continuation of application No. 12/622,352, filed on Nov. 19, 2009, now Pat. No. 8,367,409.

(60) Provisional application No. 61/116,248, filed on Nov. 19, 2008.

(51) Int. Cl.
*A61K 35/50* (2015.01)
*C12N 5/073* (2010.01)
*A61K 35/12* (2015.01)

(52) U.S. Cl.
CPC ............. *A61K 35/50* (2013.01); *C12N 5/0605* (2013.01); *A61K 35/12* (2013.01)

(58) Field of Classification Search
CPC ..... A61K 35/50; A61K 35/12; C12N 5/06065
See application file for complete search history.

(56) References Cited

U.S. PATENT DOCUMENTS

| | | | |
|---|---|---|---|
| 3,862,002 A | 1/1975 | Sanders | |
| 4,829,000 A | 5/1989 | Kleinman et al. | |
| 5,004,681 A | 4/1991 | Boyse et al. | |
| 5,192,553 A | 3/1993 | Boyse et al. | |
| 5,197,985 A | 3/1993 | Caplan et al. | |
| 5,226,914 A | 7/1993 | Caplan et al. | |
| 5,272,071 A | 12/1993 | Chappel | |
| 5,372,581 A | 12/1994 | Anderson | |
| 5,415,665 A | 5/1995 | Hessel et al. | |
| 5,437,994 A | 8/1995 | Emerson et al. | |
| 5,460,964 A | 10/1995 | McGlave et al. | |
| 5,464,764 A | 11/1995 | Capecchi et al. | |
| 5,486,359 A | 1/1996 | Caplan et al. | |
| 5,487,992 A | 1/1996 | Capecchi et al. | |
| 5,516,532 A | 5/1996 | Atala et al. | |
| 5,591,625 A | 1/1997 | Gerson et al. | |
| 5,605,822 A | 2/1997 | Emerson et al. | |
| 5,627,059 A | 5/1997 | Capecchi et al. | |
| 5,635,386 A | 6/1997 | Palsson et al. | |
| 5,635,387 A | 6/1997 | Fei et al. | |
| 5,643,741 A | 7/1997 | Tsukamoto et al. | |
| 5,646,043 A | 7/1997 | Emerson et al. | |
| 5,654,186 A | 8/1997 | Cerami et al. | |
| 5,654,381 A | 8/1997 | Hrkach et al. | |
| 5,665,557 A | 9/1997 | Murray et al. | |
| 5,668,104 A | 9/1997 | Nakahata et al. | |
| 5,670,147 A | 9/1997 | Emerson et al. | |
| 5,670,351 A | 9/1997 | Emerson et al. | |
| 5,672,346 A | 9/1997 | Srour et al. | |
| 5,677,139 A | 10/1997 | Johnson | |
| 5,709,854 A | 1/1998 | Griffith-Cima et al. | |
| 5,716,616 A | 2/1998 | Prockop et al. | |
| 5,716,794 A | 2/1998 | Tjota et al. | |
| 5,716,827 A | 2/1998 | Tsukamoto | |
| 5,733,541 A | 3/1998 | Taichman et al. | |
| 5,733,542 A | 3/1998 | Haynesworth et al. | |
| 5,736,396 A | 4/1998 | Bruder et al. | |
| 5,744,361 A | 4/1998 | Hoffman et al. | |
| 5,750,397 A | 5/1998 | Tsukamoto et al. | |
| 5,763,197 A | 6/1998 | Tsukamoto et al. | |
| 5,763,266 A | 6/1998 | Palsson et al. | |
| 5,807,686 A | 9/1998 | Wagner et al. | |
| 5,811,094 A | 9/1998 | Caplan et al. | |
| 5,827,735 A | 10/1998 | Young et al. | |
| 5,827,740 A | 10/1998 | Pittenger | |
| 5,827,742 A | 10/1998 | Scadden | |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

U.S. Appl. No. 09/659,904, filed Sep. 12, 2000, Hariri.
U.S. Appl. No. 10/900,270, filed Jul. 28, 2004, Muller et al.
U.S. Appl. No. 11/580,588, filed Oct. 13, 2006, Paludan et al.
U.S. Appl. No. 11/580,625, filed Oct. 13, 2006, Heidaran et al.
U.S. Appl. No. 11/648,802, filed Dec. 28, 2006, Heidaran et al.
U.S. Appl. No. 11/648,804, filed Dec. 28, 2006, Edinger et al.
U.S. Appl. No. 11/648,812, filed Dec. 28, 2006, Heidaran et al.
U.S. Appl. No. 11/648,813, filed Dec. 28, 2006, Edinger et al.
U.S. Appl. No. 11/648,824, filed Dec. 28, 2006, Heidaran et al.
U.S. Appl. No. 12/187,337, filed Aug. 6, 2008, Heidaran et al.

(Continued)

*Primary Examiner* — Thaian N Ton
(74) *Attorney, Agent, or Firm* — Jones Day

(57) ABSTRACT

Provided herein are novel angiogenic cells from amnion, referred to as amnion derived adherent cells, and populations of, and compositions comprising, such cells. Further provided herein are methods of obtaining such cells and methods of using the cells in the treatment of individuals.

20 Claims, 15 Drawing Sheets

(56) References Cited

U.S. PATENT DOCUMENTS

| | | | |
|---|---|---|---|
| 5,837,539 | A | 11/1998 | Caplan et al. |
| 5,849,553 | A | 12/1998 | Anderson et al. |
| 5,851,984 | A | 12/1998 | Matthews et al. |
| 5,855,619 | A | 1/1999 | Caplan et al. |
| 5,858,782 | A | 1/1999 | Long et al. |
| 5,866,414 | A | 2/1999 | Badylak et al. |
| 5,874,301 | A | 2/1999 | Keller et al. |
| 5,877,299 | A | 3/1999 | Thomas et al. |
| 5,879,318 | A | 3/1999 | Van Der Heiden et al. |
| 5,879,940 | A | 3/1999 | Torok-Storb et al. |
| 5,905,041 | A | 5/1999 | Beug et al. |
| 5,906,934 | A | 5/1999 | Grande et al. |
| 5,908,782 | A | 6/1999 | Marshak et al. |
| 5,908,784 | A | 6/1999 | Johnstone et al. |
| 5,914,108 | A | 6/1999 | Tsukamoto et al. |
| 5,914,268 | A | 6/1999 | Keller et al. |
| 5,916,202 | A | 6/1999 | Haswell |
| 5,919,176 | A | 7/1999 | Kuypers et al. |
| 5,919,702 | A | 7/1999 | Purchio et al. |
| 5,922,597 | A | 7/1999 | Verfaille et al. |
| 5,925,567 | A | 7/1999 | Kraus et al. |
| 5,928,214 | A | 7/1999 | Rubinstein et al. |
| 5,928,947 | A | 7/1999 | Anderson et al. |
| 5,942,225 | A | 8/1999 | Bruder et al. |
| 5,942,496 | A | 8/1999 | Bonadio et al. |
| 5,958,767 | A | 9/1999 | Snyder et al. |
| 5,962,325 | A | 10/1999 | Naughton et al. |
| 5,968,829 | A | 10/1999 | Carpenter |
| 5,969,105 | A | 10/1999 | Feng et al. |
| 5,993,429 | A | 11/1999 | Kuypers et al. |
| 5,997,860 | A | 12/1999 | Brauer et al. |
| 6,001,654 | A | 12/1999 | Anderson et al. |
| 6,010,696 | A | 1/2000 | Caplan et al. |
| 6,011,000 | A | 1/2000 | Faller et al. |
| 6,020,469 | A | 2/2000 | Hershenson |
| 6,022,540 | A | 2/2000 | Bruder et al. |
| 6,022,743 | A | 2/2000 | Naughton et al. |
| 6,022,848 | A | 2/2000 | Kozlov et al. |
| 6,030,836 | A | 2/2000 | Thiede |
| 6,057,123 | A | 5/2000 | Craig et al. |
| 6,059,968 | A | 5/2000 | Wolf, Jr. |
| 6,077,708 | A | 6/2000 | Collins et al. |
| 6,087,113 | A | 7/2000 | Caplan et al. |
| 6,093,531 | A | 7/2000 | Bjornson et al. |
| 6,110,739 | A | 8/2000 | Keller et al. |
| 6,127,135 | A | 10/2000 | Hill et al. |
| 6,146,888 | A | 11/2000 | Smith et al. |
| 6,174,333 | B1 | 1/2001 | Kadiyala et al. |
| 6,179,819 | B1 | 1/2001 | Haswel |
| 6,184,035 | B1 | 2/2001 | Csete et al. |
| 6,190,368 | B1 | 2/2001 | Kuypers et al. |
| 6,214,369 | B1 | 4/2001 | Grande et al. |
| 6,224,860 | B1 | 5/2001 | Brown |
| 6,225,119 | B1 | 5/2001 | Qasba et al. |
| 6,227,202 | B1 | 5/2001 | Mataparkar |
| 6,231,880 | B1 | 5/2001 | Perrine |
| 6,239,157 | B1 | 5/2001 | Mbalaviele et al. |
| 6,248,587 | B1 | 6/2001 | Rodgers et al. |
| 6,251,383 | B1 | 6/2001 | Upadhyay et al. |
| 6,255,112 | B1 | 7/2001 | Thiede et al. |
| 6,261,549 | B1 | 7/2001 | Fernandez et al. |
| 6,280,718 | B1 | 8/2001 | Kaufman et al. |
| 6,281,012 | B1 | 8/2001 | McIntosh et al. |
| 6,300,314 | B1 | 10/2001 | Wallner et al. |
| 6,306,575 | B1 | 10/2001 | Thomas et al. |
| 6,312,950 | B1 | 11/2001 | Ohmura et al. |
| 6,322,784 | B1 | 11/2001 | Pittenger et al. |
| 6,326,019 | B1 | 12/2001 | Tseng |
| 6,326,198 | B1 | 12/2001 | Emerson et al. |
| 6,328,765 | B1 | 12/2001 | Hardwick et al. |
| 6,328,960 | B1 | 12/2001 | McIntosh et al. |
| 6,335,195 | B1 | 1/2002 | Rodgers et al. |
| 6,337,387 | B1 | 1/2002 | Sakano et al. |
| 6,338,942 | B2 | 1/2002 | Kraus et al. |
| 6,355,239 | B1 | 3/2002 | Bruder et al. |
| 6,368,636 | B1 | 4/2002 | McIntosh et al. |
| 6,387,367 | B1 | 5/2002 | Davis-Sproul et al. |
| 6,387,369 | B1 | 5/2002 | Pittenger et al. |
| 6,461,645 | B1 | 10/2002 | Boyse et al. |
| 6,497,875 | B1 | 12/2002 | Sorrell et al. |
| 6,541,024 | B1 | 4/2003 | Kadiyala et al. |
| 6,548,299 | B1 | 4/2003 | Pykett |
| 6,685,936 | B2 | 2/2004 | McIntosh et al. |
| 6,709,864 | B1 | 3/2004 | Pittenger et al. |
| 6,797,269 | B2 | 9/2004 | Mosca et al. |
| 6,835,377 | B2 | 12/2004 | Goldberg et al. |
| 6,863,900 | B2 | 3/2005 | Kadiyala et al. |
| 6,875,430 | B2 | 4/2005 | McIntosh et al. |
| 6,875,607 | B1 | 4/2005 | Reubinoff et al. |
| 7,029,666 | B2 | 4/2006 | Bruder et al. |
| 7,045,148 | B2 | 5/2006 | Hariri |
| 7,091,353 | B2 | 8/2006 | Robarge et al. |
| 7,147,626 | B2 | 12/2006 | Goodman et al. |
| 7,244,759 | B2 | 7/2007 | Muller et al. |
| 7,255,879 | B2 | 8/2007 | Hariri |
| 7,311,904 | B2 | 12/2007 | Hariri |
| 7,311,905 | B2 | 12/2007 | Hariri |
| 7,468,276 | B2 | 12/2008 | Hariri |
| 7,498,171 | B2 | 3/2009 | Hariri et al. |
| 7,638,141 | B2 | 12/2009 | Hariri |
| 7,642,091 | B2 | 1/2010 | Lee et al. |
| 7,682,803 | B2 | 3/2010 | Paludan et al. |
| 2001/0005591 | A1 | 6/2001 | Qasba et al. |
| 2001/0038836 | A1 | 11/2001 | During et al. |
| 2002/0102239 | A1 | 8/2002 | Koopmans |
| 2002/0123141 | A1 | 9/2002 | Hariri |
| 2002/0132343 | A1 | 9/2002 | Lum |
| 2002/0160510 | A1 | 10/2002 | Hariri |
| 2003/0032179 | A1 | 2/2003 | Hariri |
| 2003/0044977 | A1 | 3/2003 | Sakuragawa et al. |
| 2003/0045552 | A1 | 3/2003 | Robarge et al. |
| 2003/0096841 | A1 | 5/2003 | Robarge et al. |
| 2003/0161818 | A1 | 8/2003 | Weiss et al. |
| 2003/0180269 | A1 | 9/2003 | Hariri |
| 2003/0235563 | A1 | 12/2003 | Strom et al. |
| 2003/0235909 | A1 | 12/2003 | Hariri |
| 2004/0018617 | A1 | 1/2004 | Hwang |
| 2004/0028660 | A1 | 2/2004 | Hariri et al. |
| 2004/0048372 | A1 | 3/2004 | Hariri |
| 2004/0048796 | A1 | 3/2004 | Hariri et al. |
| 2004/0107453 | A1 | 6/2004 | Furcht et al. |
| 2004/0136967 | A1 | 7/2004 | Weiss et al. |
| 2004/0161419 | A1 | 8/2004 | Strom et al. |
| 2004/0171147 | A1 | 9/2004 | Hariri |
| 2004/0180040 | A1 | 9/2004 | Phillips et al. |
| 2004/0219136 | A1 | 11/2004 | Hariri |
| 2004/0229351 | A1 | 11/2004 | Rodriguez |
| 2004/0241144 | A1 | 12/2004 | Kaps et al. |
| 2004/0258670 | A1* | 12/2004 | Laughlin et al. .......... 424/93.21 |
| 2005/0019865 | A1 | 1/2005 | Kihm et al. |
| 2005/0019908 | A1 | 1/2005 | Hariri |
| 2005/0032209 | A1 | 2/2005 | Messina et al. |
| 2005/0037491 | A1 | 2/2005 | Mistry et al. |
| 2005/0042595 | A1 | 2/2005 | Haas |
| 2005/0054093 | A1 | 3/2005 | Haas |
| 2005/0054098 | A1 | 3/2005 | Mistry et al. |
| 2005/0058629 | A1 | 3/2005 | Harmon et al. |
| 2005/0058630 | A1 | 3/2005 | Harris et al. |
| 2005/0058631 | A1 | 3/2005 | Kihm et al. |
| 2005/0085543 | A1 | 4/2005 | Wallimann et al. |
| 2005/0089513 | A1 | 4/2005 | Sakuragawa et al. |
| 2005/0112104 | A1 | 5/2005 | Pittenger et al. |
| 2005/0118712 | A1 | 6/2005 | Tsai et al. |
| 2005/0118715 | A1 | 6/2005 | Hariri et al. |
| 2005/0124003 | A1 | 6/2005 | Atala et al. |
| 2005/0143420 | A1 | 6/2005 | Moutouh-de Parseval et al. |
| 2005/0148034 | A1 | 7/2005 | Hariri et al. |
| 2005/0148074 | A1 | 7/2005 | Davies et al. |
| 2005/0176139 | A1 | 8/2005 | Chen et al. |
| 2005/0181502 | A1 | 8/2005 | Furcht et al. |
| 2005/0186182 | A1 | 8/2005 | Deisher et al. |
| 2005/0233452 | A1 | 10/2005 | Ho et al. |
| 2005/0239897 | A1 | 10/2005 | Pittenger et al. |
| 2005/0266391 | A1 | 12/2005 | Bennett et al. |

(56) References Cited

U.S. PATENT DOCUMENTS

| | | |
|---|---|---|
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0160588 A1* | 7/2007 | Kihm .................. 424/93.21 |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0253931 A1 | 11/2007 | Varney et al. |
| 2007/0258963 A1 | 11/2007 | Danilkovitch et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044392 A1 | 2/2008 | Kues et al. |
| 2008/0044848 A1 | 2/2008 | Heidaran |
| 2008/0050347 A1 | 2/2008 | Ichim |
| 2008/0050814 A1 | 2/2008 | Allickson |
| 2008/0064098 A1 | 3/2008 | Allickson |
| 2008/0069895 A1 | 3/2008 | Liu et al. |
| 2008/0095749 A1 | 4/2008 | Aggarwal et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0159998 A1 | 7/2008 | Ichim |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2008/0226612 A1 | 9/2008 | Treves et al. |
| 2008/0248005 A1 | 10/2008 | Phan |
| 2008/0254005 A1 | 10/2008 | Riordan et al. |
| 2008/0254538 A1 | 10/2008 | Messina et al. |
| 2008/0260694 A1 | 10/2008 | Gronthos et al. |
| 2008/0260703 A1 | 10/2008 | Riordan et al. |
| 2008/0260704 A1 | 10/2008 | Riordan et al. |
| 2008/0274087 A1 | 11/2008 | Li et al. |
| 2008/0279956 A1 | 11/2008 | Lin |
| 2008/0286249 A1 | 11/2008 | Varney et al. |
| 2008/0286267 A1 | 11/2008 | Sing et al. |
| 2008/0292597 A1 | 11/2008 | Steenblock |
| 2008/0299090 A1 | 12/2008 | Weiss et al. |
| 2008/0305148 A1 | 12/2008 | Fu |
| 2008/0311087 A1 | 12/2008 | Gosiewska et al. |
| 2009/0004738 A1 | 1/2009 | Merchav et al. |
| 2009/0016999 A1 | 1/2009 | Cohen et al. |
| 2009/0053182 A1 | 2/2009 | Ichim et al. |
| 2009/0053805 A1 | 2/2009 | Hariri |
| 2009/0074728 A1 | 3/2009 | Gronthos et al. |
| 2009/0074731 A1 | 3/2009 | Librach et al. |
| 2009/0075381 A1 | 3/2009 | Clarke et al. |
| 2009/0081171 A1 | 3/2009 | Fu et al. |
| 2009/0092653 A1 | 4/2009 | Colter et al. |
| 2009/0104158 A1 | 4/2009 | Young et al. |
| 2009/0104163 A1 | 4/2009 | Deans et al. |
| 2009/0104164 A1 | 4/2009 | Zhang et al. |
| 2009/0123437 A1 | 5/2009 | Takebe |
| 2009/0124007 A1 | 5/2009 | Cho |
| 2009/0136457 A1 | 5/2009 | Sing et al. |
| 2009/0136471 A1 | 5/2009 | Heidaran et al. |
| 2009/0142831 A1 | 6/2009 | Hariri |
| 2009/0149371 A1 | 6/2009 | Mistry et al. |
| 2009/0169522 A1 | 7/2009 | Danilkovitch et al. |
| 2009/0169597 A1 | 7/2009 | Brown et al. |
| 2009/0186006 A1 | 7/2009 | Murphy |
| 2009/0208463 A1 | 8/2009 | Pittenger et al. |
| 2009/0214493 A1 | 8/2009 | Pittenger et al. |
| 2009/0220464 A1 | 9/2009 | Aggarwal et al. |
| 2009/0226406 A1 | 9/2009 | Hariri |
| 2009/0238801 A1 | 9/2009 | Woodbury et al. |
| 2009/0252710 A1 | 10/2009 | Zhang et al. |
| 2009/0263361 A1 | 10/2009 | Lee et al. |
| 2009/0280093 A1 | 11/2009 | Friedlander |
| 2009/0291061 A1 | 11/2009 | Riordan et al. |
| 2009/0304639 A1 | 12/2009 | Yokoo et al. |
| 2009/0324609 A1 | 12/2009 | Lodie et al. |
| 2010/0028306 A1 | 2/2010 | Clarke et al. |
| 2010/0105132 A1 | 4/2010 | Totey et al. |

FOREIGN PATENT DOCUMENTS

| | | |
|---|---|---|
| CN | 1786154 | 6/2006 |
| EP | 0333328 | 9/1989 |
| EP | 1288293 A1 | 3/2003 |
| EP | 1384775 A1 | 1/2004 |
| EP | 1535994 | 6/2005 |
| EP | 1775341 | 4/2007 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06666 | 5/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 99/64566 | 12/1999 |
| WO | WO 00/17325 | 3/2000 |
| WO | WO 00/27999 | 5/2000 |
| WO | WO 00/73421 | 12/2000 |
| WO | WO 01/93909 | 12/2001 |
| WO | WO 03/042405 | 5/2003 |
| WO | WO 03/089619 | 10/2003 |
| WO | WO 03/102151 | 12/2003 |
| WO | WO 2004/087896 | 10/2004 |
| WO | WO 2005/042703 | 5/2005 |
| WO | WO 2005/105992 | 11/2005 |
| WO | WO 2006/015214 | 2/2006 |

(56) References Cited

FOREIGN PATENT DOCUMENTS

| WO | WO 2006/111706 | 10/2006 |
|---|---|---|
| WO | WO 2006/117889 | 11/2006 |
| WO | WO 2007/024441 | 3/2007 |
| WO | WO 2007/047468 | 4/2007 |
| WO | WO 2007/056578 | 5/2007 |
| WO | WO 2007/071048 | 6/2007 |
| WO | WO 2007/087293 | 8/2007 |
| WO | WO 2007/124594 | 11/2007 |
| WO | WO 2007/136673 | 11/2007 |
| WO | WO 2008/036374 | 3/2008 |
| WO | WO 2008/036447 | 3/2008 |
| WO | WO 2008/051568 | 5/2008 |
| WO | WO 2008/100497 | 8/2008 |
| WO | WO 2008/148105 | 12/2008 |
| WO | WO 2008/152640 | 12/2008 |
| WO | WO 2008/156659 | 12/2008 |
| WO | WO 2009/007979 | 1/2009 |
| WO | WO 2009/035612 | 3/2009 |
| WO | WO 2009/037690 | 3/2009 |
| WO | WO 2009/046346 | 4/2009 |
| WO | WO 2009/046377 | 4/2009 |
| WO | WO 2009/052132 | 4/2009 |
| WO | WO 2009/134532 | 11/2009 |
| WO | WO 2009/144720 | 12/2009 |

OTHER PUBLICATIONS

U.S. Appl. No. 12/618,664, filed Nov. 13, 2009, Hariri.
U.S. Appl. No. 12/624,359, filed Nov. 23, 2009, Hariri.
U.S. Appl. No. 12/687,851, filed Jan. 14, 2010, Paludan et al.
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Anker In'T P et al, "Isolation of Mesenchymal Stem Cells of Fetal or Maternal Origin from Human lacenta," Stem Cells, Alphamed Press, Dayton, OH, US, vol. 22, No. 7, 2004, pp. 1338-1345.
Aplin, "Implantation, trophoblast Differentiation and Haemochorial Placentation: Mechanistic Evidence in vivo and in vitro," Journal of Cell Science 99:681-692 (1991).
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barry, "Where do all the placentas go?" Canadian Journal of Infection Control 9(1):8-10 (1994).
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(−) Progenitor Cell Recovery Using a Novel Umbilical Cord Blood Collection System," Stem Cells 18(4):245-251 (2000).
Bloxam et al., "Culture of Syncytiotrophoblast for the Study of Human Placental Transfer. Part I: Isolation and Purification of Cytotrophoblast,"Placenta 18:93-98 (1997).
Bloxam, "Human Placental Trophoblast Culture: One-Sided and Two-Sided Models," Proceedings of the Nutrition Society 50:349-354 (1991).
Bullen et al., "Two-Sided Culture of Human Placental Trophoblast. Morphology, Immunocytochemistry and Permeability Properties," Placenta 11:431-450 (1990).
Campagnoli, et al., "Identification of Mesenchymal Stem/Progenitor Cells in Human First-Trimester Fetal Blood, Liver, and Bone Marrow." Blood 98(8):2396-402 (2001).
Caplan, "The Mesengenic Process," Clin. Plast. Surg. 21(3):429-435 (1994).
Caniggia et al., "Oxygen and Placental Development During the First Trimester: Implications for the Pathophysiology of Pre-Eclampsia," PubMed, Placenta 21(Suppl A):S25-30 (2000).
Cester et al., "Cation Transport Across Cultured Trophoblast Membrane in Preeclampsia," Clin. and Exper. Hyper. In Pregnancy, B11(1):59-69 (1992).
Chang, et al., "Placenta-Derived Multipotent Cells Exhibit Immunosuppressive Properties That Are Enhanced in the Presence of Interferon-gamma," Stem Cells 24:2466-2477 (2006).
Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chies et al., "Sickle Cell Disease: A Chronic Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Contractor, et al., "A comparison of the effects of different perfusion regimens on the structure of the isolated human placental lobule," Cell Tissue Res. 237:609-617 (1984).
Cosma, et al., "Use and Application of Stem Cells in Toxicology," SOT 2003 Annual Meeting, p. 4, Abstract 19.
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Clark David A et al, "Placental trophoblast from successful human pregnancies expresses the tolerance signaling molecule, CD200 (OX-2)" American Journal of Reproductive immunology, Munksgaard International Publishers, Copenhagen, DK, vol. 50, No. 3, Sep. 2003, pp. 187-195, XP002430047 ISSN: 1046-7408.
Czarneski, et al., "Effects of Cord Blood Transfer on the Hematopoietic Recovery Following Sublethal Irradiation in MRL lpr/lpr Mice," Proc. Soc. Exp. Biol. Med. 220(2):79-87 (1999).
Database WPI Week 200357 Derwent Publications Ltd., London, GB, AN 2003-59905 & CN 1 407 888 A (Zhou S) Apr. 2, 2003.
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies et al., "Thalidomide (Thal) and immunomodulatory derivatives (IMiDs) augment natural killer (NK) cell cytotoxicity in multiple myeloma ~MM)," Abstract # P222, VIIIth International Myeloma Workshop, May 4-8, 2001.
Davila, et al., "Use and Application of Stem Cells in Toxicology," Toxicological Sciences 79:214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
De Filippo, et al., "Total Penile Urethra Replacement with Autologous Cell-Seeded Collagen Matrices." Urology and Reproductive Surgery, vol. 195, No. 3S, Sep. 2002, p. S95.

(56) References Cited

OTHER PUBLICATIONS

De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).

Dominici, et al., "Minimal Criteria for Defining Multipotent Mesenchymal Stromal Cells. The International Society for Cellular Therapy Position Statement," Cytotherapy 8(4):315-317 (2006).

Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).

Dushnik-Levinson, et al. "Embryogenesis in vitro: study of differentiation of embryonic stem cells." Biol Neonate. 67(2):77-83 (1995).

Elchalal, et al., "Postpartum Umbilical Cord Blood Collection for Transplantation: a Comparison of Three Methods," Am. J. of Obstetrics & Gyn. 182(1 Pt 1):227-232 (2000).

Ende, "Berashis Cells in Human Umbilical Cord Blood Vs. Embryonic Stem Cells," J. Med. 33(1-4):167-171 (2002).

Ende, et al., "Human Umbilical Cord Blood Cells Amerliorate Alzheimer's Disease in Transgenic Mice," J. Med. 32(3-4):241-7 (2001).

Ende, et al., "Human Umbilical Cord Blood Cells Ameliorate Huntington's Disease in Transgenic Mice," J. Med. 32(3-4):231-240 (2001).

Ende, et al., "Human Umbilical Cord Blood Effect on SOD Mice (Amyotrophic Lateral Sclerosis)," Life Sci. 67(1):53-59 (2001).

Ende, et al., "Parkinson's Disease Mice and Human Umbilical Cord Blood," Journal of Medicine 33(1-4):173-180 (2002).

Ende, et al., "Pooled Umbilical Cord Blood as a Possible Universal Donor for Marrow Reconstitution and Use in Nuclear Accidents," Life Sci. 69:1531-1539 (2001).

Ende, et al., "The Effect of Human Cord Blood on SJL/J Mice After Chemoablation and Irradiation and Its Possible Clinical Significance," Immunol. Invest. 24(6):999-1012 (1995).

Ende, "Collection of Umbilical Cord Blood for Transplantation," Blood 80(6):1623-1624 (1992).

Ende, "The Feasibility of Using Blood Bank Stored (4° C.) Cord Blood, Unmatched for HLA for Marrow Transplantation," Am. J. Clin. Pathol. 111:773-781 (1999).

Erices et al., "Mesenchymal progenitor cells in human umbilical cord blood," Br. J. Haemotol. 109(1):Abstract (2000).

Evans, "Stem Cell Therapy: Moving towards Reality," Am. J. Obstet. Gynecol. 194:662-663 (2006).

Fasouliotis et al., "Human umbilical cord blood banking and transplantation: a state of the art," Eur. J. Obstet. Gynecol. Reprod. Biol. 90(1):13-25 (2000).

Fisher et al., "Adhesive and Degradatie Properties of Human Placental Cytotrophoblast Cells in Vitro," Journal od Cell Biology 109:891-902 (1989).

Frank H G, et al., "Cell culture models of human trophoblast: primary culture of trophoblast—a workshop report." Placent Apr. 2001, vol. 22 Suppl A, Apr. 2001, pp. S107-S109, XP002443188 ISSN: 0143-4004.

Genbacev et al., "Regulation of Human Placental Development by Oxygen Tension," 277(5332):1669-1672.

Gluckman, et al., "Cord Blood Heamatopoietic Stem Cells: Biology and Transplantation," In: Hematology, American Society of Hematology Education Program Book (1998) p. 1-14.

Gluckman, et al., "Results of Unrelated Umbilical Cord Blood Hematopoeietic Stem Cell Transplant," Transfusion Cinique et Biologique 8(3):146-154 (2001).

Greenwood et al., "Membrane Potential Difference and Intracellular Cation Concentrations in Human Placental Trophoblast Cells in Culture," Journal of Physiology 492.3:629-640 (1996).

Hadjantonakis, et al., "The Stem Cells of Early Embryos," Differentiation 68:159-166 (2001).

Hamada, et al., "Mesenchymal Stem Cells (MSC) as Therapeutic Cytoreagents for Gene Therapy," Cancer Sci 96:149-156 (2005).

Harbacheuski, et al., "Placenta Derived Adherent Cells (PDACs) Supress Tumor Cells of Diverse Origin." Blood 108(11):288 (2006).

Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).

Hattori et al., "Molecular Cloning of Adipocyte-Derived Leucine Aminopeptidase Highly Related to Placental Leucine Aminopeptidase/Oxytocinase," J. Biochem. 125(5):931-938 (1999).

Hatzopoulos, et al. "Isolation and characterization of endothelial progenitor cells from mouse embryos," Development. 125(8):1457-68 (1998).

Himori, et al., Chemotherapeutic susceptibility of human bone marrow progenitor cells and human myelogenous leukemia cells (HL-60) in co-culture: preliminary report. Int J Cell Cloning. 2(4):254-62 (1984).

Hirano et al., "CD9 is Expressied in Extravillous Trophoblasts in Association with Integrin $\alpha 3$ and integrin $\alpha 5$," Molecular Human Reproduction 5(2):162-167 (1999).

Hirashima, et al. "Maturation of embryonic stem cells into endothelial cells in an in vitro model of vasculogenesis," Blood. 93(4):1253-63 (1999).

Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075.

Hows, "Status of Umbilical Cord Blood Transplantation in the Year 2001," J Clin Pathol 54(6):428-434 (2001).

Huss, "Isolation of Primary and Immortalized CD34-Hematopoietic and Mesenchymal Stem Cells from Various Sources," Stem Cells 18:1-9 (2000).

Huss, "Perspectives on the Morphology and Biology of CD34-Negative Stem Cells," J. Hematother. Stem. Cell Res. 9(6):783-793 (2000).

Igura, et al., "Isolation and Characterization of Mesencymal Progenitor Cells from Chorionic Villi of Human Placenta," Cytotherapy 6(6): 543-553 (2004).

International Preliminary Report on Patentability from PCT/US2006/049491 dated Jan. 14, 2008.

Ilancheran, et al., "Stem Cells Derived from Human Fetal Membranes Display Multilineage Differentiation Potential," Biology of Reproduction, 77, 577-588 (2007).

Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).

Jaiswal, et al., "Osteogenic Differentiation of Purified, Culture-Expanded Human Mesenchymal Stem Cells in vitro," J. Cell Biochem. 64(2):295-312 (1997).

James et al., "Cytotrophobast Differentiation in the First Trimester of Pregnancy: Evidence for Separate Progenitros of Extravillous Trophoblasts and Syncytiotrophoblast," Reproduction 130:95-130 (2005).

Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2010).

Jones et al., "Ultrastructure of the Normal Human Placenta," Electron Microsc. 4:129-178 (1991).

Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).

Kato et al., "Discordant Secretion of Placental Protein Hormones in Differentiating Trophoblasts in Vitro," Journal of Clinical Endocrinology and Metabolism 68(4):814-820 (1989).

Kaufmann et al., "Extravillous Trophoblast in the Human Placenta," Trophoblast Research 10:21-65 (1997).

Kliman et al., "Purification, Characterization, and in Vitro Differentiation of Cytotropholblasts from Human Term Placentae," Endocrinology 118(4):1567-1582 (1986).

(56) References Cited

OTHER PUBLICATIONS

Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).

Koh, et al., "Parthenolgenetically Derived Stem Cells for Urologic Reconstruction." The Journal of Urology, vol. 171, No. 4, Supplement, Saturday, May 8, 2004, p. 21, Abstract 81.

Korbling, et al., "Hepatocytes and Epithelial Cells of Donor Origin in Recipients of Peripheral-Blood Stem Cells," N. Engl. J. Med. 346(10):738-746 (2002).

Kurtzberg, "Placental Bood as a Surce of Hmatopoietic Sem Cells for Transplantation into Unrelated Recipients," N. Engl. J. Med. 335:157-166 (1996).

Landon et al., "The Effects of Ethanol Methotrexate and Diphenylhydantoin on [$^{14}$C] Leucine Incorporation by Human Trophoblasst Cells Cultured in Vitro," British Journal of Obstetrics and Gynaecology 94:252-255 (1987).

Law, E., et al., Stem Cell Symposium, State of New Jersey Commission on Science & Technology 2005 (Abstract).

Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).

Lebkowski, et al., "Serum and Plasma Levels of FGF-2 and VEGF in Healthy Blood Donors," Cancer J. 7(Suppl 2):S83-S93 (2001).

Leonard, et al., "The Role of ABC Transporters in Clinical Practice," Oncologist. 8:411-424 (2003).

Li, et al., "Mesenchymal Stem Cells Derived from Human Placenta Suppress Allogenic Umbilical Cord Blood Lymphocyte Proliferation." Cell Res. 15: 539-547 (2005).

Lin, et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626.

Lipinski et al., "Human Trophoblast Cell-Surface Antigen Defined by Monoclonal Antibodies," Proc. Natl. Acad. Sci. USA, Medical Sciences 78(8):5147-5150 (1981).

Loke et al., "Identification of Cytotrophoblast Colonies in Cultures of Human Placental Cells Using Monoclonal Antibodies," Placenta 7:221-231 (1986).

Lorkowski, et al., "ABCG Subfamily of Human ATP-Binding Cassette Proteins," Pure Appl. Chem. 74(11):2057-2081 (2002).

Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).

Ma, et al., "Development of an in vitro Human Placenta Model by the Cultivation of Human Trophoblasts in a Fiber-Based Bioreactor System," Tissue Engineering 5, 91-102 (1999).

McMaster et al, "Human Placental HLA-G Expression is Restricted to Differentiated Cytotrophoblasts," J. Immunol. 154(8):3771-3778 (1995).

Melchner, et al., "Human Placental Conditioned Medium Reverses Apparent Commitment to Differentiation of Human Promyelocytic Leukemia Cells (HL60)," Blood 66(6): 1469-1472 (1985).

Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).

Miki, et al., "Isolation of Multipotent Stem Cells from Placenta." AASLD Abstracts, Hepatology, Oct. 2003, Abstract 279, p. 290A.

Miki, et al., "Production of Hepatocytes from Human Amniotic Stem Cells." Hepatology, Abstract 20, vol. 36, No. 4, Pt. 2, 2002.

Miki, et al., "Stem Cell Characteristics of Amniotic Epithelial Cells." Stem Cells Express, published online Aug. 9, 2005; doi:10. 1634/stemcells.2004-0357.

Minguell, et al., "Mesenchymal Stem Cells," Exp. Biol. Med. 226:507-520 (2001).

Moore, et al., "A Simple Perfusion Technique for Isolation of Maternal Intervillous Blood Mononuclear Cells from Human Placentae," J. Immunol. Methods 209(1):93-104 (1997).

Morgan et al., "Human Placental Cell Culture," Biochemical Society Transactions 12 (1984).

Morgan et al., "Long-Term Culture of Human Trophoblast Cells," British Journal of Obstetrics and Gynaecology 92:84-92 (1985).

Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).

Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).

Muhlemann, et al., "Cytomegalovirus in the Perfused Human Term Placenta in vitro," Placenta 16:367-373 (1995).

Myllynen "In Search of Models for Hepatic and Placental Pharmacokinetics," [Dissertation] University of Oulu, (2003).

Nishishita, et al., "A Potential Pro-Angiogenic Cell Therapy with Human Placenta-Derived Mesenchymal Cells," Biochem. Biophys. Res. Commun. 325(1):24-31 (2004).

Noort, et al., "Mesenchymal Stem Cells Promote Engraftment of Human Umbilical Cord Blood-Derived CD34+ Cells in NOD/SCID Mice," Experimental Hematology 30(8):870-878 (2002).

Notice of Opposition by Farmindustria S.A. to corresponding claims filed in Peru; English translation May 5, 2008.

Oda et al., "Trophoblast Stem Cells," Methods in Enxymology 419(15):387-400 (2006).

Paludan, et al., "Immune Suppression by Placenta Derived Adherent Cells (PDAC) Correlate with Monocyte Chemoattractant Protein-1 and 1L-2 Secretion," Blood 108 (2006) (abstract only).

Paludan, et al., "Placental Derived Stem Cells (PDAC) Suppress the Allo-MLR and the EBV Regression Assay," http://www.call4abstract.com/hem/finalpreview.php?absnum=552996 (2006).

Pande et al., "Isolation and Culture of Hamster Ectoplacental Cone Trophoblasts: an in Vitro Study on the Cell Types and Their Growth Pattern," Cell Prolif. 29:163-171 (1996).

Papaioannou, et al., "Stem Cells from Early Mammalian Embryos" Stem Cells Handbook:19-31 (2004).

Pellegrini, et al., "FADD and Caspase-8 Are Required for Cytokine-Induced Proliferation of Hemopoietic Progenitor Cells," Blood 106(5):1581-1589 (2005).

Petroff et al., "Isolation and Culture of Term Human Trophoblast Cells," Methods in Molecular Medicine, Placenta and Trophoblast, 1(16):203-217 (2006).

Pittenger, M. F., et al. "Multilineage Potential of Adult Human Mesenchymal Stem Cells." *Science* (1999) U.S. vol. 284, No. 5411, pp. 143-147.

Portmann-Lanz, et al., "Placental Mesenchymal Stem Cells as Potential Autologous Graft for Pre-and Perinatal Neuroregeneration" Am. J. Obstet Gynecol. 194:664-673 (2006).

Potgens et al., "Human Trophoblast Contains an Intracellular Protein Reactive with and Antibody against CD133-A Novel Marker for Trophoblast," Placenta 22:639-645 (2001).

Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).

Quinn et al., "Mouse Trophoblast Stem Cells," Methods in Molecular Medicine 121(1):125-148 (2005).

Rachmilewitz et al., "Intermediate Cells During Cytotrphoblast Differentiation in Vitro," Cell Growth & Differentiation 4:395-402 (1993).

Reyes, et al., "Purification and ex vivo Expansion of Postnatal Human Marrow Mesodermanl Progenitor Cells," Blood 98(9):2615-2625 (2001).

Reyes, et al., Origin of endothelial progenitors in human postnatal bone marrow. J Clin Invest. 109(3):337-46 (2002).

Rielland et al., "Trophoblast Stem Cell Derivation, Cross-species Comparison and Use of Nuclear Transfer: New Tools to Study Trophoblast Growth and Differentiation," Developmental Biology 322:1-10 (2008).

(56) References Cited

OTHER PUBLICATIONS

Ringler et al., "In Vitro Systems for the Study of Human Placental Endocrine Function," Endocrine Reviews 11(1):105-123.
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(Suppl A):S10-S16 (2008).
Schutz, et al., "Isolation and Cultivation of Endothelial Cells Derived from Human Placenta," Eur. J. Cell Biol. 395-401 (1996).
ScienCell—Human Amniotic Epithelial Cells. http://www.sciencellonline.com/products/7100.htm.
Shamblott, et al., "Derivation of Pluripotent Stem Cells from Cultured Human Primordial Germ Cells," Proc. Natl. Acad. Sci. USA 95(23):13726-13731 (1998).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," In Vitro 14(7):6331-638 (1978).
Sunderland et al., "HLA A, B, C Antigens Are Expressed on Nonvillous Trophoblast of the Early Human Placenta," Journal of Immunology 127(6):2614-2615 (1981).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-7 (1998).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Turner, et al., "A modified Harvest Technique for Cord Blood Hematopoietic Stem Cells," Bone Marrow Transplantation 10:89-91 (1992).
Viacord, Umblicical cord blood can save lives (Informational brochure), Boston: ViaCell CENTR-BRO R1 10/01 (2001).
Wang, et al., "Enhanced Recovery of Hematopoietic Progenitor and Stem Cells from Cultivated, Postpartum Human Placenta," Blood 98(11/1):183a Abstract No. 769 (2001).
Wang, et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).

Watanabe, et al, "Multilineage Potential of Human Placenta-Derived Mesenchymal Cells," Blood 100(11):517a, Abstract 2022 (2002).
Wiesmann, et al., "Effects of Caspase Inhibitors on Hematopoietic Engraftment After Short-Term Culture," Cell. Transplant. 11(4):351-358 (2002).
Woods et al., "Osomometric and permeability characteristics of human placental/umbilical cord blood CD34+ cells and their application to cryopreservation," *J. Hematother. Stem Cell Res.* 9(2):161-173 (2000).
Yen B. Linju et al, "Isolation of multipotent cells from human term placenta" Stem Cells (Dayton, Ohio) 2005, vol. 23, No. 1, Jan. 2005, pp. 3-9, XP002443187 ISSN: 1065-5099.
Xu et al., "BMP4 Initiates Human Embryonic Stem Cell Differentiation to Trophoblast," Nature Biology 20:1261-1264 (2002).
Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).
Ye, et al., "Recovery of Placental-Derived Adherent Cells with Mesenchymal Stem Cell Characteristics," Blood 98(11/1):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yui et al., "Functional, Long-term Cultures of Human Term Trophoblasts Purified by Column-elimination of CD9 Expressing Cells," Placenta 15:231-246 (1994).
Zhang, et al., "Human Placenta-Derived Mesenchymal Progenitor Cells Support Culture Expansion of Long-Term Culture-Initiating Cells from Cord Blood CD34+ Cells." Exp. Hematol. 32: 657-664 (2004).
Office Action dated Aug. 28, 2003 in U.S. Appl. No. 10/076,180.
Office Action dated Jun. 20, 2005 in U.S. Appl. No. 10/076,180.
Office Action dated Mar. 18, 2004 in U.S. Appl. No. 10/076,180.
Office Action dated Oct. 20, 2004 in U.S. Appl. No. 10/076,180.
Advisory Action dated Jul. 12, 2004 in U.S. Appl. No. 10/076,180.
Advisory Action dated Feb. 2, 2007 in U.S. Appl. No. 10/366,671, now U.S. Pat. No. 7,311,905.
Notice of Allowance dated Oct. 30, 2008 in U.S. Appl. No. 10/411,655, now U.S. Pat. No. 7,498,171.
Office Action dated Feb. 28, 2008 in U.S. Appl. No. 10/411,655, now U.S. Pat. No. 7,498,171.
Office Action dated Jul. 11, 2007 in U.S. Appl. No. 10/411,655, now U.S. Pat. No. 7,498,171.
Office Action dated May 18, 2006 in U.S. Appl. No. 10/411,655, now U.S. Pat. No. 7,498,171.
Office Action dated Nov. 20, 2006 in U.S. Appl. No. 10/411,655, now U.S. Pat. No. 7,498,171.
Office Action dated Apr. 26, 2007 in U.S. Appl. No. 10/449,248.
Office Action dated Aug. 29, 2006 in U.S. Appl. No. 10/449,248.
Office Action dated Feb. 7, 2008 in U.S. Appl. No. 10/449,248.
Advisory Action dated Feb. 20, 2007 in U.S. Appl. No. 10/640,428, now U.S. Pat. No. 7,255,879.
Office Action dated Apr. 2, 2009 in U.S. Appl. No. 10/721,144.
Office Action dated Mar. 18, 2010 in U.S. Appl. No. 10/721,144.
Advisory Action dated Oct. 7, 2009 in U.S. Appl. No. 10/721,144.
Advisory Action dated Aug. 17, 2009 in U.S. Appl. No. 10/721,144.
Advisory Action dated Feb. 6, 2006 in U.S. Appl. No. 10/721,144.
Office Action dated Sep. 9, 2008 in U.S. Appl. No. 10/874,828, now U.S. Pat. No. 7,468,276.
Notice of Allowance dated Oct. 14, 2008 in U.S. Appl. No. 10/874,828, now U.S. Pat. No. 7,468,276.
Notice of Allowance dated Aug. 12, 2009 in U.S. Appl. No. 11/187,400.
Office Action dated May 22, 2008 in U.S. Appl. No. 11/187,400.
Office Action dated Feb. 20, 2009 in U.S. Appl. No. 11/187,400.
Advisory Action dated Sep. 8, 2008 in U.S. Appl. No. 11/187,400.
Office Action dated Dec. 3, 2008 in U.S. Appl. No. 11/648,802.
Non-Final Office Action dated Oct. 21, 2009 in U.S. Appl. No. 11/648,804.
Non-Final Office Action dated Jan. 22, 2010 in U.S. Appl. No. 11/648,824.

(56) References Cited

OTHER PUBLICATIONS

Notice of Allowance dated Sep. 15, 2005 in U.S. Appl. No. 10/004,942, now U.S. Pat. No. 7,045,148.
Office Action dated Dec. 5, 2003 in U.S. Appl. No. 10/004,942, now U.S. Pat. No. 7,045,148.
Office Action dated Jun. 15, 2004 in U.S. Appl. No. 10/004,942, now U.S. Pat. No. 7,045,148.
Office Action dated Jun. 20, 2005 in U.S. Appl. No. 10/004,942, now U.S. Pat. No. 7,045,148.
Office Action dated May 7, 2003 in U.S. Appl. No. 10/004,942, now U.S. Pat. No. 7,045,148.
Office Action dated Dec. 16, 2004 in U.S. Appl. No. 10/004,942, now U.S. Pat. No. 7,045,148.
Notice of Allowance dated Aug. 16, 2007 in U.S. Appl. No. 10/074,976, now U.S. Pat. No. 7,311,904.
Office Action dated Jan. 5, 2006 in U.S. Appl. No. 10/074,976, now U.S. Pat. No. 7,311,904.
Office Action dated Mar. 22, 2007 in U.S. Appl. No. 10/074,976, now U.S. Pat. No. 7,311,904.
Office Action dated Sep. 20, 2006 in U.S. Appl. No. 10/074,976, now U.S. Pat. No. 7,311,904.
Office Action dated Sep. 23, 2004 in U.S. Appl. No. 10/074,976, now U.S. Pat. No. 7,311,904.
Notice of Allowance dated Sep. 10, 2007 in U.S. Appl. No. 10/366,671, now U.S. Pat. No. 7,311,905.
Office Action dated Jan. 19, 2006 in U.S. Appl. No. 10/366,671, now U.S. Pat. No. 7,311,905.
Office Action dated May 14, 2007 in U.S. Appl. No. 10/366,671, now U.S. Pat. No. 7,311,905.
Office Action dated Oct. 10, 2006 in U.S. Appl. No. 10/366,671, now U.S. Pat. No. 7,311,905.
Notice of Allowance May 21, 2007 in U.S. Appl. No. 10/640,428, now U.S. Pat. No. 7,255,879.
Office Action dated Jan. 19, 2006 in U.S. Appl. No. 10/640,428, now U.S. Pat. No. 7,255,879.
Office Action dated Oct. 18, 2006 in U.S. Appl. No. 10/640,428, now U.S. Pat. No. 7,255,879.
Office Action dated Feb. 5, 2008 in U.S. Appl. No. 10/721,144.
Final Office Action dated Jun. 27, 2007 in U.S. Appl. No. 10/721,144.
Office Action dated Dec. 28, 2006 in U.S. Appl. No. 10/721,144.
Final Office Action dated Jan. 11, 2006 in U.S. Appl. No. 10/721,144.
Office Action dated Jun. 14, 2006 in U.S. Appl. No. 10/721,144.
Office Action dated Oct. 4, 2005 in U.S. Appl. No. 10/721,144.
Office Action dated Apr. 6, 2007 in U.S. Appl. No. 10/874,828, now U.S. Pat. No. 7,468,276.
Office Action dated Dec. 13, 2007 in U.S. Appl. No. 10/874,828, now U.S. Pat. No. 7,468,276.
Office Action dated Jun. 12, 2006 in U.S. Appl. No. 10/874,828, now U.S. Pat. No. 7,468,276.
Office Action dated Apr. 20, 2007 in U.S. Appl. No. 11/187,400.
Office Action dated Jan. 4, 2008 in U.S. Appl. No. 11/187,400.
Final Office Action dated Oct. 27, 2009 in U.S. Appl. No. 11/648,813.
Office Action dated Jan. 26, 2009 in U.S. Appl. No. 11/648,813.
Office Action dated Jun. 2, 2008 in U.S. Appl. No. 10/511,354.
Advisory Action dated Nov. 14, 2008 in U.S. Appl. No. 10/511,354.
Office Action dated Dec. 5, 2007 in U.S. Appl. No. 10/511,354.
Office Action dated Feb. 17, 2009 in U.S. Appl. No. 10/511,354.
Advisory Action dated Jan. 29, 2007 in U.S. Appl. No. 10/511,355.
Office Action dated Aug. 4, 2006 in U.S. Appl. No. 10/511,355.
Office Action dated Dec. 6, 2005 in U.S. Appl. No. 10/511,355.
Office Action dated Sep. 5, 2007 in U.S. Appl. No. 10/511,355.
Non Final Rejection dated Feb. 4, 2009 in U.S. Appl. No. 11/592,544.
Alviano, et al., "Term amniotic membrane is a high throughput source for multipotent mesenchymal stem cells with the ability to differentiate into endothelial cells in vitro," BMC Developmental Biology, vol. 7, No. 1, Feb. 2007.
Parolini, et al., "Concise Review: Isolation and Characterization of Cells from Human Term Placenta: Outcome of the First International Workshop on Placenta Derived Stem Cells," Stem Cells 26:300-311 (2008).
Sudo et al., "Mesenchymal progenitors able to differentiate into osteogenic, chondrogenic, and/or adipogenic cells in vitro are present in most primary fibroblast-like cell populations," Stem Cells 25:1610-1617 (2007).

* cited by examiner

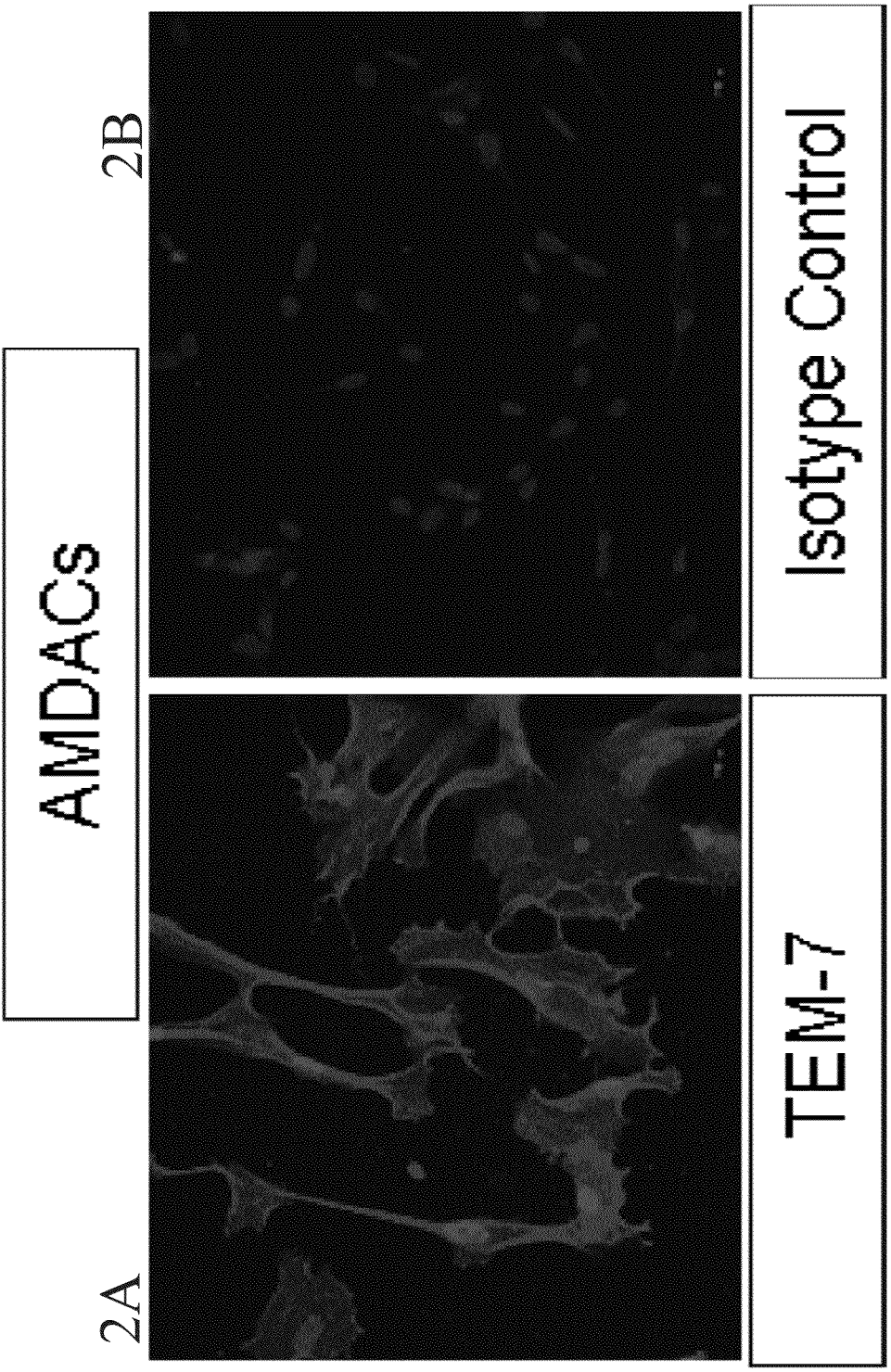
FIG. 2A-B

AMNION DERIVED ADHERENT CELLS

This application is a continuation of U.S. patent application Ser. No. 12/622,352, filed Nov. 19, 2009, now U.S. Pat. No. 8,367,409, which claims benefit of U.S. Provisional Patent Application No. 61/116,248, filed Nov. 19, 2008, the disclosures of each of which are incorporated herein by reference in their entirety.

1. FIELD

Provided herein are novel angiogenic cells from amnion, and populations of such cells, referred to herein as "amnion derived adherent cells" (AMDACs). Amnion derived adherent cells are distinct from previously-described placental stem cells, including tissue culture plastic adherent placental stem cells.

2. BACKGROUND

Cell compositions, e.g., stem cell compositions, have become an attractive therapy for a number of physiological deficiencies, e.g., bone marrow replacement. A need exists for additional populations of cells, e.g., stem cells or progenitor cells that have angiogenic potential and/or properties.

3. SUMMARY

In one aspect, provided herein is an isolated amnion derived adherent cell, also referred to herein as an AMDAC, wherein said cell is adherent to tissue culture plastic, and wherein said cell is OCT-4$^-$ (negative for OCT-4, also known as POU5F1 or octamer binding protein 4), or as determined by reverse transcriptase-polymerase chain reaction (RT-PCR), e.g., as compared to an appropriate control cell line, such as an embryonal carcinoma-derived stem cell line (e.g., NTERA-2, e.g., available from the American Type Culture Collection, ATCC Number CRL-1973), as determined by RT-PCR for 30 cycles. In a specific embodiment, the cells are OCT-4$^-$, as determined by RT-PCR, and VEGFR1/Flt-1$^+$ (vascular endothelial growth factor receptor 1) and/or VEGFR2/KDR$^+$ (vascular endothelial growth factor receptor 2, also known as kinase insert domain receptor), as determined by immunolocalization. In another specific embodiment, the cells are OCT-4$^-$, as determined by RT-PCR, and CD49f$^+$ (integrin-α6$^+$), as determined by immunolocalization. In a specific embodiment, said cell is OCT-4$^-$, as determined by RT-PCR, and HLA-G$^-$, as determined by RT-PCR. In another specific embodiment, said cell is OCT-4$^-$, as determined by RT-PCR, and CD90$^+$, CD105$^+$, or CD117$^-$ as determined by immunolocalization. In a more specific embodiment, said OCT-4$^-$ cell is CD90$^+$, CD105$^+$, and CD117$^-$. In another specific embodiment, the cell is OCT-4$^-$, and does not express SOX2, e.g., as determined by RT-PCR for 30 cycles.

In another embodiment, said OCT-4$^-$ cell is one or more of CD29$^+$, CD73$^+$, ABC-p$^+$, and CD38$^-$, as determined by immunolocalization.

In another specific embodiment, said OCT-4$^-$ cell is additionally one or more of CD9$^+$, CD10$^+$, CD44$^+$, CD54$^+$, CD98$^+$, Tie-2$^+$ (angiopoietin receptor), TEM-7$^+$ (tumor endothelial marker 7), CD31$^-$, CD34$^-$, CD45$^-$, CD133$^-$, CD143$^-$ (angiotensin-1-converting enzyme, ACE), CD146$^-$ (melanoma cell adhesion molecule), CXCR4$^-$ (chemokine (C—X—C motif) receptor 4) as determined by immunolocalization. In a more specific embodiment, said cell is CD9$^+$, CD10$^+$, CD44$^+$, CD54$^+$, CD98$^+$, Tie-2$^+$, TEM-7$^+$, CD31$^-$, CD34$^-$, CD45$^-$, CD133$^-$, CD143$^-$, CD146$^-$, and CXCR4$^-$ as determined by immunolocalization. In another more specific embodiment, the amnion derived adherent cell provided herein is OCT-4$^-$, as determined by RT-PCR; VEGFR1/Flt-1$^+$ and/or VEGFR2/KDR$^+$, as determined by immunolocalization; and one or more, or all, of CD31$^-$, CD34$^-$, CD45$^-$, CD133$^-$, and/or Tie-2$^-$ as determined by immunolocalization. In a specific embodiment, the amnion derived adherent cell, or a population of amnion derived adherent cells, expresses at least 2 log less PCR-amplified mRNA for OCT-4 at, e.g., >20 cycles, than an NTERA-2 cell, or population of NTERA-2 cells having an equivalent number of cells. In another specific embodiment, said OCT-4$^-$ cell is additionally VE-cadherin$^-$ (CD144$^-$) as determined by immunolocalization. In another specific embodiment, said OCT-4$^-$ cell is additionally positive for CD105$^+$ and CD200$^+$ as determined by immunolocalization. In another specific embodiment, said OCT-4$^-$ cell does not express CD34 as detected by immunolocalization after exposure to 1 to 100 ng/mL VEGF (vascular endothelial growth factor) for 4 to 21 days.

In another aspect, provided herein is an isolated amnion derived adherent cell, wherein said cell is adherent to tissue culture plastic, and wherein said cell is OCT-4$^-$ and SOX-2$^-$, as determined by RT-PCR; and CD90$^+$, CD105$^+$, and CD117$^-$, as determined by flow cytometry. In a specific embodiments, the OCT-4$^-$, SOX-2$^-$ cell is additionally HLA-G$^-$ or CD271$^-$, as determined by flow cytometry. In a more specific embodiment, said cell is OCT-4$^-$ and SOX-2$^-$, as determined by RT-PCR; and CD90$^+$, CD105$^+$, CD117$^-$, CD271$^-$ and HLA-G$^-$, as determined by flow cytometry.

In another aspect, provided herein is an isolated amnion derived adherent cell, wherein said cell is adherent to tissue culture plastic, and wherein said cell is positive for CD309 (also known as VEGFR2/KDR$^+$).

In another aspect, provided herein is an isolated amnion derived adherent cell, wherein said cell is adherent to tissue culture plastic, and wherein said cell is OCT-4$^-$, as determined by RT-PCR, and one or more of VEGFR2/KDR$^+$, CD9$^+$, CD54$^+$, CD105$^+$, CD200$^+$, or VE-cadherin$^-$, as determined by immunolocalization. In a specific embodiment, said cell is OCT-4$^-$, as determined by RT-PCR at, e.g., >20 cycles, and VEGFR2/KDR$^+$, CD9$^+$, CD54$^+$, CD105$^+$, CD200$^+$, and VE-cadherin$^-$, as determined by immunolocalization. In another specific embodiment, the cell does not express CD34, as detected by immunolocalization, after exposure to 1 to 100 ng/mL VEGF for 4 to 21 days.

In another embodiment, the amnion derived adherent cell is OCT-4$^-$, CD49f$^+$, HLA-G$^-$, CD90$^+$, CD105$^+$, and CD117$^-$. In a more specific embodiment, said cell is one or more of CD9$^+$, CD10$^+$, CD44$^+$, CD54$^+$, CD98$^+$, Tie-2$^+$, TEM-7$^+$, CD31$^-$, CD34$^-$, CD45$^-$, CD133$^-$, CD143$^-$, CD146$^-$ (melanoma cell adhesion molecule), or CXCR4$^-$, as determined by immunolocalization or flow cytometry. In a more specific embodiment, said cell is CD9$^+$, CD10$^+$, CD44$^+$, CD54$^+$, CD98$^+$, Tie-2$^+$, TEM-7$^+$, CD31$^-$, CD34$^-$, CD45$^-$, CD133$^-$, CD143$^-$, CD146$^-$, and CXCR4$^-$ as determined by immunolocalization. In another specific embodiment, said cell is additionally VEGFR1/Flt-1$^+$ and/or VEGFR2/KDR$^+$, as determined by immunolocalization; and one or more of CD31$^-$, CD34$^-$, CD45$^-$, CD133$^-$, and/or Tie-2$^-$ as determined by immunolocalization. In another specific embodiment, said cell is additionally VEGFR1/Flt-1$^+$, VEGFR2/KDR$^+$, CD31$^-$, CD34$^-$, CD45$^-$, CD133$^-$, and Tie-2$^-$ as determined by immunolocalization.

In another embodiment, provided herein is an isolated amnion derived adherent cell, wherein said cell does not express mRNA for FGF4, IFNG, CXCL10, ANGPT4, ANGPTL3, FGA, LEP, PRL, PROK1, TNMD, FLT3, XLKD1, CDH5, LECT1, PLG, TERT, SOX2, NANOG, MMP-13, DLX5, or BGLAP, as determined by RT-PCR, e.g., for 30 cycles. In another embodiment, provided herein is an isolated amnion derived adherent cell, wherein said cell does not constitutively express one or more of invariant chain, HLA-DR-DP-DQ, CD6, CD271, as determined by flow cytometry.

Further provided herein is an isolated population of cells comprising an amnion derived adherent cell. In a specific embodiment, at least about 50%, 60%, 70%, 80%, 90%, 95%, 98% or 99% of cells in said population are amnion derived adherent cells. In one embodiment, said cell is OCT-4⁻, as determined by RT-PCR, and VEGFR1/Flt-1⁺ and/or VEGFR2/KDR⁺ as determined by immunolocalization, and wherein said isolated population of cells is not an amnion. In another embodiment, provided herein is an isolated population of cells comprising an amnion derived adherent cell that is OCT-4⁻ and HLA-G⁻, as determined by RT-PCR, and VEGFR1/Flt-1⁺ or VEGFR2/KDR⁺ as determined by immunolocalization; and wherein said isolated population of cells is not an amnion. In a specific embodiment, at least about 50%, 60%, 70%, 80%, 90%, 95%, 98% or 99% of cells in said population are said amnion derived adherent cells. In another embodiment, provided herein is an isolated population of cells comprising an amnion derived adherent cell, wherein said cell is adherent to tissue culture plastic, wherein said cell is OCT-4⁻, as determined by RT-PCR, VEGFR1/Flt-1⁺ and VEGFR2/KDR⁺ as determined by immunolocalization, wherein said cell is additionally one or more of CD9⁺, CD10⁺, CD44⁺, CD54⁺, CD98⁺, Tie-2⁺, TEM-7⁺, CD31⁻, CD34⁻, CD45⁻, CD133⁻, CD143⁻, CD146⁻, or CXCR4⁻, as determined by immunolocalization, or HLA-G⁻ as determined by RT-PCR for, e.g., >20 cycles, and wherein said isolated population of cells is not an amnion. In a specific embodiment, at least about 50%, 60%, 70%, 80%, 90%, 95%, 98% or 99% of cells in said population are said amnion derived adherent cells. In another embodiment, provided herein is an isolated population of cells comprising an amnion derived adherent cell, wherein said cell is adherent to tissue culture plastic, wherein said cell is OCT-4⁻, as determined by RT-PCR, VEGFR1/Flt-1⁺ and/or VEGFR2/KDR⁺ as determined by immunolocalization, wherein said cell does not express CD34 as detected by immunolocalization after exposure to 1 to 100 ng/mL VEGF for 4 to 21 days, and wherein said isolated population of cells is not an amnion. In a specific embodiment, at least about 50%, 60%, 70%, 80%, 90%, 95%, 98% or 99% of cells in said population are said amnion derived adherent cells. In another embodiment, any of the above populations of cells comprising amnion derived adherent cells forms sprouts or tube-like structures when cultured in the presence of angiogenic factors such as vascular endothelial growth factor (VEGF), epithelial growth factor (EGF), platelet derived growth factor (PDGF) or basic fibroblast growth factor (bFGF), e.g., on a substrate such as MATRIGEL™.

In another embodiment, provided herein is a population of cells, wherein at least about 50%, 60%, 70%, 80%, 90%, 95% or 98% of cells in said isolated population of cells are amnion derived adherent cells that are OCT-4⁻, as determined by RT-PCR, and positive for VEGFR2/KDR, CD9, CD54, CD105, or CD200. In a specific embodiment, at least about 50%, 60%, 70%, 80%, 90%, 95% or 98% of cells in said isolated population of cells are amnion derived adherent cells that are OCT-4⁻, as determined by RT-PCR, and VEGFR2/KDR⁺, CD9⁺, CD54⁺, CD105⁺, and CD200⁺, as determined by immunolocalization. In a more specific embodiment, said amnion derived adherent cells do not express CD34, as detected by immunolocalization, after exposure to 1 to 100 ng/mL VEGF for 4 to 21 days. In a specific embodiment, said amnion derived adherent cells are adherent to tissue culture plastic. In another specific embodiment, said population of cells forms sprouts or tube-like structures when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another embodiment, provided herein is a population of cells, e.g., human cells, wherein at least about 50%, 60%, 70%, 80%, 90%, 95% or 98% of cells in said isolated population of cells are amnion derived adherent cells that express RNA for one or more, or all, of ACTA2, ADAMTS1, AMOT, ANG, ANGPT1, ANGPT2, ANGPTL1, ANGPTL2, ANGPTL4, BAI1, CD44, CD200, CEACAM1, CHGA, COL15A1, COL18A1, COL4A1, COL4A2, COL4A3, CSF3, CTGF, CXCL12, CXCL2, DNMT3B, ECGF1, EDG1, EDIL3, ENPP2, EPHB2, FBLN5, F2, FGF1, FGF2, FIGF, FLT4, FN1, FST, FOXC2, GRN, HGF, HEY1, HSPG2, IFNB1, IL8, IL12A, ITGA4, ITGAV, ITGB3, MDK, MMP2, MYOZ2, NRP1, NRP2, PDGFB, PDGFRA, PDGFRB, PECAM1, PF4, PGK1, PROX1, PTN, SEMA3F, SERPINB5, SERPINC1, SERPINF1, TIMP2, TIMP3, TGFA, TGFB1, THBS1, THBS2, TIE1, TIE2/TEK, TNF, TNNI1, TNFSF15, VASH1, VEGF, VEGFB, VEGFC, VEGFR1/FLT1, or VEGFR2/KDR.

In another embodiment, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that express one or more of, or all of, CD49d, Connexin-43, HLA-ABC, Beta 2-microglobulin, CD349, CD318, PDL1, CD106, Galectin-1, ADAM 17 precursor (A disintegrin and metalloproteinase domain 17) (TNF-alpha converting enzyme) (TNF-alpha convertase), Angiotensinogen precursor, Filamin A (Alpha-filamin) (Filamin 1) (Endothelial actin-binding protein) (ABP-280) (Nonmuscle filamin), Alpha-actinin 1 (Alpha-actinin cytoskeletal isoform) (Non-muscle alpha-actinin 1) (F-actin cross linking protein), Low-density lipoprotein receptor-related protein 2 precursor (Megalin) (Glycoprotein 330) (gp330), Macrophage scavenger receptor types I and II (Macrophage acetylated LDL receptor I and II), Activin receptor type IIB precursor (ACTR-IIB), Wnt-9 protein, Glial fibrillary acidic protein, astrocyte (GFAP), Myosin-binding protein C, cardiac-type (Cardiac MyBP-C) (C-protein, cardiac muscle isoform), or Myosin heavy chain, nonmuscle type A (Cellular myosin heavy chain, type A) (Nonmuscle myosin heavy chain-A) (NMMHC-A).

In another aspect, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that secrete one or more, or all, of VEGF, HGF, IL-8, MCP-3, FGF2, follistatin, G-CSF, EGF, ENA-78, GRO, IL-6, MCP-1, PDGF-BB, TIMP-2, uPAR, or galectin-1, e.g., into culture medium in which the cell, or cells, are grown.

In another embodiment, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that express angiogenic micro RNAs (miRNAs) at a higher level than bone marrow-derived mesenchymal stem cells, wherein said miR- NAs comprise one or more, or all of, miR-17-3p, miR-18a, miR-18b, miR-19b, miR-92, and/or miR-296. In another embodiment, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that express one or more of, or all of, angiogenic micro RNAs (miRNAs) at a lower level than bone marrow-derived mesenchymal stem cells, wherein said miRNAs comprise one or more, or all of, miR-20a, miR-20b, miR-221, miR-222, miR-15b, and/or miR-16. In certain embodiments, AMDACs, or populations of AMDACs, express one or more, or all, the angiogenic miRNAs miR-17-3p, miR-18a, miR-18b, miR-19b, miR-92, miR-20a, miR-20b, miR-296, miR-221, miR-222, miR-15b, and/or miR-16.

In another specific embodiment, provided herein is an amnion derived angiogenic cell, or population of amnion derived angiogenic cells, that express increased levels of CD202b, IL-8 and/or VEGF under hypoxic conditions (e.g., less than about 5% $O_2$) compared to normoxic conditions (e.g., about 20% or about 21% $O_2$).

In another specific embodiment, the isolated population of amnion derived adherent cells additionally comprises a second type of cell. In specific embodiments, the AMDACs comprise at least 10%, 15%, 20%, 25%, 30%, 35%, 40%, 45%, 50%, 55%, 60%, 65%, 70%, 80%, 85%, 90%, 95% or at least 98% of cells in said population. In a specific embodiment, the second type of cell is contained within or isolated from placental blood, umbilical cord blood, crude bone marrow or other tissues. In a more specific embodiment, said second type of cell is embryonic stem cell, a blood cell, a stem cell isolated from peripheral blood, a stem cell isolated from placental blood, a stem cell isolated from placental perfusate, a stem cell isolated from placental tissue, a stem cell isolated from umbilical cord blood, an umbilical cord stem cell, a bone marrow-derived mesenchymal stem cell, a mesenchymal stromal cell, a hematopoietic stem cell, a somatic stem cell, a chondrocyte, a fibroblast, a muscle cell, an endothelial cell, an endothelial progenitor cell, a pericyte, a myocyte, a cardiomyocyte, a myoblast, an angioblast, or a cardiomyoblast. In another specific embodiment, said second type of cell is a hematopoietic stem or progenitor cell, e.g., a $CD34^+$ cell. In another more specific embodiment, said second type of cell comprises at least 10%, 15%, 20%, 25%, 30%, 35%, 40%, 45%, 50%, 55%, 60%, 65%, 70%, 80%, 85%, 90%, 95% or at least 98% of cells in said population.

In another specific embodiment, any of the above cells are, or have been, proliferated in culture. In another specific embodiment, any of the above cells is from a culture of said cells that has been passaged at least 1, 2, 3, 4, 5, 6, 7, 8, 9, 10, 11, 12, 13, 14, 15, 16, 17, 18, 19, or 20 times, or more. In another specific embodiment, any of the above cells is from a culture that has doubled in culture at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 times, or more.

In another aspect, provided herein is a composition, e.g., a pharmaceutical composition, comprising any of the amnion derived adherent cells, or populations of cells comprising the amnion derived adherent cells, provided herein. In a specific embodiment, the composition is a matrix or scaffold, e.g., a natural tissue matrix or scaffold, for example, a permanent or degradable decellularized tissue matrix or scaffold; or synthetic matrix or scaffold. In a more specific embodiment, said matrix or scaffold is shaped in the form of a tube or other three-dimensional form of an organoid. In another more specific embodiment, said matrix is a decellularized tissue matrix. In another specific embodiment, the composition comprises one or more of the isolated amnion derived adherent cells provided herein, or population of cells comprising the amnion derived adherent cells, in a physiologically-acceptable solution, e.g., a saline solution, culture medium or the like.

In another aspect, provided herein is a method of treating an individual having a disease or disorder of the circulatory system, comprising administering one or more of the amnion derived adherent cells described herein to said individual in an amount and for a time sufficient for detectable improvement of one or more symptoms of said disease or disorder. In another embodiment, provided herein is a method of treating an individual having a disease or disorder of the circulatory system, comprising administering amnion derived adherent cells to said individual in an amount and for a time sufficient for detectable improvement of one or more indicia of cardiac function, wherein said indicia of cardiac function are chest cardiac output (CO), cardiac index (CI), pulmonary artery wedge pressure (PAWP), cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (dP/dt), a decrease in atrial or ventricular functioning, an increase in pumping efficiency, a decrease in the rate of loss of pumping efficiency, a decrease in loss of hemodynamic functioning, or decrease in complications associated with cardiomyopathy, as compared to the individual prior to administration of amnion derived adherent cells.

In a specific embodiment, said disease or disorder is myocardial infarction. In another specific embodiment, said disease or disorder is cardiomyopathy. In other specific embodiments, said disease or disorder is aneurysm, angina, aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, carditis, carotid artery disease, coarctation of the aorta, congenital heart defects, congestive heart failure, coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocarditis, paroxysmal atrial tachycardia (PAT), periarteritis nodosa (polyarteritis, polyarteritis nodosa), pericarditis, peripheral vascular disease, critical limb ischemia, phlebitis, pulmonary valve stenosis (pulmonic stenosis), Raynaud's Disease, renal artery stenosis, renovascular hypertension, rheumatic heart disease, diabetic vasculopathy, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, endocardial cushion defect, acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and sub-acute), angina pectoris, acute pulmonary heart disease, pulmonary embolism, chronic pulmonary heart disease, kyphoscoliotic heart disease, myocarditis, endocarditis, endomyocardial fibrosis, endocardial fibroelastosis, atrioventricular block, cardiac dysrhythmias, myocardial degeneration, cerebrovascular disease, a disease of arteries, arterioles and capillaries, or a disease of veins and lymphatic vessels.

In other specific embodiments, said disease or disorder is an occlusion and stenosis of precerebral arteries, or occlusion of cerebral arteries. In one aspect, provided herein is a method of treating an individual who has a disruption of the flow of blood in or around the individual's brain, e.g., who has a symptom or neurological deficit attributable to a disruption of the flow of blood in or around the individual's brain or central nervous system (CNS), comprising administering to said individual a therapeutically effective amount of isolated AMDACs. In certain embodiments, the disruption of flow of blood results in anoxic injury or hypoxic injury to the individual's brain or CNS.

In other specific embodiments, said disease or disorder is an occlusion and stenosis of peripheral arteries. In one aspect, provided herein is a method of treating an individual who has a disruption of the flow of blood in or around limb, e.g., who has a symptom or vascular deficit attributable to a disruption of the flow of blood in or around the individual's peripheral vascular system, comprising administering to said individual a therapeutically effective amount of isolated AMDACs. In certain embodiments, the disruption of flow of blood results in anoxic injury or hypoxic injury to the individual's limbs and or extremities.

In another aspect, provided herein is a method of treating an individual suffering from a wound or trauma, comprising administering one or more of the amnion derived adherent cells described herein to said individual in an amount and for a time sufficient for detectable improvement of said wound or trauma.

In another specific embodiment of the method of treatment, said cells are administered to said individual by injection. In a more specific embodiment, said injection is injection into an ischemic area of the individual's heart. In another specific embodiment of the method of treatment, said cells are administered to said individual by intravenous infusion. In another specific embodiment of the method of treatment, said cells, or a population of said cells, or a population of cells comprising said cells, is administered to said individual by implantation in said individual of a matrix or scaffold comprising amnion derived adherent cells, as described above.

The isolated amnion derived adherent cells and cell populations provided herein are not the isolated placental stem cells or cell populations described, e.g., in U.S. Pat. No. 7,255,879 or U.S. Patent Application Publication No. 2007/0275362. The isolated amnion derived adherent cells provided herein are also not endothelial progenitor cells, amniotic epithelial cells, trophoblasts, cytotrophoblasts, embryonic germ cells, embryonic stem cells, cells obtained from the inner cell mass of an embryo, or cells obtained from the gonadal ridge of an embryo.

As used herein, the term "about" means, e.g., within 10% of a stated figure or value.

As used herein, the term "angiogenic," in reference to the amnion derived adherent cells described herein, means that the cells can form vessels or vessel-like sprouts, or that the cells can promote angiogenesis (e.g., the formation of vessels or vessel-like structures) in another population of cells, e.g., endothelial cells.

As used herein, the term "angiogenesis" refers to the process of blood vessel formation that includes, but is not limited to, endothelial cell activation, migration, proliferation, matrix remodeling and cell stabilization.

As used herein, the term "stem cell" defines the functional properties of any given cell population that can proliferate extensively, but not necessarily infinitely, and contribute to the formation of multiple tissues, either during embryological development or post-natal tissue replacement and repair.

As used herein, the term "progenitor cell" defines the functional properties of any given cell population that can proliferate extensively, but not necessarily infinitely, and contribute to the formation of a restricted set of multiple tissues in comparison to a stem cell, either during embryological development or post-natal tissue replacement and repair.

As used herein, the term "derived" means isolated from or otherwise purified. For example, amnion derived adherent cells are isolated from amnion. The term "derived" encompasses cells that are cultured from cells isolated directly from a tissue, e.g., the amnion, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "isolated cell" means a cell that is substantially separated from other, cells of the tissue, e.g., amnion or placenta, from which the cell is derived. A cell is "isolated" if at least about 20%, 30%, 40%, 50%, 60%, 70%, 80%, 90%, 95%, or at least 99% of the cells with which the stem cell is naturally associated are removed from the cell, e.g., during collection and/or culture of the cell.

As used herein, the term "isolated population of cells" means a population of cells that is substantially separated from other cells of the tissue, e.g., amnion or placenta, from which the population of cells is derived. A cell is "isolated" if at least about 20%, 30%, 40%, 50%, 60%, 70%, 80%, 90%, 95%, or at least 99% of the cells with which the population of cells, or cells from which the population of cells is derived, is naturally associated are removed from the cell, e.g., during collection and/or culture of amnion derived adherent cells.

As used herein, a cell is "positive" for a particular marker when that marker is detectable above background, e.g., by immunolocalization, e.g., by flow cytometry; or by RT-PCR. For example, a cell is described as positive for, e.g., CD105 if CD105 is detectable on the cell in an amount detectably greater than background (in comparison to, e.g., an isotype control). In the context of, e.g., antibody-mediated detection, "positive," as an indication a particular cell surface marker is present, means that the marker is detectable using an antibody, e.g., a fluorescently-labeled antibody, specific for that marker, "positive" also means that a cell bears that marker in a amount that produces a signal, e.g., in a cytometer, that is detectably above background. For example, a cell is "CD105$^+$" where the cell is detectably labeled with an antibody specific to CD105, and the signal from the antibody is detectably higher than a control (e.g., background). Conversely, "negative" in the same context means that the cell surface marker is not detectable using an antibody specific for that marker compared to background. For example, a cell is "CD34$^-$" where the cell is not detectably labeled with an antibody specific to CD34. Unless otherwise noted herein, cluster of differentiation ("CD") markers are detected using antibodies. For example, OCT-4 can be determined to be present, and a cell is OCT-4$^+$, if mRNA for OCT-4 is detectable using RT-PCR, e.g., for 30 cycles.

4. BRIEF DESCRIPTION OF THE FIGURES

FIG. 2 shows the expression of TEM-7 on the cell surface of amnion derived adherent cells (AMDACs). 2A: Staining of AMDACs with anti-TEM-7; 2B: staining of AMDACs with isotype control.

FIG. 3 shows the secretion of selected angiogenic proteins by amnion derived adherent cells. 3A: secretion of TIMP-1, TIMP-2, thrombopoietin, VEGF, VEGF-D by amnion derived adherent cells; 3B: secretion of angiogenin, EGF, ENA-78, bFGF, GRO by amnion derived adherent cells; 3C: secretion of IFN-gamma, IGF-I, IL-6, IL-8, leptin by amnion derived adherent cells; 3D: secretion of MCP-1, PDGF-BB, PIGF, RANTES, TGF-beta 1 by amnion derived adherent cells.

Figure 4:
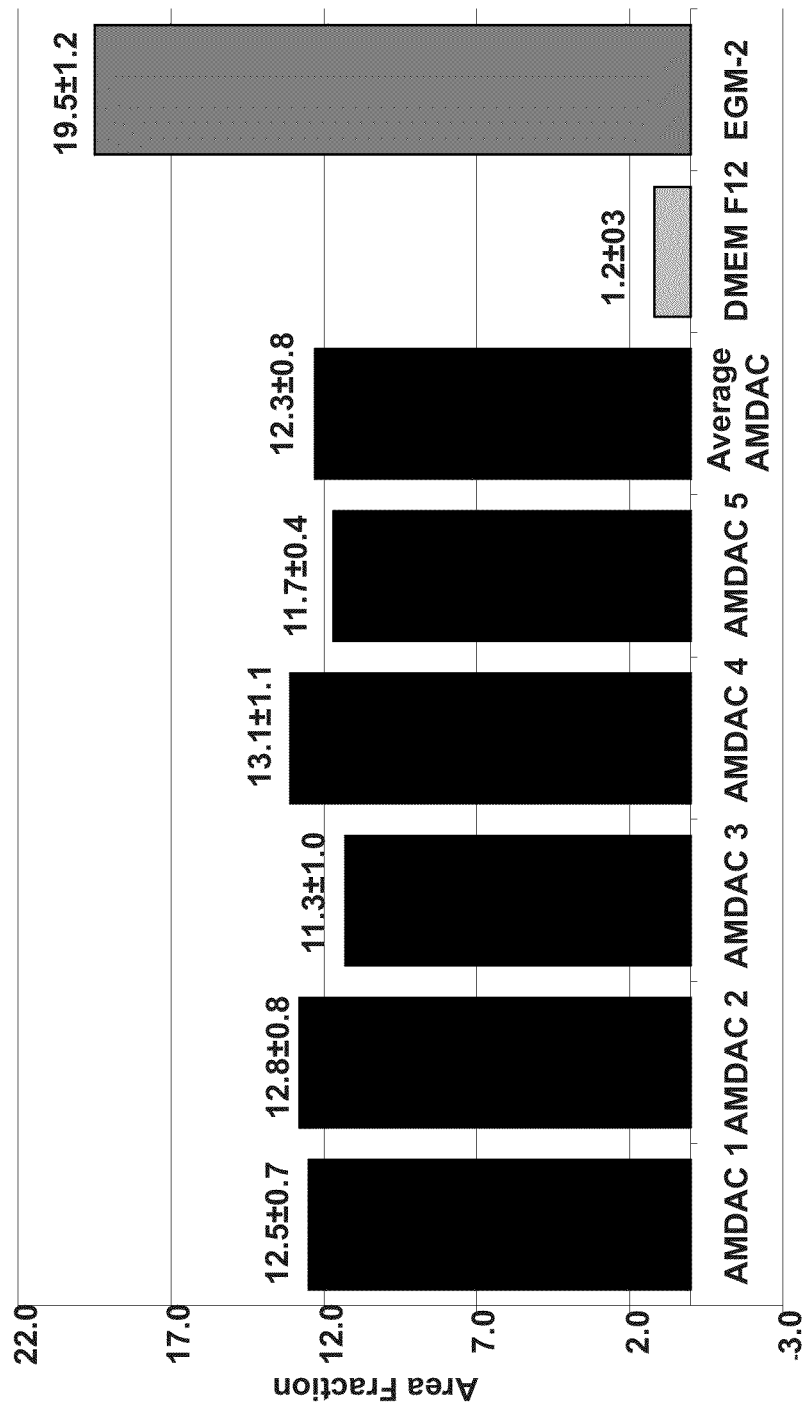

FIG. 4 shows the angiogenic effect of amnion derived adherent cells conditioned medium on Human Endothelial Cell (HUVEC) tube formation.

Figure 5:

FIG. 5 shows the angiogenic effect of amnion derived adherent cells conditioned medium on human endothelial cell migration.

Figure 6:
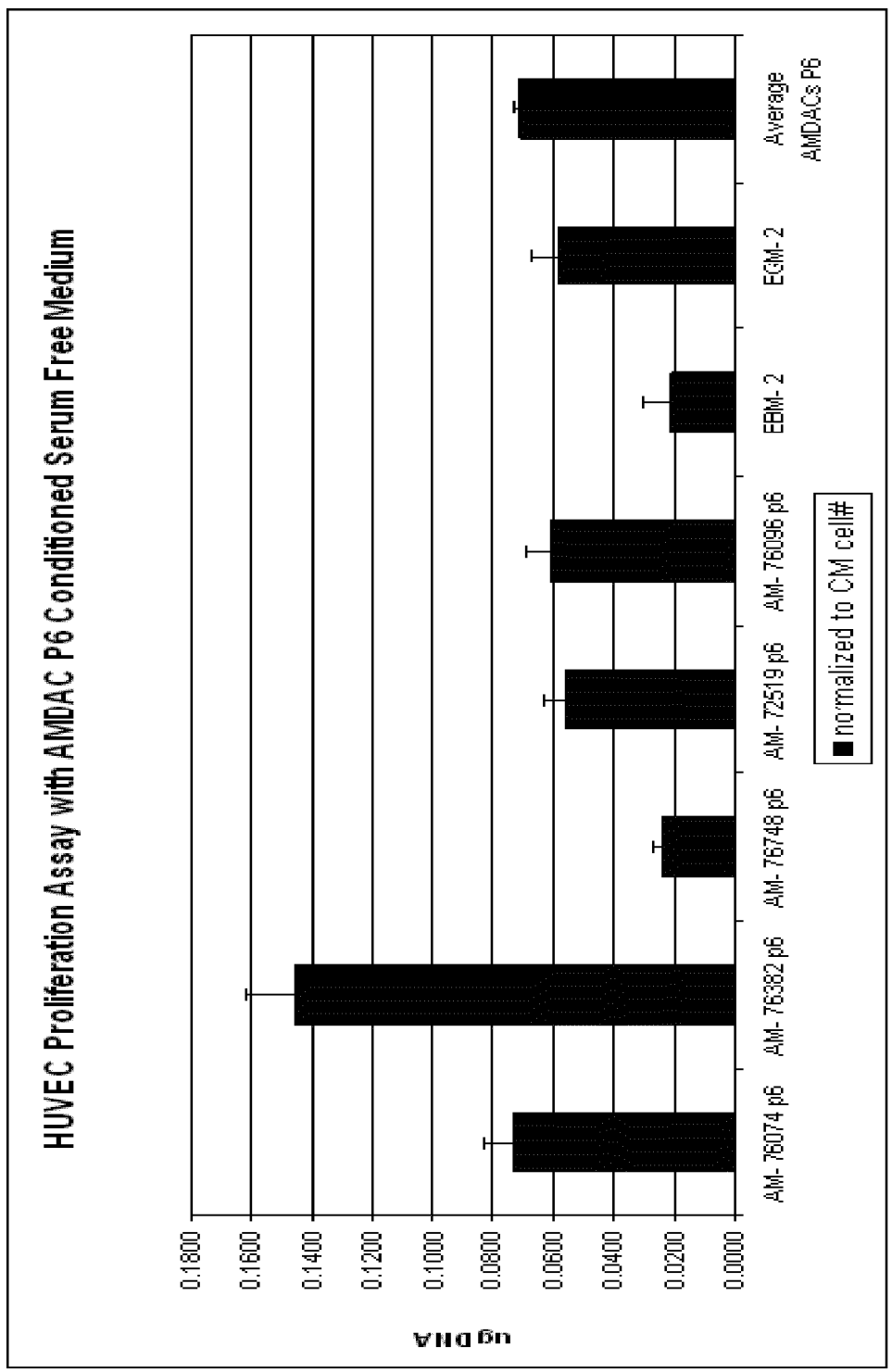

FIG. 6 shows the effect of amnion derived adherent cell-conditioned medium on Human Endothelial Cell proliferation.

Figure 7:
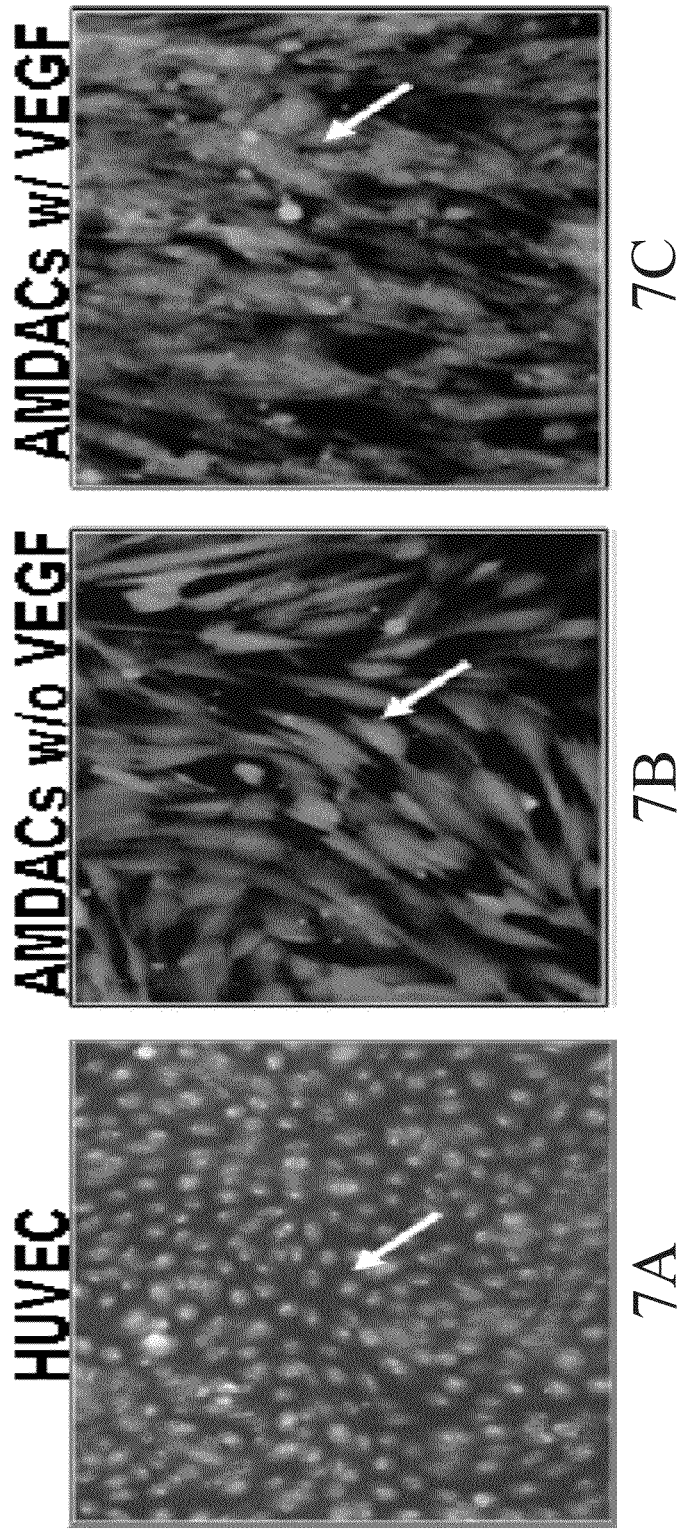

FIG. 7 shows the uptake of acetylated LDL by HUVECs (7A and amnion derived adherent cells without VEGF (7B) and with VEGF (7C).

Figure 8:
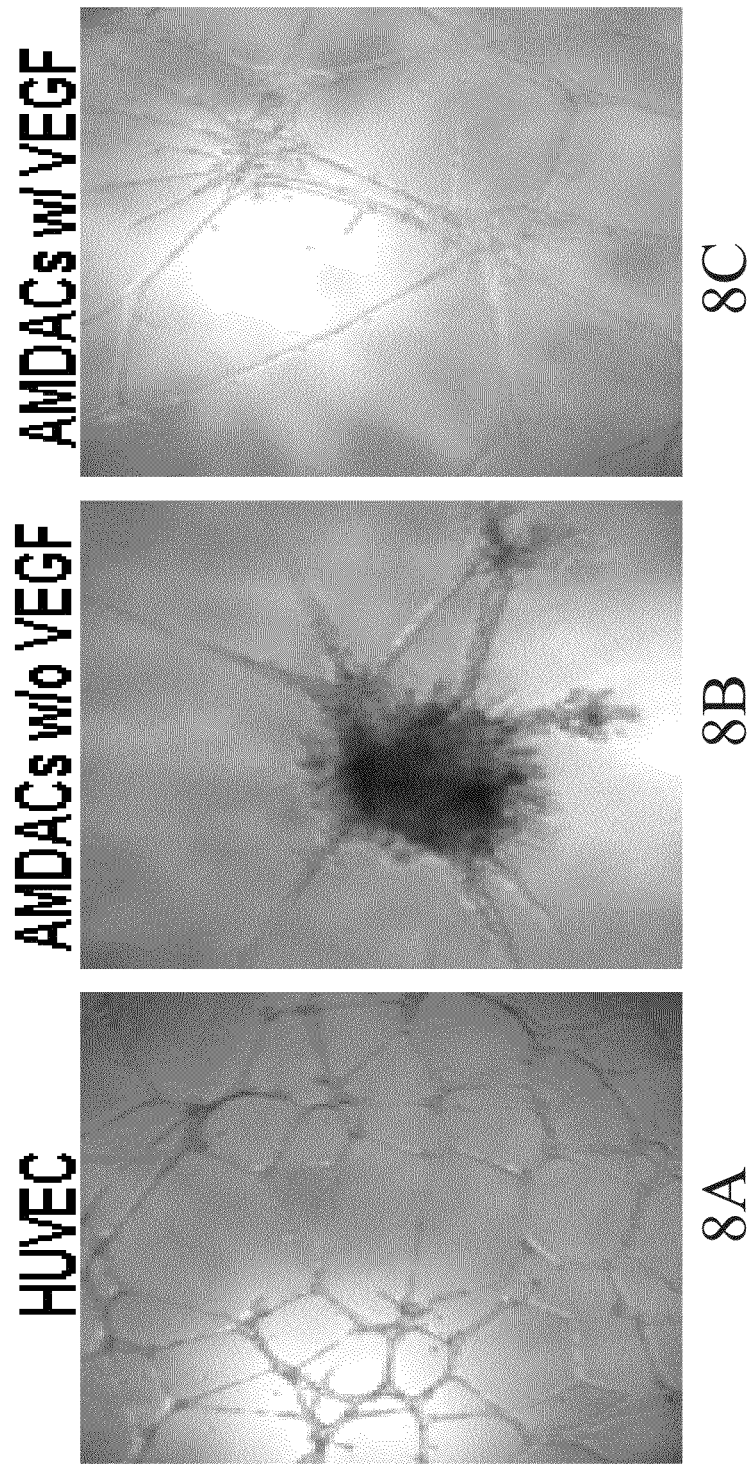

FIG. 8 shows tube formation of HUVECs (8A) and amnion derived adherent cells without VEGF (8B) and with VEGF (8C).

Figure 9:
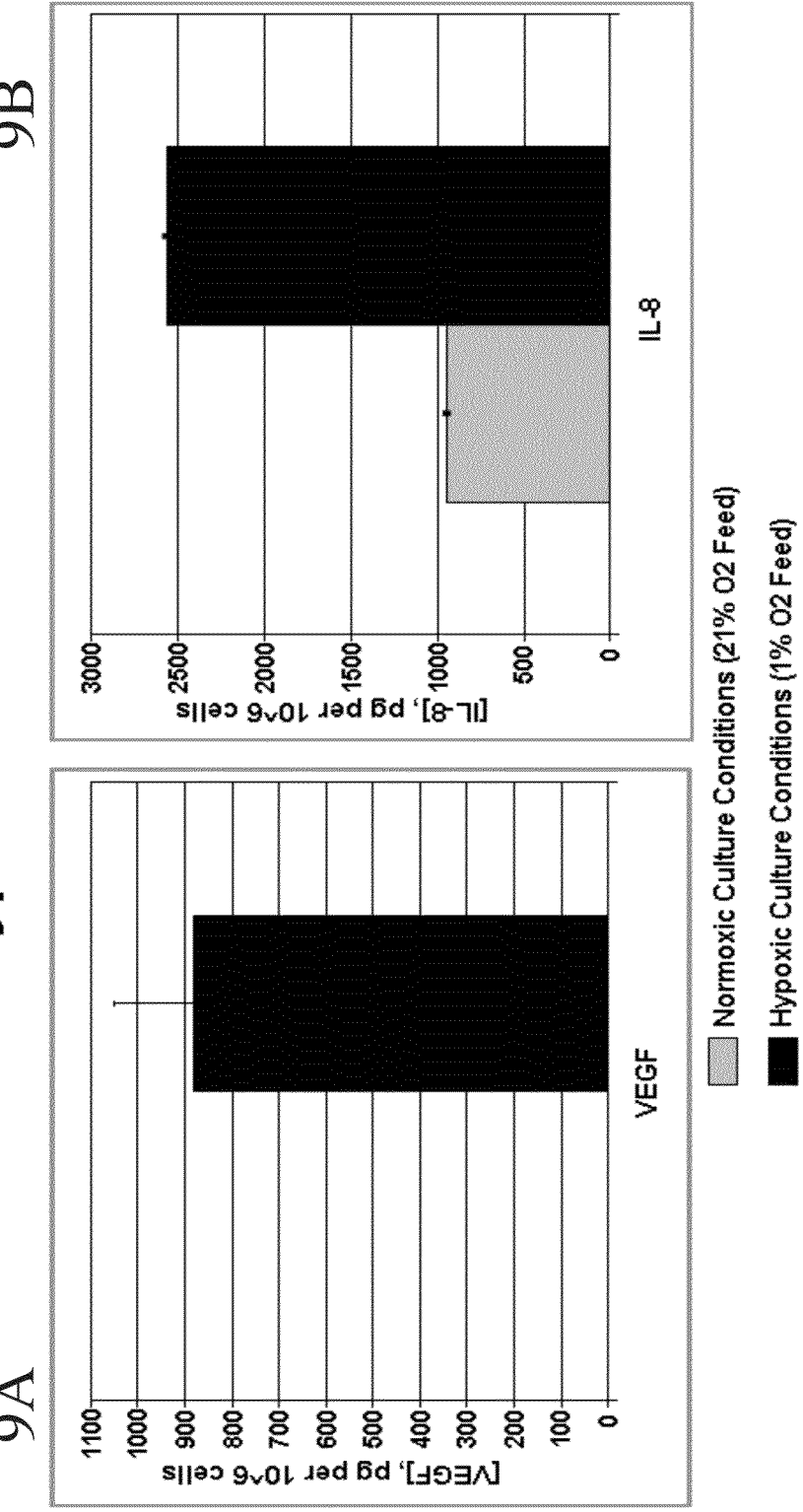

FIG. 9 shows the secretion of VEGF (9A) and IL-8 (9B) by amnion derived adherent cells under hypoxic and normoxic conditions.

Figure 10:
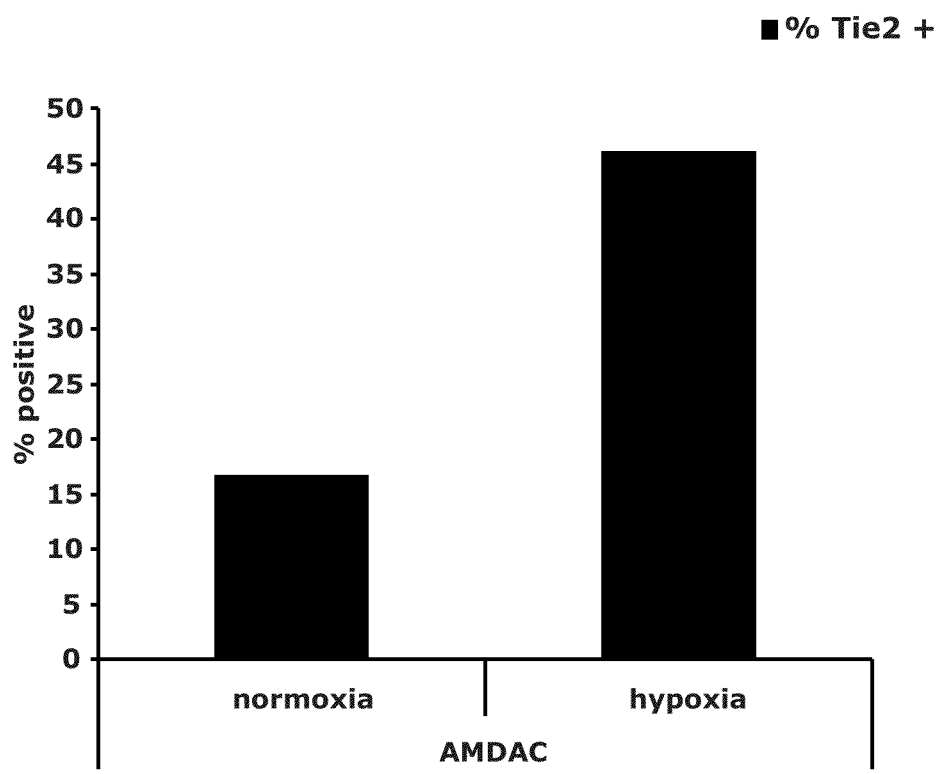

FIG. 10 shows the expression of cellular marker Tie2 under normoxic (about 21% $O_2$) and hypoxic (less than about 5% $O_2$) conditions. Y axis: percentage of cells positive for Tie2 by flow cytometry.

Figure 11:
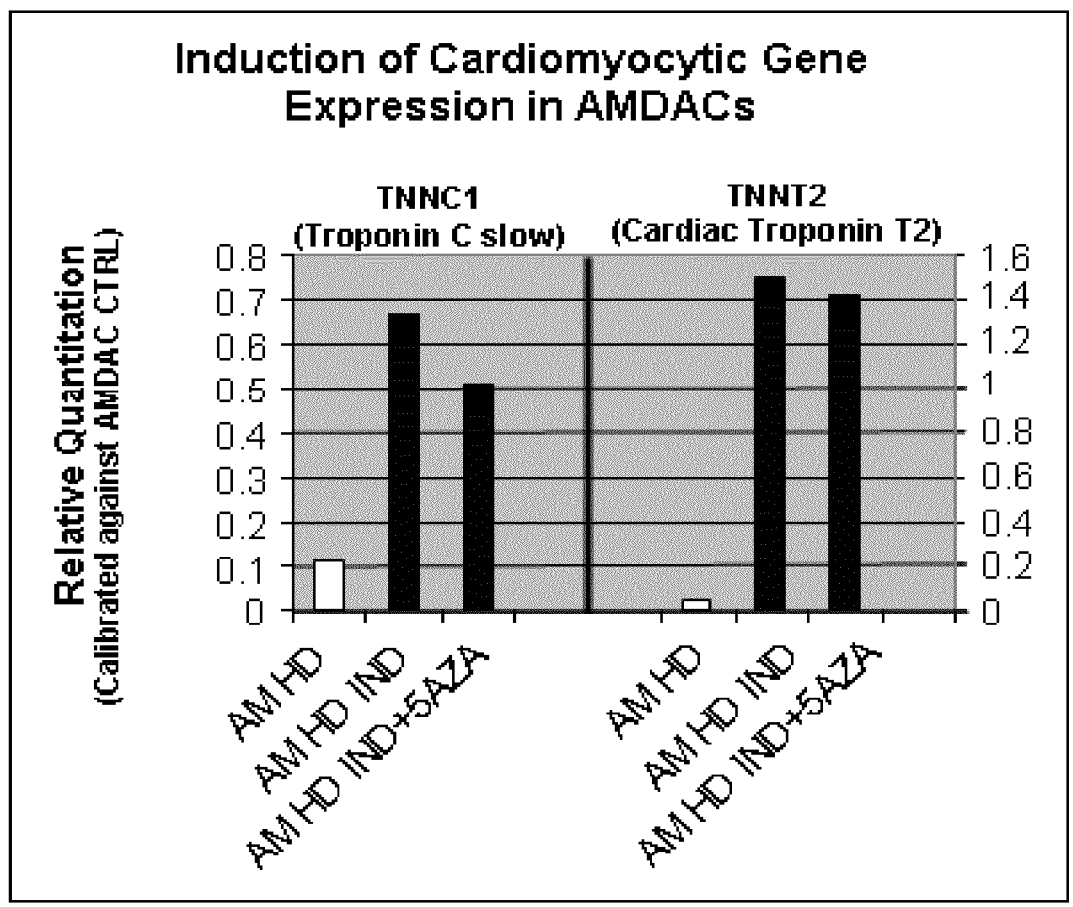

FIG. 11 shows the cardiomyocytic differentiation potency of amnion derived adherent cells, wherein AM refers to amnion derived adherent cells (AMDACs), HD refers to untreated hanging drop, HD IND refers to hanging drop exposed to inducing conditions, and HD IND+5-AZA refers to induction in the presence or absence of 5-azacytidine. CTRL refers to the untreated hanging drop control.

Figure 12:
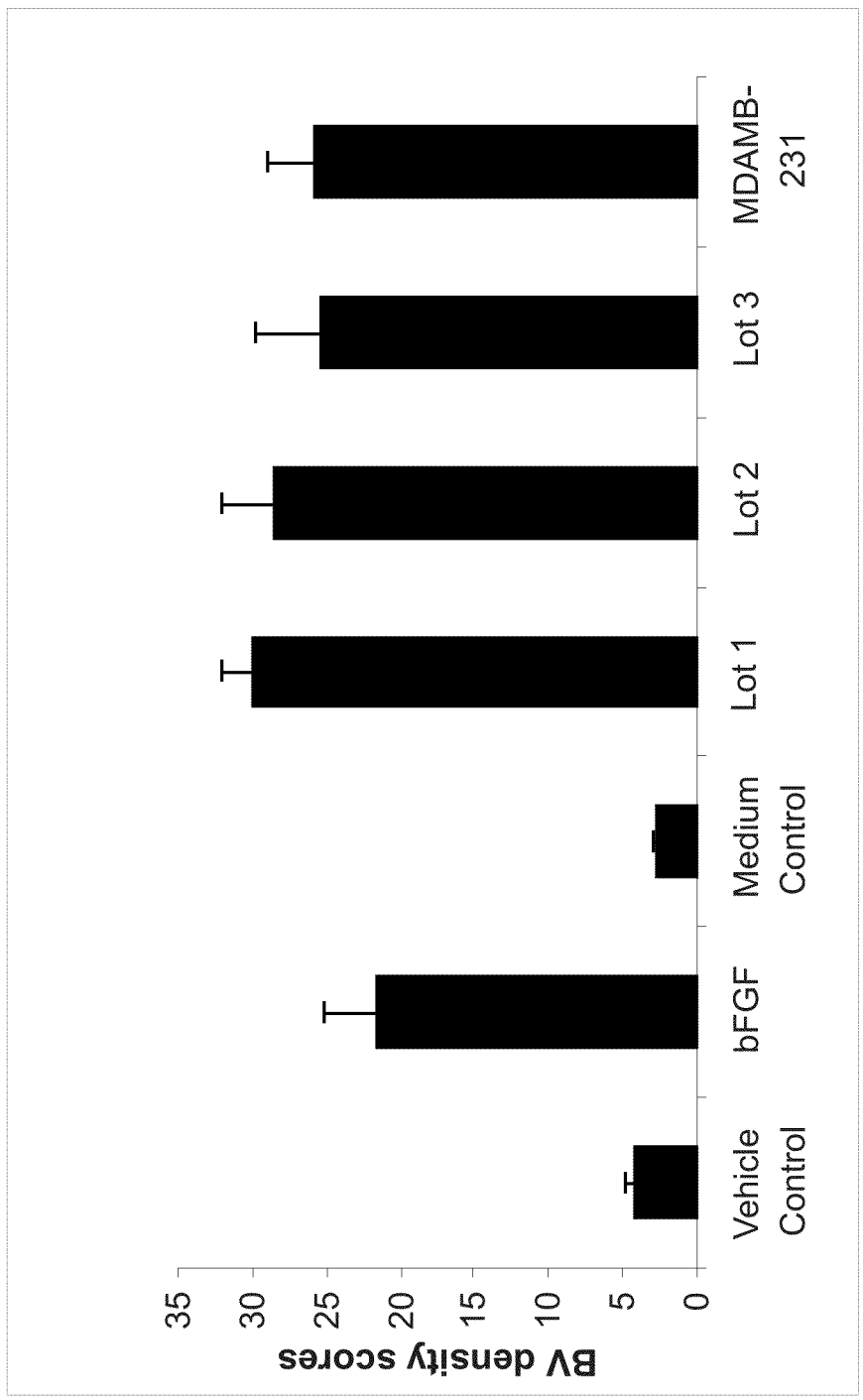

FIG. 12 shows positive effect of AMDACs on angiogenesis in a chick chorioallantois angiogenesis model. Lot 1, Lot 2, Lot 3: AMDACs from three separate cell preparations. bFGF: basic fibroblast growth factor (positive control). MDAMB231: Angiogenic breast cancer cell line (positive control). Y axis: Degree of blood vessel formation.

Figure 13:
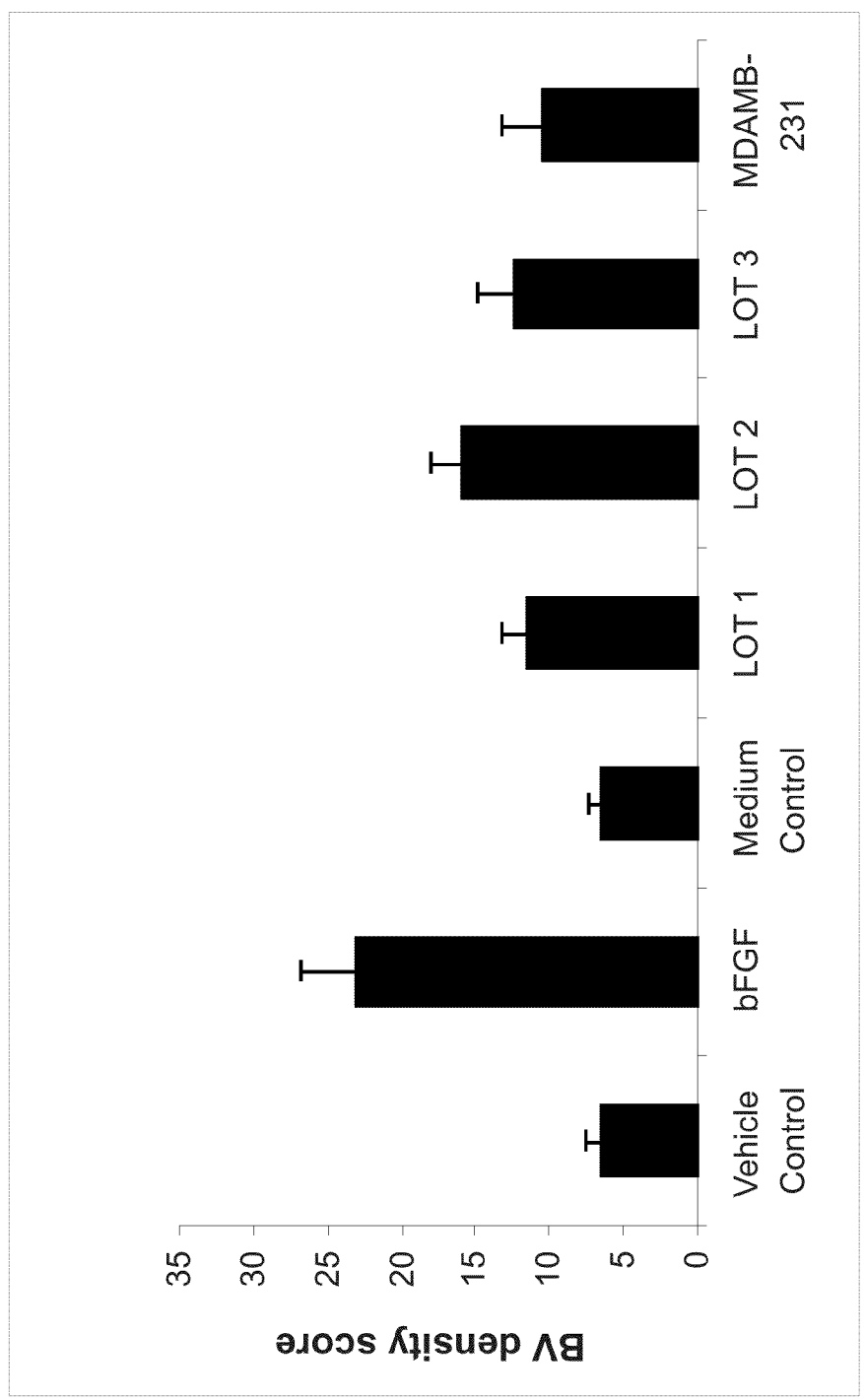

FIG. 13 shows positive effect of AMDAC-conditioned medium on angiogenesis in a chick chorioallantois angiogenesis model. Lot 1, Lot 2, Lot 3: AMDACs from three separate cell preparations. bFGF: basic fibroblast growth factor (positive control). MDAMB231: Angiogenic breast cancer cell line (positive control). Y axis: Degree of blood vessel formation.

Figure 14A:
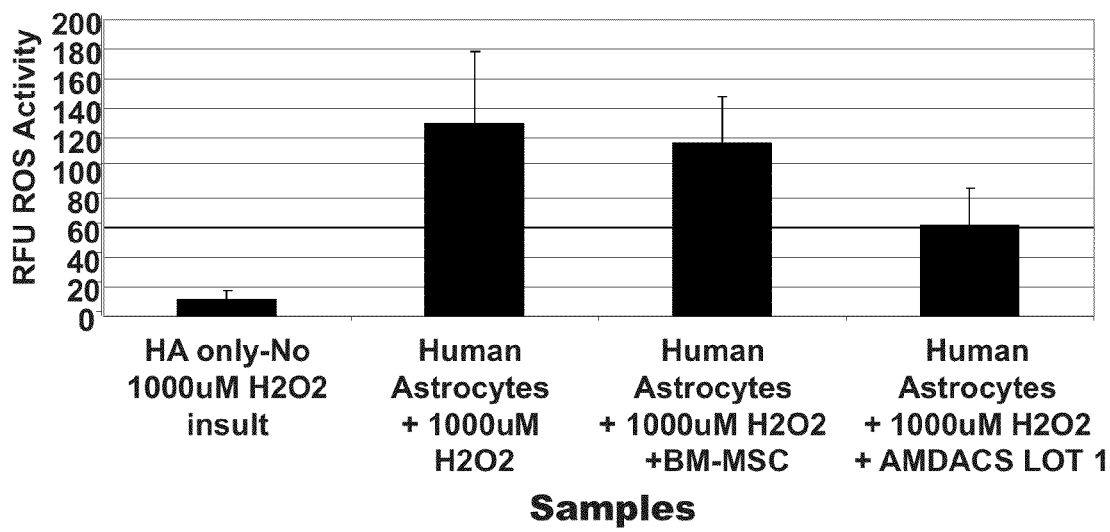
Figure 14B:
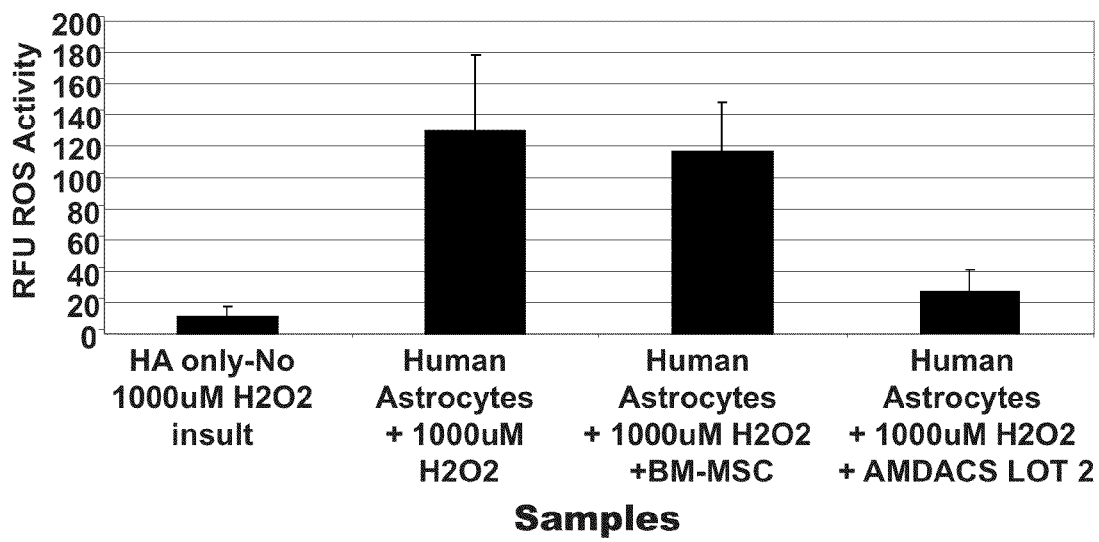

FIGS. 14A, 14B: Hydrogen peroxide-generated reactive oxygen species present in cultures of astrocytes, co-cultures of astrocytes and bone marrow-derived mesenchymal stem cells (BM-MSCs), or co-cultures of astrocytes and AMDACs. 14A: AMDACs, Lot 1; 14B: AMDACs, Lot 2. The conditions HA (human astrocytes) alone, astrocytes+$H_2O_2$, and astrocytes+BM-MSCs+$H_2O_2$ are the same for FIGS. 14A and 14B. RFU ROS activity: Relative fluorescence units for reactive oxygen species.

5. DETAILED DESCRIPTION

5.1 Characteristics of Amnion Derived Adherent Cells

Provided herein are unique adherent, angiogenic cells, and populations of such cells, isolatable from the amnion, referred to herein as "amnion derived adherent cells" or AMDACs. Amnion derived adherent cells superficially resemble mesenchymal cells in appearance, having a generally fibroblastoid shape. The cells adhere to a cell culture surface, e.g., to tissue culture plastic.

AMDACs display cellular markers that distinguish them from other amnion-derived, or placenta-derived, cells. For example, in one embodiment, the amnion derived adherent cell is OCT-4$^-$ (octamer binding protein 4), as determined by RT-PCR. In another specific embodiment, the OCT-4$^-$ amnion derived adherent cell is CD49f$^+$, as determined by immunolocalization. In another specific embodiment, said OCT-4$^-$ cell is HLA-G$^-$, as determined by RT-PCR. In another specific embodiment, the OCT-4$^-$ cell is VEGFR1/Flt-1$^+$ (vascular endothelial growth factor receptor 1) and/or VEGFR2/KDR$^+$ (vascular endothelial growth factor receptor 2), as determined by immunolocalization. In a specific embodiment, the OCT-4$^-$ amnion derived adherent cell, or a population of OCT-4$^-$ amnion derived adherent cells, expresses at least 2 log less PCR-amplified mRNA for OCT-4 at, e.g., 20 cycles, than an NTERA-2 cell, or population of NTERA-2 cells having an equivalent number of cells and RNA amplification cycles. In another specific embodiment, said OCT-4$^-$ cell is CD90$^+$, CD105$^+$, or CD117$^-$. In a more specific embodiment, said OCT-4$^-$ cell is CD90$^+$, CD105$^+$, and CD117$^-$. In a more specific embodiment, the cell is OCT-4$^-$ or HLA-G$^-$, and is additionally CD49f$^+$, CD90$^+$, CD105$^+$, and CD117$^-$. In a more specific embodiment, the cell is OCT-4$^-$, HLA-G$^-$, CD49f$^+$, CD90$^+$, CD105$^+$, and CD117$^-$. In another specific embodiment, the OCT-4$^-$ cell does not express SOX2, e.g., as determined by RT-PCR for 30 cycles. In a specific embodiment, therefore, the cell is OCT-4$^-$, CD49f$^+$, CD90$^+$, CD105$^+$, and CD117$^-$, as determined by immunolocalization or flow cytometry, and SOX2$^-$, as determined by RT-PCR, e.g., for 30 cycles.

In another embodiment, said OCT-4$^-$ cell is one or more of CD29$^+$, CD73$^+$, ABC-p$^+$, and CD38$^-$, as determined by immunolocalization.

In another specific embodiment, for example, an OCT-4$^-$ AMDAC can additionally be one or more of CD9$^+$, CD10$^+$, CD44$^+$, CD54$^+$, CD98$^+$, TEM-7$^+$ (tumor endothelial marker 7), CD31$^-$, CD34$^-$, CD45$^-$, CD133$^-$, CD143$^-$ (angiotensin-1-converting enzyme, ACE), CD146$^-$ (melanoma cell adhesion molecule), or CXCR4$^-$ (chemokine (C—X—C motif) receptor 4) as determined by immunolocalization, or HLA-G$^-$ as determined by RT-PCR. In a more specific embodiment, said cell is CD9$^+$, CD10$^+$, CD44$^+$, CD54$^+$, CD98$^+$, Tie-2$^+$, TEM-7$^+$, CD31$^-$, CD34$^-$, CD45$^-$, CD133$^-$, CD143$^-$, CD146$^-$, and CXCR4$^-$ as determined by immunolocalization, and HLA-G$^-$ as determined by RT-PCR. In one embodiment, the amnion derived adherent cell provided herein is one or more of CD31$^-$, CD34$^-$, CD45$^-$, and/or CD133$^-$. In a specific embodiment, the amnion derived adherent cell is OCT-4$^-$, as determined by RT-PCR; VEGFR1/Flt-1$^+$ and/or VEGFR2/KDR$^+$, as determined by immunolocalization; and one or more, or all, of CD31$^-$, CD34$^-$, CD45$^-$, and/or CD133$^-$.

In another specific embodiment, said cell is additionally VE-cadherin$^-$ as determined by immunolocalization. In another specific embodiment, said cell is additionally positive for CD105 and CD200+ as determined by immunolocalization. In another specific embodiment, said cell does not express CD34 as detected by immunolocalization after exposure to 1 to 100 ng/mL VEGF for 4 to 21 days. In more specific embodiments, said cell does not express CD34 as detected by immunolocalization after exposure to 25 to 75 ng/mL VEGF for 4 to 21 days, or to 50 ng/mL VEGF for 4 to 21 days. In even more specific embodiments, said cell does not express CD34 as detected by immunolocalization after exposure to 1, 2.5, 5, 10, 25, 50, 75 or 100 ng/mL VEGF for 4 to 21 days. In yet more specific embodiments, said cell does not express CD34 as detected by immunolocalization after exposure to 1 to 100 ng/mL VEGF for 7 to 14, e.g., 7, days.

In specific embodiments, the amnion derived adherent cell is OCT-4−, as determined by RT-PCR, and one or more of VE-cadherin−, VEGFR2/KDR+, CD9+, CD54+, CD105+, and/or CD200+ as determined by immunolocalization. In a specific embodiment, the amnion derived cell is OCT-4−, as determined by RT-PCR, and VE-cadherin, VEGFR2/KDR+, CD9+, CD54+, CD105+, and CD200+ as determined by immunolocalization. In another specific embodiment, said cells do not express CD34, as detected by immunolocalization, e.g., after exposure to 1 to 100 ng/mL VEGF for 4 to 21 days.

In another embodiment, the amnion derived adherent cell is OCT-4−, CD49f+, HLA-G−, CD90+, CD105+, and CD117−. In a more specific embodiment, said cell is one or more of CD9+, CD10+, CD44+, CD54+, CD98+, Tie-2+, TEM-7+, CD31−, CD34−, CD45−, CD133−, CD143−, CD146−, or CXCR4−, as determined by immunolocalization. In a more specific embodiment, said cell is CD9+, CD10+, CD44+, CD54+, CD98+, Tie-2+, TEM-7+, CD31−, CD34−, CD45−, CD133−, CD143−, CD146−, and CXCR4− as determined by immunolocalization. In another specific embodiment, said cell is additionally VEGFR1/Flt-1+ and/or VEGFR2/KDR+, as determined by immunolocalization; and one or more of CD31−, CD34−, CD45−, CD133−, and/or Tie-2− as determined by immunolocalization. In another specific embodiment, said cell is additionally VEGFR1/Flt-1+, VEGFR2/KDR+, CD31−, CD34−, CD45−, CD133−, and Tie-2− as determined by immunolocalization.

In another embodiment, the OCT-4− amnion derived adherent cells are additionally one or more, or all, of CD9+, CD10+, CD44+, CD49f+, CD54+, CD90+, CD98+, CD105+, CD200+, Tie-2+, TEM-7+, VEGFR1/Flt-1+, and/or VEGFR2/KDR+ (CD309+), as determined by immunolocalization; or additionally one or more, or all, of CD31−, CD34−, CD38−, CD45−, CD117−, CD133−, CD143−, CD144−, CD146−, CD271−, CXCR4−, HLA-G−, and/or VE-cadherin−, as determined by immunolocalization, or SOX2−, as determined by RT-PCR.

In certain embodiments, the isolated tissue culture plastic-adherent amnion derived adherent cells are CD49f+. In a specific embodiment, said CD49f+ cells are additionally one or more, or all, of CD9+, CD10+, CD44+, CD54+, CD90+, CD98+, CD105+, CD200+, Tie-2+, TEM-7+, VEGFR1/Flt-1+, and/or VEGFR2/KDR+ (CD309+) as determined by immunolocalization; or additionally one or more, or all, of CD31−, CD34−, CD38−, CD45−, CD117−, CD133−, CD143−, CD144−, CD146−, CD271−, CXCR4−, HLA-G−, OCT-4− and/or VE-cadherin−, as determined by immunolocalization, or SOX2−, as determined by RT-PCR.

In certain other embodiments, the isolated tissue culture plastic-adherent amnion derived adherent cells are HLA-G−, CD90+, and CD117−. In a specific embodiment, said HLA-G−, CD90+, and CD117− cells are additionally one or more, or all, of CD9+, CD10+, CD44+, CD49f+, CD54+, CD98+, CD105+, CD200+, Tie-2+, TEM-7+, VEGFR1/Flt-1+, and/or VEGFR2/KDR+ (CD309+), as determined by immunolocalization; or additionally one or more, or all, of CD31−, CD34−, CD38−, CD45−, CD133−, CD143−, CD144−, CD146−, CD271−, CXCR4−, OCT-4− and/or VE-cadherin−, as determined by immunolocalization, or SOX2−, as determined by RT-PCR.

In another embodiment, the isolated amnion derived adherent cells, or population of amnion derived angiogenic cells, do not constitutively express mRNA for fibroblast growth factor 4 (FGF4), interferon γ (IFNG), chemokine (C—X—C motif) ligand 10 (CXCL10), angiopoietin 4 (ANGPT4), angiopoietin-like 3 (ANGPTL3), fibrinogen a chain (FGA), leptin (LEP), prolactin (PRL), prokineticin 1 (PROK1), tenomodulin (TNMD), FMS-like tyrosine kinase 3 (FLT3), extracellular link domain containing 1 (XLKD1), cadherin 5, type 2 (CDH5), leukocyte cell derived chemotaxin 1 (LECT1), plasminogen (PLG), telomerase reverse transcriptase (TERT), (sex determining region Y)-box 2 (SOX2), NANOG, matrix metalloprotease 13 (MMP-13), distal-less homeobox 5 (DLX5), and/or bone gamma-carboxyglutamate (gla) protein (BGLAP), as determined by RT-PCR, e.g., for 30 cycles under standard culture conditions. In other embodiments, isolated amnion derived adherent cells, or population of amnion derived angiogenic cells, express mRNA for (ARNT2), nerve growth factor (NGF), brain-derived neurotrophic factor (BDNF), glial-derived neurotrophic factor (GDNF), neurotrophin 3 (NT-3), NT-5, hypoxia-Inducible Factor 1α (HIF1A), hypoxia-inducible protein 2 (HIG2), heme oxygenase (decycling) 1 (HMOX1), Extracellular superoxide dismutase [Cu—Zn](SOD3), catalase (CAT), transforming growth factor β1 (TGFB1), transforming growth factor β1 receptor (TGFB1R), and hepatoycte growth factor receptor (HGFR/c-met)

In another aspect, provided herein are isolated populations of cells comprising the amnion derived adherent cells described herein. The populations of cells can be homogeneous populations, e.g., a population of cells, at least about 90%, 95%, 98% or 99% of which are amnion derived adherent cells. The populations of cells can be heterogeneous, e.g., a population of cells wherein at most about 10%, 20%, 30%, 40%, 50%, 60%, 70% or 80% of the cells in the population are amnion derived adherent cells. The isolated populations of cells are not, however, tissue, i.e., amniotic membrane.

In one embodiment, provided herein is an isolated population of cells comprising AMDACs, e.g., a population of cells substantially homogeneous for AMDACs, wherein said AMDACs are adherent to tissue culture plastic, and wherein said AMDACs are OCT-4−, as determined by RT-PCR. In a specific embodiment, the AMDACs are CD49f+ or HLA-G+, e.g., as determined by immunolocalization or RT-PCR. In another specific embodiment, said population of AMDACs is VEGFR1/Flt-1+ and/or VEGFR2/KDR+ as determined by immunolocalization, wherein said isolated population of cells is not an amnion or amniotic membrane. In a more specific embodiment, the AMDACs are OCT-4−, and/or HLA-G− as determined by RT-PCR, and VEGFR1/Flt-1+ and/or VEGFR2/KDR+ as determined by immunolocalization. In a specific embodiment, at least about 50%, 60%, 70%, 80%, 90%, 95%, 98% or 99% of cells in said population are said amnion derived adherent cells. In another specific embodiment, said AMDACs are CD90+, CD105+, or CD117−. In a more specific embodiment, said AMDACs are CD90+, CD105+, and CD117−. In a more specific embodiment, the AMDACs are OCT-4−, CD49f+, CD90+, CD105+, and CD117−. In another specific embodiment, the AMDACs do not express SOX2, e.g., as determined by RT-PCR for 30 cycles. In an even more specific embodiment, the population comprises AMDACs, wherein said AMDACs are OCT-4⁻, HLA-G⁻, CD49f⁺, CD90⁺, CD105⁺, and CD117⁻, as determined by immunolocalization or flow cytometry, and SOX2⁻, e.g., as determined by RT-PCR for 30 cycles In another specific embodiment, said AMDACs in said population of cells are CD90⁺, CD105⁺, or CD117⁻, as determined by immunolocalization or flow cytometry. In a more specific embodiment, the AMDACs are CD90⁺, CD105⁺, and CD117⁻, as determined by immunolocalization or flow cytometry. In a more specific embodiment, the AMDACs are OCT-4⁻ or HLA-G⁻, e.g., as determined by RT-PCR, and are additionally CD49f⁺, CD90⁺, CD105⁺, and CD117⁻ as determined by immunolocalization or flow cytometry. In a more specific embodiment, the AMDACs in said population of cells are OCT-4⁻, HLA-G⁻, CD49f⁺, CD90⁺, CD105⁺, and CD117⁻. In another specific embodiment, the AMDACs do not express SOX2, e.g., as determined by RT-PCR for 30 cycles. In a more specific embodiment, therefore, the cell is OCT-4⁻, CD49f⁺, CD90⁺, CD105⁺, and CD117⁻, as determined by immunolocalization or flow cytometry, and SOX2⁻, as determined by RT-PCR, e.g., for 30 cycles. In an even more specific embodiment, the AMDACs are OCT-4⁻ or HLA-G⁻, and are additionally CD49f⁺, CD90⁺, CD105⁺, and CD117⁻. In a more specific embodiment, the AMDACs are OCT-4⁻, HLA-G⁻, CD49f⁺, CD90⁺, CD105⁺, and CD117⁻.

In another embodiment, the amnion derived adherent cells in said population of cells are adherent to tissue culture plastic, OCT-4⁻ as determined by RT-PCR, and VEGFR1/Flt-1⁺ and/or VEGFR2/KDR⁺ as determined by immunolocalization, and are additionally one or more of CD9⁺, CD10⁺, CD44⁺, CD54⁺, CD98⁺, Tie-2⁺, TEM-7⁺, CD31⁻, CD34⁻, CD45⁻, CD133⁻, CD143⁻, CD146⁻, or CXCR4⁻, as determined by immunolocalization, or HLA-G⁻ as determined by RT-PCR, and wherein said isolated population of cells is not an amnion. In another embodiment, provided herein is an isolated population of cells comprising an amnion derived adherent cell, wherein said cell is adherent to tissue culture plastic, wherein said cell is OCT-4⁻ as determined by RT-PCR, and VEGFR1/Flt-1⁺ and/or VEGFR2/KDR⁺ as determined by immunolocalization, wherein said cell does not express CD34 as detected by immunolocalization after exposure to 1 to 100 ng/mL VEGF for 4 to 21 days, and wherein said isolated population of cells is not an amnion. In a specific embodiment of any of the above embodiments, at least about 50%, 60%, 70%, 80%, 90%, 95%, 98% or 99% of cells in said population are said amnion derived adherent cells.

In another embodiment, any of the above populations of cells comprising amnion derived adherent cells forms sprouts or tube-like structures when cultured in the presence of an extracellular matrix protein, e.g., like collagen type I and IV, or an angiogenic factor, e.g., like vascular endothelial growth factor (VEGF), epithelial growth factor (EGF), platelet derived growth factor (PDGF) or basic fibroblast growth factor (bFGF), e.g., in or on a substrate such as placental collagen, e.g., or MATRIGEL™ for at least 4 days and up to 14 days.

Amnion derived adherent cells, and populations of amnion derived adherent cells, display characteristic expression of proteins related to angiogenesis-related or cardiomyogenesis-related genes. In certain embodiments, provided herein is a cell that expresses, or a population of cells, wherein at least about 50%, 60%, 70%, 80%, 90%, 95% or 98% of cells in said isolated population of cells are amnion derived adherent cells that express RNA for one or more of, or all of, ACTA2 (actin, alpha 2, smooth muscle, aorta), ADAMTS1 (ADAM metallopeptidase with thrombospondin type 1 motif, 1), AMOT (angiomotin), ANG (angiogenin), ANGPT1 (angiopoietin 1), ANGPT2, ANGPTL1 (angiopoietin-like 1), ANGPTL2, ANGPTL4, BAI1 (brain-specific angiogenesis inhibitor 1), CD44, CD200, CEACAM1 (carcinoembryonic antigen-related cell adhesion molecule 1), CHGA (chromogranin A), COL15A1 (collagen, type XV, alpha 1), COL18A1 (collagen, type XVIII, alpha 1), COL4A1 (collagen, type IV, alpha 1), COL4A2 (collagen, type IV, alpha 2), COL4A3 (collagen, type IV, alpha 3), CSF3 (colony stimulating factor 3 (granulocyte), CTGF (connective tissue growth factor), CXCL12 (chemokine (CXC motif) ligand 12 (stromal cell-derived factor 1)), CXCL2, DNMT3B (DNA (cytosine-5-)-methyltransferase 3 beta), ECGF1 (thymidine phosphorylase), EDG1 (endothelial cell differentiation gene 1), EDIL3 (EGF-like repeats and discoidin I-like domains 3), ENPP2 (ectonucleotide pyrophosphatase/phosphodiesterase 2), EPHB2 (EPH receptor B2), FBLN5 (FIBULIN 5), F2 (coagulation factor II (thrombin)), FGF1 (acidic fibroblast growth factor), FGF2 (basic fibroblast growth factor), FIGF (c-fos induced growth factor (vascular endothelial growth factor D)), FLT4 (fms-related tyrosine kinase 4), FN1 (fibronectin 1), FST (follistatin), FOXC2 (forkhead box C2 (MFH-1, mesenchyme forkhead 1)), GRN (granulin), HGF (hepatocyte growth factor), HEY1 (hairy/enhancer-of-split related with YRPW motif 1), HSPG2 (heparan sulfate proteoglycan 2), IFNB1 (interferon, beta 1, fibroblast), IL8 (interleukin 8), IL12A, ITGA4 (integrin, alpha 4; CD49d), ITGAV (integrin, alpha V), ITGB3 (integrin, beta 3), MDK (midkine), MMP2 (matrix metalloprotease 2), MYOZ2 (myozenin 2), NRP1 (neuropilin 1), NRP2, PDGFB (platelet-derived growth factor β), PDGFRA (platelet-derived growth factor receptor α), PDGFRB, PECAM1 (platelet/endothelial cell adhesion molecule), PF4 (platelet factor 4), PGK1 (phosphoglycerate kinase 1), PROX1 (prospero homeobox 1), PTN (pleiotrophin), SEMA3F (semophorin 3F), SERPINB5 (serpin peptidase inhibitor, clade B (ovalbumin), member 5), SERPINC1, SERPINF1, TIMP2 (tissue inhibitor of metalloproteinases 2), TIMP3, TGFA (transforming growth factor, alpha), TGFB1, THBS1 (thrombospondin 1), THBS2, TIE1 (tyrosine kinase with immunoglobulin-like and EGF-like domains 1), TIE2/TEK, TNF (tumor necrosis factor), TNNI1 (troponin I, type 1), TNFSF15 (tumor necrosis factor (ligand) superfamily, member 15), VASH1 (vasohibin 1), VEGF (vascular endothelial growth factor), VEGFB, VEGFC, VEGFR1/FLT1 (vascular endothelial growth factor receptor 1), and/or VEGFR2/KDR.

When human cells are used, the gene designations throughout refer to human sequences, and, as is well known to persons of skill in the art, representative sequences can be found in literature, or in GenBank. Probes to the sequences can be determined by sequences that are publicly-available, or through commercial sources, e.g., specific TAQMAN® probes or TAQMAN® Angiogenesis Array (Applied Biosystems, part no. 4378710).

Amnion derived adherent cells, and populations of amnion derived adherent cells, display characteristic expression of angiogenesis-related proteins. In certain embodiments, provided herein is a cell that expresses, or a population of cells, wherein at least about 50%, 60%, 70%, 80%, 90%, 95% or 98% of cells in said isolated population of cells are amnion derived adherent cells that express CD49d, Connexin-43, HLA-ABC, Beta 2-microglobulin, CD349, CD318, PDL1, CD106, Galectin-1, ADAM 17 precursor (A disintegrin and metalloproteinase domain 17) (TNF-alpha converting enzyme) (TNF-alpha convertase), Angiotensinogen precursor, Filamin A (Alpha-filamin) (Filamin 1) (Endothelial actin-binding protein) (ABP-280) (Nonmuscle filamin), Alpha-actinin 1 (Alpha-actinin cytoskeletal isoform) (Non-muscle alpha-actinin 1) (F-actin cross linking protein), Low-density lipoprotein receptor-related protein 2 precursor (Megalin) (Glycoprotein 330) (gp330), Macrophage scavenger receptor types I and II (Macrophage acetylated LDL receptor I and II), Activin receptor type IIB precursor (ACTR-IIB), Wnt-9 protein, Glial fibrillary acidic protein, astrocyte (GFAP), Myosin-binding protein C, cardiac-type (Cardiac MyBP-C) (C-protein, cardiac muscle isoform), and/or Myosin heavy chain, nonmuscle type A (Cellular myosin heavy chain, type A) (Nonmuscle myosin heavy chain-A) (NM-MHC-A).

The amnion derived adherent cells provided herein further secrete proteins that promote angiogenesis, e.g., in endothelial cells, endothelial progenitor cells, or the like. In certain embodiments, the amnion derived adherent cell, population of amnion derived adherent cells, or population of cells comprising amnion derived adherent cells, e.g., wherein at least about 50%, 60%, 70%, 80%, 90%, 95% or 98% of cells in said isolated population of cells are amnion derived adherent cells, secrete one or more, or all, of VEGF, HGF, IL-8, MCP-3, FGF2, Follistatin, G-CSF, EGF, ENA-78, GRO, IL-6, MCP-1, PDGF-BB, TIMP-2, uPAR, Galectin-1, e.g., into culture medium in which the cell, or cells, are grown.

In another embodiment, any of the above populations of cells comprising amnion derived adherent cells can cause the formation of sprouts or tube-like structures in a population of endothelial cells in contact with said amnion derived adherent cells. In a specific embodiment, the amnion-derived angiogenic cells are co-cultured with human endothelial cells, forming sprouts or tube-like structures, or supporting the endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days and/or up to 14 days.

In another embodiment, any of the above populations of cells comprising amnion derived adherent cells secrete angiogenic factors such as vascular endothelial growth factor (VEGF), epithelial growth factor (EGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In another embodiment, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that express angiogenic micro RNAs (miRNAs) at a higher level than bone marrow-derived mesenchymal stem cells, wherein said miRNAs comprise one or more, or all of, miR-17-3p, miR-18a, miR-18b, miR-19b, miR-92, and/or miR-296. In another embodiment, provided herein is a population of cells, e.g., a population of amnion derived adherent cells, or a population of cells wherein at least about 50%, 60%, 70%, 80%, 90%, 95% or 98% of cells in said isolated population of cells are amnion derived adherent cells that express one or more of, or all of, angiogenic micro RNAs (miRNAs) at a lower level than bone marrow-derived mesenchymal stem cells, wherein said miRNAs comprise one or more, or all of, miR-20a, miR-20b, miR-221, miR-222, miR-15b, and/or miR-16. In certain embodiments, AMDACs, or populations of AMDACs, express one or more, or all, of the angiogenic miRNAs miR-17-3p, miR-18a, miR-18b, miR-19b, miR-92, miR-20a, miR-20b, (members of the of the angiogenic miRNA cluster 17-92), miR-296, miR-221, miR-222, miR-15b, and/or miR-16.

Thus, in one embodiment, provided herein is an isolated amnion derived adherent cell, wherein said cell is adherent to tissue culture plastic, and wherein said cell is OCT-4$^-$, as determined by RT-PCR, and CD49f$^+$, HLA-G$^-$, CD90$^+$, CD105$^+$, and CD117$^-$, as determined by immunolocalization, and wherein said cell: (a) expresses one or more of CD9, CD10$^+$, CD44, CD54, CD98, CD200, Tie-2, TEM-7, VEGFR1/Flt-1, or VEGFR2/KDR (CD309), as determined by immunolocalization; (b) lacks expression of CD31, CD34, CD38, CD45, CD133, CD143, CD144, CD146, CD271, CXCR4, HLA-G, or VE-cadherin, as determined by immunolocalization, or lacks expression of SOX2, as determined by RT-PCR; (c) express mRNA for ACTA2, ADAMTS1, AMOT, ANG, ANGPT1, ANGPT2, ANGPTL1, ANGPTL2, ANGPTL4, BAI1, CD44, CD200, CEACAM1, CHGA, COL15A1, COL18A1, COL4A1, COL4A2, COL4A3, CSF3, CTGF, CXCL12, CXCL2, DNMT3B, ECGF1, EDG1, EDIL3, ENPP2, EPHB2, FBLN5, F2, FGF1, FGF2, FIGF, FLT4, FN1, FST, FOXC2, GRN, HGF, HEY1, HSPG2, IFNB1, IL8, IL12A, ITGA4, ITGAV, ITGB3, MDK, MMP2, MYOZ2, NRP1, NRP2, PDGFB, PDGFRA, PDGFRB, PECAM1, PF4, PGK1, PROX1, PTN, SEMA3F, SERPINB5, SERPINC1, SERPINF1, TIMP2, TIMP3, TGFA, TGFB1, THBS1, THBS2, TIE1, TIE2/TEK, TNF, TNNI1, TNFSF15, VASH1, VEGF, VEGFB, VEGFC, VEGFR1/FLT1, or VEGFR2/KDR; (d) expresses one or more of the proteins CD49d, Connexin-43, HLA-ABC, Beta 2-microglobulin, CD349, CD318, PDL1, CD106, Galectin-1, ADAM 17, angiotensinogen precursor, filamin A, alpha-actinin 1, megalin, macrophage acetylated LDL receptor I and II, activin receptor type IIB precursor, Wnt-9 protein, glial fibrillary acidic protein, astrocyte, myosin-binding protein C, or myosin heavy chain, nonmuscle type A; (e) secretes VEGF, HGF, IL-8, MCP-3, FGF2, Follistatin, G-CSF, EGF, ENA-78, GRO, IL-6, MCP-1, PDGF-BB, TIMP-2, uPAR, or galectin-1 into culture medium in which the cell grows; (f) expresses micro RNAs miR-17-3p, miR-18a, miR-18b, miR-19b, miR-92, or miR-296 at a higher level than an equivalent number of bone marrow-derived mesenchymal stem cells; (g) expresses micro RNAs miR-20a, miR-20b, miR-221, miR-222, miR-15b, or miR-16 at a lower level than an equivalent number of bone marrow-derived mesenchymal stem cells; (h) expresses miRNAs miR-17-3p, miR-18a, miR-18b, miR-19b, miR-92, miR-20a, miR-20b, miR-296, miR-221, miR-222, miR-15b, or miR-16; and/or (i) expresses increased levels of CD202b, IL-8 or VEGF when cultured in less than about 5% $O_2$, compared to expression of CD202b, IL-8 or VEGF under 21% $O_2$. In a specific embodiment, the isolated amnion derived adherent cell is OCT-4$^-$, as determined by RT-PCR, and CD49f$^+$, HLA-G$^-$, CD90, CD105', and CD117$^-$, as determined by immunolocalization, and (a) expresses CD9, CD10$^+$, CD44, CD54, CD90, CD98, CD200, Tie-2, TEM-7, VEGFR1/Flt-1, and/or VEGFR2/KDR (CD309), as determined by immunolocalization; (b) lacks expression of CD31, CD34, CD38, CD45, CD133, CD143, CD144, CD146, CD271, CXCR4, HLA-G, and/or VE-cadherin, as determined by immunolocalization, or lacks expression of SOX2, as determined by RT-PCR; (c) express mRNA for ACTA2, ADAMTS1, AMOT, ANG, ANGPT1, ANGPT2, ANGPTL1, ANGPTL2, ANGPTL4, BAI1, CD44, CD200, CEACAM1, CHGA, COL15A1, COL18A1, COL4A1, COL4A2, COL4A3, CSF3, CTGF, CXCL12, CXCL2, DNMT3B, ECGF1, EDG1, EDIL3, ENPP2, EPHB2, FBLN5, F2, FGF1, FGF2, FIGF, FLT4, FN1, FST, FOXC2, GRN, HGF, HEY1, HSPG2, IFNB1, IL8, IL12A, ITGA4, ITGAV, ITGB3, MDK, MMP2, MYOZ2, NRP1, NRP2, PDGFB, PDGFRA, PDGFRB, PECAM1, PF4, PGK1, PROX1, PTN, SEMA3F, SERPINB5, SERPINC1, SERPINF1, TIMP2, TIMP3, TGFA, TGFB1, THBS1, THBS2, TIE1, TIE2/TEK, TNF, TNNI1, TNFSF15, VASH1, VEGF, VEGFB, VEGFC, VEGFR1/FLT1, and/or VEGFR2/KDR; (d) expresses one or more of CD49d, Connexin-43, HLA-ABC, Beta 2-microglobulin, CD349, CD318, PDL1, CD106, Galectin-1, ADAM 17, angiotensinogen precursor, filamin A, alpha-actinin 1, megalin, macrophage acetylated LDL receptor I and II, activin receptor type IIB precursor, Wnt-9 protein, glial fibrillary acidic protein, astrocyte, myosin-binding protein C, and/or myosin heavy chain, nonmuscle type A; (e) secretes VEGF, HGF, IL-8, MCP-3, FGF2, Follistatin, G-CSF, EGF, ENA-78, GRO, IL-6, MCP-1, PDGF-BB, TIMP-2, uPAR, and/or Galectin-1, e.g., into culture medium in which the cell grows; (f) expresses micro RNAs miR-17-3p, miR-18a, miR-18b, miR-19b, miR-92, and/or miR-296 at a higher level than an equivalent number of bone marrow-derived mesenchymal stem cells; (g) expresses micro RNAs miR-20a, miR-20b, miR-221, miR-222, miR-15b, and/or miR-16 at a lower level than an equivalent number of bone marrow-derived mesenchymal stem cells; (h) expresses miRNAs miR-17-3p, miR-18a, miR-18b, miR-19b, miR-92, miR-20a, miR-20b, miR-296, miR-221, miR-222, miR-15b, and/or miR-16; and/or (i) expresses increased levels of CD202b, IL-8 and/or VEGF when cultured in less than about 5% $O_2$, compared to expression of CD202b, IL-8 and/or VEGF under 21% $O_2$. Further provided herein are populations of cells comprising AMDACs, e.g. populations of AMDACs, having one or more of the above-recited characteristics.

In another embodiment, any of the above populations of cells comprising amnion derived adherent cells secretes angiogenic factors. In specific embodiments, the population of cells secretes vascular endothelial growth factor (VEGF), epithelial growth factor (EGF), platelet derived growth factor (PDGF), basic fibroblast growth factor (bFGF), and/or interleukin-8 (IL-8). In other specific embodiments, the population of cells comprising amnion-derived angiogenic cells secretes one or more angiogenic factors and thereby induces human endothelial cells to migrate in an in vitro wound healing assay. In other specific embodiments, the population of cells comprising amnion derived adherent cells induces maturation, differentiation or proliferation of human endothelial cells, endothelial progenitors, myocytes or myoblasts.

In another embodiment, any of the above populations of cells comprising amnion derived adherent cells take up acetylated low density lipoprotein (LDL) when cultured in the presence of extracellular matrix proteins, e.g., collagen type I or IV, and/or one or more angiogenic factors, e.g., VEGF, EGF, PDGF, or bFGF, e.g., on a substrate such as placental collagen or MATRIGEL™.

In another embodiment, provided herein is a population of cells comprising amnion derived adherent cells, wherein said cells are adherent to tissue culture plastic, and wherein said cells are OCT-4⁻, as determined by RT-PCR, and VEGFR2/KDR⁺, CD9⁺, CD54⁺, CD105⁺, CD200⁺, or VE-cadherin⁻, as determined by immunolocalization. In specific embodiments, at least 10%, 20%, 30%, 40%, 50%, 60%, 70%, 80%, 90%, 95%, 98% or 99% of the cells in said population of cells are amnion derived cells that are OCT-4⁻, as determined by RT-PCR, and VEGFR2/KDR⁺, CD9⁺, CD54⁺, CD105⁺, CD200⁺, or VE-cadherin⁻, as determined by immunolocalization. In another specific embodiment, at least 10%, 20%, 30%, 40%, 50%, 60%, 70%, 80%, 90%, 95%, 98% or 99% of the cells in said population are amnion derived cells that are OCT-4⁻, as determined by RT-PCR, and VEGFR2/KDR⁺, CD9⁺, CD54⁺, CD105⁺, CD200⁺, and VE-cadherin⁻, as determined by immunolocalization. In another specific embodiment, said cells that are OCT-4⁻, as determined by RT-PCR, and VEGFR2/KDR⁺, CD9⁺, CD54⁺, CD105⁺, CD200⁺, or VE-cadherin⁻, as determined by immunolocalization, do not express CD34, as detected by immunolocalization, after exposure to 1 to 100 ng/mL VEGF for 4 to 21 days. In another specific embodiment, said cells are also VE-cadherin⁻.

The populations of cells provided herein, comprising amnion derived adherent cells, are able to form sprouts or tube-like structures resembling vessels or vasculature. In one embodiment, the populations of cells comprising amnion derived adherent cells form sprouts or tube-like structures when cultured in the presence of an angiogenic moiety, e.g., VEGF, EGF, PDGF or bFGF. In a more specific embodiment, said amnion derived cells that are OCT-4⁻, as determined by RT-PCR, and VEGFR2/KDR⁺, CD9⁺, CD54⁺, CD105⁺, CD200⁺, or VE-cadherin⁻, as determined by immunolocalization, form sprouts or tube-like structures when said population of cells is cultured in the presence of vascular endothelial growth factor (VEGF).

The amnion derived adherent cells described herein display the above characteristics, e.g., combinations of cell surface markers and/or gene expression profiles, and/or angiogenic potency and function, in primary culture, or during proliferation in medium suitable for the culture of stem cells. Such medium includes, for example, medium comprising 1 to 100% DMEM-LG (Gibco), 1 to 100% MCDB-201 (Sigma), 1 to 10% fetal calf serum (FCS) (Hyclone Laboratories), 0.1 to 5× insulin-transferrin-selenium (ITS, Sigma), 0.1 to 5× linolenic-acid-bovine-serum-albumin (LA-BSA, Sigma), $10^{-5}$ to $10^{-15}$ M dexamethasone (Sigma), $10^{-2}$ to $10^{-10}$ M ascorbic acid 2-phosphate (Sigma), 1 to 50 ng/mL epidermal growth factor (EGF), (R&D Systems), 1 to 50 ng/mL platelet derived-growth factor (PDGF-BB) (R&D Systems), and 100 U penicillin/1000 U streptomycin. In a specific embodiment, the medium comprises 60% DMEM-LG (Gibco), 40% MCDB-201 (Sigma), 2% fetal calf serum (FCS) (Hyclone Laboratories), 1× insulin-transferrin-selenium (ITS), 1× linolenic-acid-bovine-serum-albumin (LA-BSA), $10^{-9}$ M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin Other suitable media are described below.

The isolated populations of amnion derived adherent cells provided herein can comprise about, at least about, or no more than about, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more amnion derived adherent cells, e.g., in a container. In various embodiments, at least 10%, 20%, 30%, 40%, 50%, 60%, 70%, 80%, 90%, 95%, or 99% of the cells in the isolated cell populations provided herein are amnion derived adherent cells. That is, a population of isolated amnion derived adherent cells can comprise, e.g., as much as 1%, 5%, 10%, 20%, 30%, 40%, 50%, 60%, 70%, 80%, 90% non-stem cells.

The amnion derived adherent cells provided herein can be cultured on a substrate. In various embodiments, the substrate can be any surface on which culture and/or selection of amnion derived adherent cells, can be accomplished. Typically, the substrate is plastic, e.g., tissue culture dish or multiwell plate plastic. Tissue culture plastic can be treated, coated or imprinted with a biomolecule or synthetic mimetic agent, e.g., CELLSTART™, MESENCULT™ ACF-substrate, ornithine, or polylysine, or an extracellular matrix protein, e.g., collagen, laminin, fibronectin, vitronectin, or the like.

Amnion derived cells, e.g., the amnion derived adherent cells provided herein, and populations of such cells, can be isolated from one or more placentas. For example, an isolated population of the amnion derived cells provided herein can be a population of placental cells comprising such cells obtained from, or contained within, disrupted amnion tissue, e.g., tissue digestate (that is, the collection of cells obtained by enzymatic digestion of an amnion), wherein said population of cells is enriched for the amnion derived cells, and wherein the tissue is from a single placenta or from two or more placentas. Isolated amnion derived cells can be cultured and expanded to produce populations of such cells. Populations of placental cells comprising amnion derived adherent cells can also be cultured and expanded to produce populations of amnion derived adherent cells.

In certain embodiments, AMDACs displaying any of the above marker and/or gene expression characteristics have been passaged at least 1, 2, 3, 4, 5, 6, 7, 8, 9, 10, 11, 12, 13, 14, 15, 16, 17, 18, 19 or 20 times, or more. In certain other embodiments, AMDACs displaying any of the above marker and/or gene expression characteristics have been doubled in culture at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 times, or more.

5.2 Populations of Amnion Derived Adherent Cells Comprising Other Cell Types The isolated cell populations comprising amnion derived adherent cells described herein can comprise a second cell type, e.g., placental cells that are not amnion derived adherent cells, or, e.g., cells that are not placental cells. For example, an isolated population of amnion derived adherent cells can comprise, e.g., can be combined with, a population of a second type of cells, wherein said second type of cell are, e.g., embryonic stem cells, blood cells (e.g., placental blood, placental blood cells, umbilical cord blood, umbilical cord blood cells, peripheral blood, peripheral blood cells, nucleated cells from placental blood, umbilical cord blood, or peripheral blood, and the like), stem cells isolated from blood (e.g., stem cells isolated from placental blood, umbilical cord blood or peripheral blood), placental stem cells (e.g., the placental stem cells described in U.S. Pat. No. 7,468,276, and in U.S. Patent Application Publication No. and 2007/0275362, the disclosures of which are incorporated herein by reference in their entireties), nucleated cells from placental perfusate, e.g., total nucleated cells from placental perfusate; umbilical cord stem cells, populations of blood-derived nucleated cells, bone marrow-derived mesenchymal stromal cells, bone marrow-derived mesenchymal stem cells, bone marrow-derived hematopoietic stem cells, crude bone marrow, adult (somatic) stem cells, populations of stem cells contained within tissue, cultured cells, e.g., cultured stem cells, populations of fully-differentiated cells (e.g., chondrocytes, fibroblasts, amniotic cells, osteoblasts, muscle cells, cardiac cells, etc.), pericytes, and the like. In a specific embodiment, a population of cells comprising amnion derived adherent cells comprises placental stem cells or stem cells from umbilical cord. In certain embodiments in which the second type of cell is blood or blood cells, erythrocytes have been removed from the population of cells.

In a specific embodiment, the second type of cell is a hematopoietic stem cell. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

In another embodiment, an isolated population of amnion derived adherent cells is combined with a plurality of adult or progenitor cells from the vascular system. In various embodiments, the cells are endothelial cells, endothelial progenitor cells, myocytes, cardiomyocytes, pericytes, angioblasts, myoblasts or cardiomyoblasts.

In a another embodiment, the second cell type is a non-embryonic cell type manipulated in culture in order to express markers of pluripotency and functions associated with embryonic stem cells In specific embodiments of the above isolated populations of amnion derived adherent cells, either or both of the amnion derived adherent cells and cells of a second type are autologous, or are allogeneic, to an intended recipient of the cells.

Further provided herein is a composition comprising amnion derived adherent cells, and a plurality of stem cells other than the amnion derived adherent cells. In a specific embodiment, the composition comprises a stem cell that is obtained from a placenta, i.e., a placental stem cell, e.g., placental stem cells as described in U.S. Pat. Nos. 7,045,148; 7,255,879; and 7,311,905, and in U.S. Patent Application Publication No. 2007/0275362, the disclosures of each of which are incorporated herein by reference in their entireties. In specific embodiments, said placental stem cells are $CD200^+$ and HLA-$G^+$; $CD73^+$, $CD105^+$, and $CD200^+$; $CD200^+$ and OCT-$4^+$; $CD73^+$, $CD105^+$ and HLA-$G^+$; CD73' and $CD105^+$ and facilitate the formation of one or more embryoid-like bodies in a population of placental cells comprising said stem cell when said population is cultured under conditions that allow the formation of an embryoid-like body; or OCT-$4^+$ and facilitate the formation of one or more embryoid-like bodies in a population of placental cells comprising the stem cell when said population is cultured under conditions that allow formation of embryoid-like bodies; or any combination thereof. In a more specific embodiment, said $CD200^+$, HLA-$G^+$ stem cells are $CD34^-$, $CD38^-$, $CD45^-$, CD73' and CD105+. In another more specific embodiment, said $CD73^+$, $CD105^+$, and CD200 stem cells are $CD34^-$, $CD38^-$, $CD45^-$, and HLA-$G^+$. In another more specific embodiment, said $CD200^+$, OCT-$4^+$ stem cells are $CD34^-$, $CD38^-$, $CD45^-$, $CD73^+$, $CD105^+$ and HLA-$G^+$. In another more specific embodiment, said $CD73^+$, $CD105^+$ and HLA-$G^+$ stem cells are $CD34^-$, $CD45^-$, OCT-$4^+$ and $CD200^+$. In another more specific embodiment, said $CD73^+$ and $CD105^+$ stem cells are OCT-$4^+$, $CD34^-$, $CD38^-$ and $CD45^-$. In another more specific embodiment, said OCT-$4^+$ stem cells are $CD73^+$, $CD105^+$, $CD200^+$, $CD34^-$, $CD38^-$, and $CD45^-$. In another more specific embodiment, the placental stem cells are maternal in origin (that is, have the maternal genotype). In another more specific embodiment, the placental stem cells are fetal in origin (that is, have the fetal genotype).

In another specific embodiment, the composition comprises amnion derived adherent cells, and embryonic stem cells. In another specific embodiment, the composition comprises amnion derived adherent cells and mesenchymal stromal or stem cells, e.g., bone marrow-derived mesenchymal stromal or stem cells. In another specific embodiment, the composition comprises bone marrow-derived hematopoietic stem cells. In another specific embodiment, the composition comprises amnion derived adherent cells and hematopoietic progenitor cells, e.g., hematopoietic progenitor cells from bone marrow, fetal blood, umbilical cord blood, placental blood, and/or peripheral blood. In another specific embodiment, the composition comprises amnion derived adherent cells and somatic stem cells. In a more specific embodiment, said somatic stem cell is a neural stem cell, a hepatic stem cell, a pancreatic stem cell, an endothelial stem cell, a cardiac stem cell, or a muscle stem cell.

In other specific embodiments, the second type of cells comprise about, at least, or no more than, 10%, 15%, 20%, 25%, 30%, 35%, 40%, 45%, or 50% of cells in said population. In other specific embodiments, the AMDACs in said composition comprise at least 50%, 55%, 60%, 65%, 70%, 75%, 80%, 85% or 90% of cells in said composition. In other specific embodiments, the amnion derived adherent cells comprise about, at least, or no more than, 10%, 15%, 20%, 25%, 30%, 35%, 40%, or 45% of cells in said population.

Cells in an isolated population of amnion derived adherent cells can be combined with a plurality of cells of another type, e.g., with a population of stem cells, in a ratio of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated population of amnion derived adherent cells can be combined with a plurality of cells of a plurality of cell types, as well.

5.3 Growth in Culture

The growth of the amnion derived adherent cells described herein, as for any mammalian cell, depends in part upon the particular medium selected for growth. Under optimum conditions, amnion derived adherent cells typically double in number in approximately 24 hours. During culture, the amnion derived adherent cells described herein adhere to a substrate in culture, e.g. the surface of a tissue culture container (e.g., tissue culture dish plastic, fibronectin-coated plastic, and the like) and form a monolayer. Typically, the cells establish in culture within 2-7 days after digestion of the amnion. They proliferate at approximately 0.4 to 1.2 population doublings per day and can undergo at least 30 to 50 population doublings. The cells display a mesenchymal/fibroblastic cell-like phenotype during subconfluence and expansion, and a cuboidal/cobblestone-like appearance at confluence, and proliferation in culture is strongly contact-inhibited. Populations of amnion-derived angiogenic cells can form embryoid bodies during expansion in culture.

5.4 Methods of Obtaining Amnion-Derived Angiogenic Cells

The amnion derived adherent cells, and populations of cells comprising the amnion derived adherent cells, can be produced, e.g., isolated from other cells or cell populations, for example, through particular methods of digestion of amnion tissue, optionally followed by assessment of the resulting cells or cell population for the presence or absence of markers, or combinations of markers, characteristics of amnion derived adherent cells, or by obtaining amnion cells and selecting on the basis of markers characteristic of amnion derived adherent cells.

The amnion derived adherent cells, and isolated populations of cells comprising the amnion derived adherent cells, provided herein can be produced by, e.g., digestion of amnion tissue followed by selection for adherent cells. In one embodiment, for instance, isolated amnion derived adherent cells, or an isolated population of cells comprising amnion derived adherent cells, can be produced by (1) digesting amnion tissue with a first enzyme to dissociate cells from the epithelial layer of the amnion from cells from the mesenchymal layer of the amnion; (2) subsequently digesting the mesenchymal layer of the amnion with a second enzyme to form a single-cell suspension; (3) culturing cells in said single-cell suspension on a tissue culture surface, e.g., tissue culture plastic; and (4) selecting cells that adhere to said surface after a change of medium, thereby producing an isolated population of cells comprising amnion derived adherent cells. In a specific embodiment, said first enzyme is trypsin. In a more specific embodiment, said trypsin is used at a concentration of 0.25% trypsin (w/v), in 5-20, e.g., 10 milliliters solution per gram of amnion tissue to be digested. In another more specific embodiment, said digesting with trypsin is allowed to proceed for about 15 minutes at 37° C. and is repeated up to three times. In another specific embodiment, said second enzyme is collagenase. In a more specific embodiment, said collagenase is used at a concentration between 50 and 500 U/L in 5 mL per gram of amnion tissue to be digested. In another more specific embodiment, said digesting with collagenase is allowed to proceed for about 45-60 minutes at 37° C. In another specific embodiment, the single-cell suspension formed after digestion with collagenase is filtered through, e.g., a 75 μM-150 μM filter between step (2) and step (3). In another specific embodiment, said first enzyme is trypsin, and said second enzyme is collagenase.

An isolated population of cells comprising amnion derived adherent cells can, in another embodiment, be obtained by selecting cells from amnion, e.g., cells obtained by digesting amnion tissue as described elsewhere herein, that display one or more characteristics of an amnion derived adherent cell. In one embodiment, for example, a cell population is produced by a method comprising selecting amnion cells that are (a) negative for OCT-4, as determined by RT-PCR, and (b) positive for one or more of VEGFR2/KDR, CD9, CD54, CD105$^+$, CD200, as determined by immunolocalization; and isolating said cells from other cells to form a cell population. In a specific embodiment, said amnion cells are additionally VE-cadherin$^-$. In a specific embodiment, a cell population is produced by selecting placental cells that are (a) negative for OCT-4, as determined by RT-PCR, and VE-cadherin, as determined by immunolocalization, and (b) positive for each of VEGFR2/KDR, CD9, CD54, CD105$^+$, CD200, as determined by immunolocalization; and isolating said cells from other cells to form a cell population. In certain embodiments, selection by immunolocalization is performed before selection by RT-PCR. In another specific embodiment, said selecting comprises selecting cells that do not express cellular marker CD34 after culture for 4 to 21 days in the presence of 1 to 100 ng/mL VEGF.

In another embodiment, for example, a cell population is produced by a method comprising selecting amnion cells that are adherent to tissue culture plastic and are OCT-4$^-$, as determined by RT-PCR, and VEGFR1/Flt-1$^+$ and VEGFR2/KDR$^+$, as determined by immunolocalization, and isolating said cells from other cells to form a cell population. In a specific embodiment, a cell population is produced by a method comprising selecting amnion cells that are OCT-4⁻, as determined by RT-PCR, and VEGFR1/Flt-1⁺, VEGFR2/KDR⁺, and HLA-G⁻, as determined by immunolocalization. In another specific embodiment, said cell population is produced by selecting amnion cells that are additionally one or more, or all, of CD9⁺, CD10⁺, CD44⁺, CD54⁺, CD98⁺, Tie-2⁺, TEM-7⁺, CD31⁻, CD34⁻, CD45⁻, CD133⁻, CD143⁻, CD146⁻, and/or CXCR4⁻ (chemokine (C—X—C motif) receptor 4) as determined by immunolocalization, and isolating the cells from cells that do not display one or more of these characteristics. In another specific embodiment, said cell population is produced by selecting amnion cells that are additionally VE-cadherin⁻ as determined by immunolocalization, and isolating the cells from cells that are VE-cadherin⁺. In another specific embodiment, said cell population is produced by selecting amnion cells that are additionally CD105 and CD200⁺ as determined by immunolocalization, and isolating the cells from cells that are CD105⁻ or CD200⁻. In another specific embodiment, said cell does not express CD34 as detected by immunolocalization after exposure to 1 to 100 ng/mL VEGF for 4 to 21 days.

In the selection of cells, it is not necessary to test an entire population of cells for characteristics specific to amnion derived adherent cells. Instead, one or more aliquots of cells (e.g., about 0.5%-2%) of a population of cells may be tested for such characteristics, and the results can be attributed to the remaining cells in the population.

Selected cells can be confirmed to be the amnion derived adherent cells provided herein by culturing a sample of the cells (e.g., about 10⁴ to about 10⁵ cells) on a substrate, e.g., MATRIGEL™, for 4 to 14, e.g., 7, days in the presence of VEGF (e.g., about 50 ng/mL), and visually inspecting the cells for the appearance of sprouts and/or cellular networks.

Amnion derived adherent cells can be selected by the above markers using any method known in the art of cell selection. For example, the adherent cells can be selected using an antibody or antibodies to one or more cell surface markers, for example, in immunolocalization, e.g., flow cytometry or FACS. Selection can be accomplished using antibodies in conjunction with magnetic beads. Antibodies that are specific for certain markers are known in the art and are available commercially, e.g., antibodies to CD9 (Abcam); CD54 (Abcam); CD105 (Abcam; BioDesign International, Saco, Me., etc.); CD200 (Abcam) cytokeratin (SigmaAldrich). Antibodies to other markers are also available commercially, e.g., CD34, CD38 and CD45 are available from, e.g., StemCell Technologies or BioDesign International. Primers to OCT-4 sequences suitable for RT-PCR can be obtained commercially, e.g., from Millipore or Invitrogen, or can be readily derived from the human sequence in GenBank Accession No. DQ486513.

Detailed methods of obtaining placenta and amnion tissue, and treating such tissue in order to obtain amnion derived adherent cells, are provided below.

5.4.1 Cell Collection Composition

Generally, cells can be obtained from amnion from a mammalian placenta, e.g., a human placenta, using a physiologically-acceptable solution, e.g., a cell collection composition. Preferably, the cell collection composition prevents or suppresses apoptosis, prevents or suppresses cell death, lysis, decomposition and the like. A cell collection composition is described in detail in related U.S. Patent Application Publication No. 2007/0190042, entitled "Improved Medium for Collecting Placental Stem Cells and Preserving Organs," the disclosure of which is incorporated herein by reference in its entirety.

The cell collection composition can comprise any physiologically-acceptable solution suitable for the collection and/or culture of amnion derived adherent cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like, with or without the addition of a buffering component, e.g., 4-(2-hydroxyethyl)-1-piperazineethanesulfonic acid (HEPES).

The cell collection composition can comprise one or more components that tend to preserve cells, e.g., amnion derived adherent cells, that is, prevent the cells from dying, or delay the death of the cells, reduce the number of cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE™, hyaluronidase, and the like. The use of cell collection compositions comprising tissue-digesting enzymes is discussed in more detail below.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa*, *Staphylococcus aureus*, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 M to about 5 µM).

The amnion derived adherent cells described herein can also be collected, e.g., during and after digestion as described below, into a simple physiologically-acceptable buffer, e.g., phosphate-buffered saline, a 0.9% NaCl solution, cell culture medium, or the like.

5.4.2 Collection and Handling of Placenta

Generally, a human placenta is recovered shortly after its expulsion after birth, or after, e.g., Caesarian section. In a preferred embodiment, the placenta is recovered from a patient after informed consent and after a complete medical history of the patient is obtained and is associated with the placenta. Preferably, the medical history continues after delivery. Such a medical history can be used to coordinate subsequent use of the placenta or cells harvested therefrom. For example, human placental cells, e.g., amnion derived adherent cells, can be used, in light of the medical history, for personalized medicine for the infant, or a close relative, associated with the placenta, or for parents, siblings, or other relatives of the infant.

Prior to recovery of amnion derived adherent cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to cell collection, can be stored under sterile conditions and at a temperature of, e.g., 4 to 25° C. (centigrade), e.g., at room temperature. The placenta may be stored for, e.g., a period of for zero to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta can be stored in an anticoagulant solution at a temperature of, e.g., 4 to 25° C. (centigrade). Suitable anticoagulant solutions are well known in the art. For example, a solution of sodium citrate, heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before cells are collected.

5.4.3 Physical Disruption and Enzymatic Digestion of Amnion Tissue

In one embodiment, the amnion is separated from the rest of the placenta, e.g., by blunt dissection, e.g., using the fingers. The amnion can be dissected, e.g., into parts or tissue segments, prior to enzymatic digestion and adherent cell recovery. Amnion derived adherent cells can be obtained from a whole amnion, or from a small segment of amnion, e.g., a segment of amnion that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 square millimeters in area.

Amnion derived adherent cells can generally be collected from a placental amnion or a portion thereof, at any time within about the first three days post-expulsion, but preferably between about 0 hours and 48 hours after expulsion, or about 8 hours and about 18 hours post-expulsion.

In one embodiment, amnion derived adherent cells are extracted from amnion tissue by enzymatic digestion using one or more tissue-digesting enzymes. The amnion, or a portion thereof, may, e.g., be digested with one or more enzymes dissolved or mixed into a cell collection composition as described above.

In certain embodiments, the cell collection composition comprises one or more tissue-disruptive enzyme(s). Enzymatic digestion preferably uses a combination of enzymes, e.g., a combination of a matrix metalloprotease and a neutral protease, for example, a combination of dispase and collagenase, e.g., used in sequential order. When more than one protease is used, the proteases may be used at the same time to digest the amnion tissue, or may be used serially. In one embodiment, for example, the amnion tissue is digested three times with trypsin and then once with collagenase.

In one embodiment, amnion tissue is enzymatically digested with one or more of a matrix metalloprotease, a neutral protease, and a mucolytic enzyme. In a specific embodiment, the amnion tissue is digested with a combination of collagenase, dispase, and hyaluronidase. In another specific embodiment, the amnion tissue is digested with a combination of LIBERASE™ (Boehringer Mannheim Corp., Indianapolis, Ind.) and hyaluronidase. Other enzymes that can be used to disrupt amnion tissue include papain, deoxyribonucleases, serine proteases, such as trypsin, chymotrypsin, or elastase. Serine proteases may be inhibited by alpha 2 microglobulin in serum and therefore the medium used for digestion can, in certain embodiments, be serum-free. In certain other embodiments, EDTA and DNase are used in the digestion of amnion tissue, e.g., to increase the efficiency of cell recovery. In certain other embodiments, the digestate is diluted so as to avoid trapping cells within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to isolate amnion derived adherent cells. For example, in one embodiment, amnion tissue, or part thereof, is digested first with an appropriate amount of trypsin, at a concentration of about 0.25%, for, e.g., 15 minutes, at 37° C., followed by collagenase I at about 1 to about 2 mg/ml for, e.g., 45 minutes.

In one embodiment, amnion derived adherent cells can be obtained as follows. The amniotic membrane is cut into segments approximately 0.1"×0.1" to about 5"×5", e.g., 2"×2", in size. The epithelial monolayer is removed from the fetal side of the amniotic membrane by triple trypsinization as follows. The segments of amniotic membrane are placed into a container with warm (e.g., about 20° C. to about 37° C.) trypsin-EDTA solution (0.25%). The volume of trypsin can range from about 5 mL per gram of amnion to about 50 mL per gram of amnion. The container is agitated for about 5 minutes to about 30 minutes, e.g., 15 minutes, while maintaining the temperature constant. The segments of amniotic membrane are then separated from the trypsin solution by any appropriate method, such as manually removing the amnion segments, or by filtration. The trypsinization step can be repeated at least one more time.

Upon completion of the final trypsinization, the segments of amniotic membrane are placed back into the container filled with warm trypsin neutralization solution, such as phosphate-buffered saline (PBS)/10% FBS, PBS/5% FBS or PBS/3% FBS. The container is agitated for about 5 seconds to about 30 minutes, e.g., 5 minutes. The segments of amniotic membrane are then separated from the trypsin neutralization solution as described above, and the segments of amniotic membrane are placed into the container filled with warm PBS, pH 7.2. The container is agitated for about 5 seconds to about 30 minutes, and the amniotic membrane segments are then separated from the PBS as described above.

The segments of amniotic membrane are then placed into the container filled with warm (e.g., about 20° C. to about 37° C.) digestion solution. The volume of digestion solution can range from about 5 mL per gram of amnion to about 50 mL per gram of amnion. Digestion solutions comprise digestion enzymes in an appropriate culture medium, such as DMEM. Typical digestion solutions include collagenase type I (about 50 U/mL to about 500 U/mL); collagenase type I (about 50 U/mL to about 500 U/mL) plus dispase (about 5 U/mL to about 100 U/mL); and collagenase type I (about 50 U/mL to about 500 U/mL), dispase (about 2 U/mL to about 50 U/mL) and hyaluronidase (about 3 U/mL to about 10 U/mL). The container is agitated at 37° C. until amnion digestion is substantially complete (approximately 10 minutes to about 90 minutes). Warm PBS/5% FBS is then added to the container at a ratio of about 1 mL per gram of amniotic tissue to about 50 mL per gram of amniotic tissue. The container is agitated for about 2 minutes to about 5 minutes. The cell suspension is then filtered to remove any un-digested tissue using a 40 μm to 100 μm filter. The cells are suspended in warm PBS (about 1 mL to about 500 mL), and then centrifuged at 200×g to about 400×g for about 5 minutes to about 30 minutes, e.g. 300×g for about 15 minutes at 20° C. After centrifugation, the supernatant is removed and the cells are resuspended in a suitable culture medium. The cell suspension can be filtered (40 μm to 70 μm filter) to remove any remaining undigested tissue, yielding a single cell suspension.

In this embodiment, cells in suspension are collected and cultured as described elsewhere herein to produce isolated amnion derived adherent cells, and populations of such cells. The remaining undigested amnion, in this embodiment, can be discarded. The cells released from the amnion tissue can be, e.g., collected, e.g., by centrifugation, and cultured in standard cell culture medium.

In any of the digestion protocols herein, the cell suspension obtained by digestion can be filtered, e.g., through a filter comprising pores from about 50 μm to about 150 μm, e.g., from about 75 μm to about 125 μm. In a more specific embodiment, the cell suspension can be filtered through two or more filters, e.g., a 125 μm filter and a 75 μm filter.

In conjunction with any of the methods described herein, AMDACs can be isolated from the cells released during digestion by selecting cells that express one or more characteristics of AMDACs, as described in Section 5.1, above.

AMDACs can also, for example, be isolated using a specific two-step isolation method comprising digestion with trypsin followed by digestion with collagenase. Thus, in another aspect, provided herein is a method of isolating amnion derived adherent cells comprising digesting an amniotic membrane or portion thereof with trypsin such that epithelial cells are released from said amniotic membrane; removing the amniotic membrane or portion thereof from said epithelial cells; further digesting the amniotic membrane or portion thereof with collagenase such that amnion derived adherent cells are released from said amniotic membrane or portion thereof; and separating said amnion derived adherent cells from said amniotic membrane. In a specific embodiment, digestion of the amniotic membrane or portion thereof is repeated at least once. In another specific embodiment, digestion of the amniotic membrane or portion thereof with collagenase is repeated at least once. In another specific embodiment, the trypsin is at about 0.1%-1.0% (final concentration). In a more specific embodiment, the trypsin is at about 0.25% (final concentration). In another specific embodiment, the collagenase is at about 50 U/mL to about 1000 U/mL (final concentration). In a more specific embodiment, the collagenase is at about 125 U/mL (final concentration). In another specific embodiment, the method of isolation additionally comprises culturing said amnion derived adherent cells in cell culture and separating said amnion derived adherent cells from non-adherent cells in said culture to produce an enriched population of amnion derived adherent cells. In more specific embodiments, at least 50%, 55%, 60%, 65%, 70%, 75%, 80%, 85%, 90%, 95%, 98% or 99% of cells in said enriched population of amnion derived adherent cells are said amnion derived adherent cells.

In a more specific embodiment of the above methods, the amnion derived adherent cells are negative for OCT-4, as determined by RT-PCR, and one or more of HLA-G$^+$, CD90$^+$, CD105$^+$, and CD117$^-$, as determined by flow cytometry.

5.4.4 Isolation, Sorting, and Characterization of Amnion Derived Adherent Cells

Cell pellets can be resuspended in fresh cell collection composition, as described above, or a medium suitable for cell maintenance, e.g., Dulbecco's Modified Eagle's Medium (DMEM); Iscove's Modified Dulbecco's Medium (IMDM), e.g. IMDM serum-free medium containing 2 U/mL heparin and 2 mM EDTA (GibcoBRL, NY); a mixture of buffer (e.g. PBS, HBSS) with FBS (e.g. 2% v/v); or the like.

Amnion derived adherent cells that have been cultured, e.g., on a surface, e.g., on tissue culture plastic, with or without additional extracellular matrix coating such as fibronectin, can be passaged or isolated by differential adherence. For example, a cell suspension obtained from collagenase digestion of amnion tissue, performed as described in Section 5.4.3, above, can be cultured, e.g., for 3-7 days in culture medium on tissue culture plastic. During culture, a plurality of cells in the suspension adhere to the culture surface, and, after continued culture, give rise to amnion derived adherent cells. Nonadherent cells, which do not give rise to the amnion derived adherent cells, are removed during medium exchange.

The number and type of cells collected from amnion can be monitored, for example, by measuring changes in morphology and cell surface markers using standard cell detection techniques such as immunolocalization, e.g., flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using one or more antibodies to CD34, one can determine, using the techniques above, whether a cell comprises a detectable amount of CD34; if so, the cell is CD34+.

Amnion-derived cells, e.g., cells that have been isolated by Ficoll separation, differential adherence, or a combination of both, can be sorted using a fluorescence activated cell sorter (FACS). Fluorescence activated cell sorting (FACS) is a well-known method for separating particles, including cells, based on the fluorescent properties of the particles (see, e.g., Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, cells from placenta, e.g., amnion derived adherent cells, can be sorted on the basis of expression of the markers CD49f+, VEGFR2/KDR, and/or Flt-1/VNEGFR1. Preferably the cells are identified as being OCT-4−, e.g., by determining the expression of OCT-4 by RT-PCR in a sample of the cells, wherein the cells are OCT-4− if the cells in the sample fail to show detectable production of mRNA for OCT-4 after 30 cycles. For example, cells from amnion that are VEGFR2/KDR+ and VEGFR1/Flt-1+ can be sorted from cells that are one or more of VEGFR2/KDR−, and VEGFR1/Flt-1+, CD9, CD54, CD105+, CD200+, and/or VE-cadherin−. In a specific embodiment, amnion-derived, tissue culture plastic-adherent cells that are one or more of CD49f+, VEGFR2/KDR+, CD9+, CD54+, CD105+, CD200+, and/or VE-cadherin−, or cells that are VEGFR2/KDR+, CD9+, CD54+, CD105+, CD200+, and VE-cadherin−, are sorted away from cells not expressing one or more of such marker(s), and selected. In another specific embodiment, CD49f+, VEGFR2/KDR+, VEGFR1/Flt-1+ cells that are additionally one or more, or all, of CD31, CD34+, CD45+, CD133−, and/or Tie-2+ are sorted from cells that do not display one or more, or any, of such characteristics. In another specific embodiment, VEGFR2/KDR+, VEGFR1/Flt-1+ cells that are additionally one or more, or all, of CD9+, CD10+, CD44+, CD54+, CD98+, Tie-2+, TEM-7+, CD31−, CD34−, CD45−, CD133−, CD143−, CD146−, and/or CXCR4−, are sorted from cells that do not display one or more, or any, of such characteristics.

Selection for amnion derived adherent cells can be performed on a cell suspension resulting from digestion, or on isolated cells collected from digestate, e.g., by centrifugation or separation using flow cytometry. Selection by expressed markers can be accomplished alone or, e.g., in connection with procedures to select cells on the basis of their adherence properties in culture. For example, an adherence selection can be accomplished before or after sorting on the basis of marker expression.

With respect to antibody-mediated detection and sorting of placental cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against CD105 (available from R&D Systems Inc., Minneapolis, Minn.); phycoerythrin (PE) conjugated monoclonal antibodies against CD200 (BD Biosciences Pharmingen); VEGFR2/KDR-Biotin (CD309, Abcam), and the like. Antibodies to any of the markers disclosed herein can be labeled with any standard label for antibodies that facilitates detection of the antibodies, including, e.g., horseradish peroxidase, alkaline phosphatase, β-galactosidase, acetylcholinesterase streptavidin/biotin, avidin/biotin, umbelliferone, fluorescein, fluorescein isothiocyanate (FITC), rhodamine, dichlorotriazinylamine fluorescein, dansyl chloride or phycoerythrin (PE), luminol, luciferase, luciferin, and aequorin, and examples of suitable radioactive material include $^{125}I$, $^{131}I$, $^{35}S$ or $^{3}H$.

Amnion derived adherent cells can be labeled with an antibody to a single marker and detected and/sorted based on the single marker, or can be simultaneously labeled with multiple antibodies to a plurality of different markers and sorted based on the plurality of markers.

In another embodiment, magnetic beads can be used to separate cells, e.g., to separate the amnion derived adherent cells described herein from other amnion cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Amnion derived adherent cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay or MTT cell proliferation assay (to assess proliferation). Longevity may be determined by methods well known in the art, such as by determining the maximum number of population doubling in an extended culture.

Amnion derived adherent cells, can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.5 Culture of Amnion Derived Adherent Cells

5.5.1 Culture Media

Isolated amnion derived adherent cells, or populations of such cells, can be used to initiate, or seed, cell cultures. Cells are generally transferred to sterile tissue culture vessels either uncoated or coated with extracellular matrix or biomolecules such as laminin, collagen (e.g., native or denatured), gelatin, fibronectin, ornithine, vitronectin, and extracellular membrane protein (e.g., MATRIGEL™ (BD Discovery Labware, Bedford, Mass.)).

AMDACs can, for example, be established in media suitable for the culture of stem cells, Establishment media can, for example, include EGM-2 medium (Lonza), DMEM+10% FBS, or medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^4$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin (referred to herein as "standard medium").

Amnion derived adherent cells can be cultured in any medium, and under any conditions, recognized in the art as acceptable for the culture of cells, e.g., adherent placental stem cells. Preferably, the culture medium comprises serum. In various embodiments, media for the culture or subculture of AMDACs includes STEMPRO® (Invitrogen), MSCM-sf (ScienCell, Carlsbad, Calif.), MESENCULT®-ACF medium (StemCell Technologies, Vancouver, Canada), standard medium, standard medium lacking EGF, standard medium lacking PDGF, DMEM+10% FBS, EGM-2 (Lonza), EGM-2MV (Lonza), 2%, 10% and 20% ES media, ES-SSR medium, or α-MEM-20% FBS. Medium acceptable for the culture of amnion derived adherent cells includes, e.g., DMEM, IMDM, DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM Lonza), ADVANCESTEM™ Medium (Hyclone), KNOCKOUT™ DMEM (Invitrogen), Leibovitz's L-15 medium, MCDB, DMEM/F12, RPMI 1640, advanced DMEM (Gibco), DMEM/MCDB201 (Sigma), and CELL-GRO FREE, or the like. In various embodiments, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising about 2 to about 20%, e.g., about 10%, fetal bovine serum (FBS; e.g. defined fetal bovine serum, Hyclone, Logan Utah); DMEM-HG comprising about 2 to about 20%, e.g., about 15%, FBS; IMDM (Iscove's modified Dulbecco's medium) comprising about 2 to about 20%, e.g., about 10%, FBS, about 2 to about 20%, e.g., about 10%, horse serum, and hydrocortisone; M199 comprising about 2 to about 20%, e.g., about 10%, FBS, EGF, and heparin; α-MEM (minimal essential medium) comprising about 2 to about 20%, e.g., about 10%, FBS, GLUTAMAX™ and gentamicin; DMEM comprising 10% FBS, GLUTAMAX™ and gentamicin; DMEM-LG comprising about 2 to about 20%, e.g., about 15%, (v/v) fetal bovine serum (e.g., defined fetal bovine serum, Hyclone, Logan Utah), antibiotics/antimycotics (e.g., penicillin at about 100 Units/milliliter, streptomycin at 100 micrograms/milliliter, and/or amphotericin B at 0.25 micrograms/milliliter (Invitrogen, Carlsbad, Calif.)), and 0.001% (v/v) β-mercaptoethanol (Sigma, St. Louis Mo.); KNOCKOUT™-DMEM basal medium supplemented with 2 to 20% FBS, non-essential amino acid (Invitrogen), beta-mercaptoethanol, KNOCKOUT™ basal medium supplemented with KNOCKOUT™ Serum Replacement, alpha-MEM comprising 2 to 20% FBS, EBM2™ basal medium supplemented with EGF, VEGF, bFGF, R3-IGF-1, hydrocortisone, heparin, ascorbic acid, FBS, gentamicin), or the like.

The culture medium can be supplemented with one or more components including, for example, serum (e.g., FCS or FBS, e.g., about 2-20% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Amnion derived adherent cells (AMDACs) can be cultured in standard tissue culture conditions, e.g., in tissue culture dishes or multiwell plates. The cells can also be cultured using a hanging drop method. In this method, the cells are suspended at about $1\times10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the cells are cultured. AMDACs can also be cultured in standard or high-volume or high-throughput culture systems, such asT-flasks, Corning HYPERFLASK®, Cell Factories (Nunc), 1⁻, 2⁻, 4⁻, 10 or 40-Tray Cell stacks, and the like.

In one embodiment, amnion derived adherent cells are cultured in the presence of a compound that acts to maintain an undifferentiated phenotype in the cells. In a specific embodiment, the compound is a substituted 3,4-dihydropyridimol[4,5-d]pyrimidine. In a more specific embodiment, the compound is a compound having the following chemical structure:

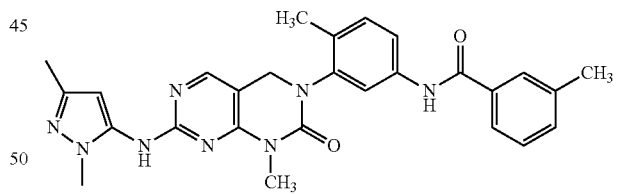

The compound can be contacted with an amnion derived adherent cell, or population of such cells, at a concentration of, for example, between about 1 μM to about 10 μM.

5.5.2 Expansion and Proliferation of Amnion Derived Adherent Cells

Once an isolated amnion derived adherent cell, or isolated population of such cells (e.g., amnion derived adherent cells, or population of such cells separated from at least 50% of the amnion cells with which the cell or population of cells is normally associated in vivo), the cells can be proliferated and expanded in vitro. For example, a population of adherent cells or amnion derived adherent cells can be cultured in tissue culture containers, e.g., dishes, flasks, multiwell plates, or the like, for a sufficient time for the cells to proliferate to 40-70% confluence, that is, until the cells and their progeny occupy 40-70% of the culturing surface area of the tissue culture container.

Amnion derived adherent cells can be seeded in culture vessels at a density that allows cell growth. For example, the cells may be seeded at low density (e.g., about 400 to about 6,000 cells/cm$^2$) to high density (e.g., about 20,000 or more cells/cm$^2$). In a preferred embodiment, the cells are cultured at about 0% to about 5% by volume $CO_2$ in air. In some preferred embodiments, the cells are cultured at about 0.1% to about 25% $O_2$ in air, preferably about 5% to about 20% $O_2$ in air. The cells are preferably cultured at about 25° C. to about 40° C., preferably at about 37° C.

The cells are preferably cultured in an incubator. During culture, the culture medium can be static or can be agitated, for example, during culture using a bioreactor. Amnion derived adherent cells preferably are grown under low oxidative stress (e.g., with addition of glutathione, ascorbic acid, catalase, tocopherol, N-acetylcysteine, or the like).

Although the amnion-derived angiogenic cells may be grown to confluence, the cells are preferably not grown to confluence. For example, once 40%-70% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 cells, preferably about 50,000 cells, or about 400 to about 6,000 cells/cm$^2$, can be passaged to a new culture container containing fresh culture medium. Typically, the new medium is the same type of medium from which the cells were removed. The amnion derived adherent cells can be passaged at least 1, 2, 3, 4, 5, 6, 7, 8, 9, 10, 11, 12, 13, 14, 15, 16, 17, 18, 19 or 20 times, or more. AMDACs can be doubled in culture at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 times, or more.

5.6 Preservation of Amnion Derived Adherent Cells

Amnion derived adherent cells can be preserved, that is, placed under conditions that allow for long-term storage, or conditions that inhibit cell death by, e.g., apoptosis or necrosis, e.g., during collection or prior to production of the compositions described herein, e.g., using the methods described herein.

Amnion derived adherent cells can be preserved using, e.g., a composition comprising an apoptosis inhibitor, necrosis inhibitor and/or an oxygen-carrying perfluorocarbon, as described in U.S. Application Publication No. 2007/0190042, the disclosure of which is hereby incorporated by reference in its entirety. In one embodiment, a method of preserving such cells, or a population of such cells, comprises contacting said cells or population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of cells, as compared to a population of cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of amnion derived adherent cells. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the cells. In another more specific embodiment, said apoptosis inhibitor and said perfluorocarbon are between about 2° C. and 10° C., or between about 2° C. and about 5° C., at the time of contacting the cells. In another more specific embodiment, said contacting is performed during transport of said population of cells. In another more specific embodiment, said contacting is performed during freezing and thawing of said population of cells.

Populations of amnion derived adherent cells can be preserved, e.g., by a method comprising contacting a population of said cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, amnion derived adherent cells are contacted with a cell collection composition comprising an apoptosis inhibitor and oxygen-carrying perfluorocarbon, organ-preserving compound, or combination thereof, during perfusion. In another embodiment, the amnion derived adherent cells are contacted with such a cell collection composition during a process of tissue disruption, e.g., enzymatic digestion of amnion tissue. In another embodiment, amnion derived adherent cells are contacted with said cell collection compound after collection by tissue disruption, e.g., enzymatic digestion of amnion tissue.

Typically, during collection of amnion derived adherent cells, enrichment and isolation, it is preferable to minimize or eliminate cell stress due to hypoxia and mechanical stress. In another embodiment of the method, therefore, an amnion derived adherent cell, or population of cells comprising the amnion derived adherent cells, is exposed to a hypoxic condition during collection, enrichment or isolation for less than six hours during said preservation, wherein a hypoxic condition is a concentration of oxygen that is, e.g., less than normal atmospheric oxygen concentration; less than normal blood oxygen concentration; or the like. In a more specific embodiment, said cells or population of said cells is exposed to said hypoxic condition for less than two hours during said preservation. In another more specific embodiment, said cells or population of said cells is exposed to said hypoxic condition for less than one hour, or less than thirty minutes, or is not exposed to a hypoxic condition, during collection, enrichment or isolation. In another specific embodiment, said population of cells is not exposed to shear stress during collection, enrichment or isolation.

Amnion derived adherent cells can be cryopreserved, in general or by the specific methods disclosed herein, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., cell freezing medium identified by SigmaAldrich catalog numbers C2695, C2639 (Cell Freezing Medium-Serum-free 1×, not containing DMSO) or C6039 (Cell Freezing Medium-Glycoerol 1× containing Minimum Essential Medium, glycerol, calf serum and bovine serum), Lonza PROFREEZE™ 2× Medium, methylcellulose, dextran, human serum albumin, fetal bovine serum, fetal calf serum, or Plasmalyte. Cryopreservation medium preferably comprises DMSO (dimethylsulfoxide) or glycerol, at a concentration of, e.g., about 1% to about 20%, e.g., about 5% to 10% (v/v), optionally including fetal bovine serum or human serum. Cryopreservation medium may comprise additional agents, for example, methylcellulose and/or glycerol. Isolated amnion derived adherent cells are preferably cooled at about 1° C./min during cryopreservation. A preferred cryopreservation temperature is about −80° C. to about −180° C., preferably about −125° C. to about −140° C. Cryopreserved cells can be transferred to vapor phase of liquid nitrogen prior to thawing for use. In some embodiments, for example, once the ampoules have reached about −80° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

5.7 Production of a Bank of Amnion Derived Adherent Cells

Amnion derived adherent cells can be cultured in a number of different ways to produce a set of lots, e.g., a set of individually-administrable doses, of such cells. Sets of lots of angiogenic amniotic cells, obtained from a plurality of placentas, can be arranged in a bank of cells for, e.g., long-term storage. Generally, amnion derived adherent cells are obtained from an initial culture of cells to form a seed culture, which is expanded under controlled conditions to form populations of cells from approximately equivalent numbers of doublings. Lots are preferably derived from the tissue of a single placenta, but can be derived from the tissue of a plurality of placentas.

In one non-limiting embodiment, lots or doses of amnion derived adherent cells are obtained as follows. Amnion tissue is first disrupted, e.g., digested as described in Section 5.4.3, above using serial trypsin and collagenase digestions. Cells from the collagenase-digested tissue are cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells can then be used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ adherent cells. Preferably, from about $1 \times 10^3$ to about $3 \times 10^4$ Passage 0 cells are used to seed each expansion culture. The number of expansion cultures can depend upon the number of Passage 0 cells, and may be greater or fewer in number depending upon the particular placenta(s) from which the adherent cells are obtained.

Expansion cultures can then be grown until the density of cells in culture reaches a certain value, e.g., about $1 \times 10^5$ cells/cm$^2$. Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 50 million cells per mL, and can comprise between about $10^6$ and about $10^{10}$ cells in total.

In one embodiment, therefore, a cell bank comprising amnion derived adherent cells can be made by a method comprising: expanding primary culture amnion derived adherent cells from a human post-partum placenta for a first plurality of population doublings; cryopreserving the cells to form a Master Cell Bank; optionally expanding a plurality of the cells from the Master Cell Bank for a second plurality of population doublings; cryopreserving the expanded cells to form a Working Cell Bank; optionally expanding a plurality of the expanded amnion derived adherent cells from the Working Cell Bank for a third plurality of population doublings; and cryopreserving the resulting expanded cells in individual doses, wherein said individual doses collectively compose a cell bank. The bank can comprise doses, or lots, of solely amnion derived adherent cells, or can comprise a combination of lots of amnion derived adherent cells and lots or doses of another kind of cell, e.g., another kind of stem or progenitor cell. Preferably, each individual dose comprises only amnion derived adherent cells. In another specific embodiment, all of said cells in said primary culture are from the same placenta. In another specific embodiment, said individual doses comprise from about $10^4$ to about $10^5$ cells. In another specific embodiment, said individual doses comprise from about $10^5$ to about $10^6$ cells. In another specific embodiment, said individual doses comprise from about $10^6$ to about $10^7$ cells. In another specific embodiment, said individual doses comprise from about $10^7$ to about $10^8$ cells. In another specific embodiment, said individual doses comprise from about $10^8$ to about $10^9$ cells. In another specific embodiment, said individual doses comprise from about $10^9$ to about $10^{10}$ cells.

In certain embodiments, amnion derived adherent cells can be thawed from a Working Cell Bank and cultured for a plurality of population doublings. When a desired number of cells is generated, or a desired number of population doublings has taken place, the adherent cells can be collected, e.g., by centrifugation, and resuspended in a solution comprising, e.g., dextran, e.g., 5% dextran. In certain embodiments, the dextran is dextran-40. In certain embodiments, the cells are collected a second time and resuspended in a solution comprising dextran and a cryopreservant, e.g., a 5% dextran (e.g., dextran-40) solution comprising 10% HSA and 2%-20%, e.g., 5% DMSO, and cryopreserved. The cryopreserved amnion derived adherent cells can be thawed, e.g., immediately before use.

In a preferred embodiment, the donor from which the placenta is obtained (e.g., the mother) is tested for at least one pathogen. In certain embodiments, if the mother tests positive for a tested pathogen, the entire lot from the placenta is discarded. Such testing can be performed at any time during production of lots of amnion derived adherent cells, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.8 Uses of Amnion Derived Adherent Cells

Provided herein are compositions comprising amnion derived adherent cells. Examples of such compositions include pharmaceutical compositions (see Section 5.8.1, below); matrices and scaffolds (see Section 5.8.2, below), and media conditioned by amnion derived adherent cells (see Section 5.8.3, below).

5.8.1 Compositions Comprising Amnion Derived Adherent Cells

In certain embodiments, amnion derived adherent cells are contained within, or are components of, a pharmaceutical composition. The cells can be prepared in a form that is easily administrable to an individual, e.g., amnion derived adherent cells that are contained within a container that is suitable for medical use. Such a container can be, for example, a syringe, sterile plastic bag, flask, jar, or other container from which the anion derived angiogenic cell population can be easily dispensed. For example, the container can be a blood bag or other plastic, medically-acceptable bag suitable for the intravenous administration of a liquid to a recipient. The container, in certain embodiments, is one that allows for cryopreservation of the cells. The cells in the compositions, e.g., pharmaceutical compositions, provided herein, can comprise amnion derived adherent cells derived from a single donor, or from multiple donors. The cells can be completely HLA-matched to an intended recipient, or partially or completely HLA-mismatched.

Thus, in one embodiment, amnion derived adherent cells in the compositions provided herein are administered to an individual in need thereof in the form of a composition comprising amnion derived adherent cells in a container. In another specific embodiment, the container is a bag, flask, or jar. In more specific embodiment, said bag is a sterile plastic bag. In a more specific embodiment, said bag is suitable for, allows or facilitates intravenous administration of said adherent cells, e.g., by intravenous infusion, bolus injection, or the like. The bag can comprise multiple lumens or compartments that are interconnected to allow mixing of the cells and one or more other solutions, e.g., a drug, prior to, or during, administration. In another specific embodiment, prior to cryopreservation, the solution comprising the amnion derived adherent cells comprises one or more compounds that facilitate cryopreservation of the cells. In another specific embodiment, said amnion derived adherent cells are contained within a physiologically-acceptable aqueous solution. In a more specific embodiment, said physiologically-acceptable aqueous solution is a 0.9% NaCl solution. In another specific embodiment, said amnion derived adherent cells comprise placental cells that are HLA-matched to a recipient of said cells. In another specific embodiment, said amnion derived adherent cells comprise cells that are at least partially HLA-mismatched to a recipient of said cells. In another specific embodiment, said amnion derived adherent cells are derived from a plurality of donors. In various specific embodiments, said container comprises about, at least, or at most $1\times10^6$ said cells, $5\times10^6$ said cells, $1\times10^7$ said stem cells, $5\times10^7$ said cells, $1\times10^8$ said cells, $5\times10^8$ said cells, $1\times10^9$ said cells, $5\times10^9$ said cells, or $1\times10^{10}$ said cells. In other specific embodiments of any of the foregoing cryopreserved populations, said cells have been passaged about, at least, or no more than 5 times, no more than 10 times, no more than 15 times, or no more than 20 times. In another specific embodiment of any of the foregoing cryopreserved cells, said cells have been expanded within said container. In specific embodiments, a single unit dose of amnion derived adherent cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more amnion derived adherent cells.

In certain embodiments, the pharmaceutical compositions provided herein comprises populations of amnion derived adherent cells, that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

5.8.2 Matrices Comprising Amnion Derived Adherent Cells

Further provided herein are compositions comprising matrices, hydrogels, scaffolds, and the like. Such compositions can be used in the place of, or in addition to, such cells in liquid suspension.

The matrix can be, e.g., a permanent or degradable decellularized tissue, e.g., a decellularized amniotic membrane, or a synthetic matrix. The matrix can be a three-dimensional scaffold. In a more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, a cytokine, an antibody, or an organic molecule of less than 5,000 daltons.

The amnion derived adherent cells described herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% H$_2$O) amniotic membrane, chorionic membrane, substantially dry chorionic membrane, substantially dry amniotic and chorionic membrane, and the like. Preferred placental biomaterials on which the amnion derived adherent cells provided herein can be seeded are described in Hariri, U.S. Application Publication No. 2004/0048796, the disclosure of which is incorporated by reference herein in its entirety.

In another specific embodiment, the matrix is a composition comprising an extracellular matrix. In a more specific embodiment, said composition is MATRIGEL™ (BD Biosciences).

The isolated amnion derived adherent cells described herein can be suspended in a hydrogel solution suitable for, e.g., injection. The hydrogel is, e.g., an organic polymer (natural or synthetic) that is cross-linked via covalent, ionic, or hydrogen bonds to create a three-dimensional open-lattice structure that entraps water molecules to form a gel. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. The amnion derived adherent cells in such a matrix can also be cultured so that the cells are mitotically expanded, e.g., prior to implantation. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In certain embodiments, the compositions comprising cells, provided herein, comprise an in situ polymerizable gel (see, e.g., U.S. Patent Application Publication 2002/0022676; Anseth et al., *J. Control Release,* 78(1-3): 199-209 (2002); Wang et al., *Biomaterials,* 24(22):3969-80 (2003). In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly (phosphazenes), poly(acrylic acids), poly(methacrylic acids), copolymers of acrylic acid and methacrylic acid, poly (vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

In a specific embodiment, the matrix is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another preferred embodiment the cells of the invention are seeded onto foam scaffolds that may be composite structures. In addition, the three-dimensional framework may be molded into a useful shape, such as a specific structure in the body to be repaired, replaced, or augmented. Other examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

The amnion derived adherent cells described herein can be seeded onto a three-dimensional framework or scaffold and implanted in vivo. Such a framework can be implanted in combination with any one or more growth factors, cells, drugs or other components that, e.g., stimulate tissue formation, e.g., bone formation or formation of vasculature.

The placental amnion derived adherent cells provided herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the matrix comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The matrix can also comprise anti-thrombotic agents such as heparin; the scaffolds can also be treated to alter the surface charge (e.g., coating with plasma) prior to seeding with the adherent cells provided herein.

The framework may be treated prior to inoculation of the amnion derived adherent cells provided herein in order to enhance cell attachment. For example, prior to inoculation with the cells of the invention, nylon matrices could be treated with 0.1 molar acetic acid and incubated in polylysine, PBS, and/or collagen to coat the nylon. Polystyrene can be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, or plant gums.

In some embodiments, the matrix comprises or is treated with materials that render the matrix non-thrombogenic, e.g., natural materials such as basement membrane proteins such as laminin and Type IV collagen, and synthetic materials such as ePTFE or segmented polyurethaneurea silicones, such as PURSPAN (The Polymer Technology Group, Inc., Berkeley, Calif.). Such materials can be further treated to render the scaffold non-thrombogenic, e.g., with heparin, and treatments that alter the surface charge of the material, such as plasma coating.

The therapeutic cell compositions comprising amnion derived adherent cells can also be provided in the form of a matrix-cell complex. Matrices can include biocompatible scaffolds, lattices, self-assembling structures and the like, whether bioabsorbable or not, liquid, gel, or solid. Such matrices are known in the arts of therapeutic cell treatment, surgical repair, tissue engineering, and wound healing. In certain embodiments, the cells adhere to the matrix. In other embodiments, the cells are entrapped or contained within matrix spaces. Most preferred are those matrix-cell complexes in which the cells grow in close association with the matrix and when used therapeutically, stimulate and support ingrowth of a recipient's cells, or stimulate or support angiogenesis. The matrix-cell compositions can be introduced into an individual's body in any way known in the art, including but not limited to implantation, injection, surgical attachment, transplantation with other tissue, injection, and the like. In some embodiments, the matrices form in vivo, or in situ. For example, in situ polymerizable gels can be used in accordance with the invention. Examples of such gels are known in the art.

In some embodiments, the cells provided herein are seeded onto such three-dimensional matrices, such as scaffolds and implanted in vivo, where the seeded cells may proliferate on or in the framework or help establish replacement tissue in vivo with or without cooperation of other cells. Growth of the amnion derived adherent cells or co-cultures thereof on the three-dimensional framework preferably results in the formation of a three-dimensional tissue, or foundation thereof, which can be utilized in vivo, for example for repair of damaged or diseased tissue. For example, the three-dimensional scaffolds can be used to form tubular structures, for example for use in repair of blood vessels; or aspects of the circulatory system or coronary structures. In accordance with one aspect of the invention, amnion derived adherent cells, or co-cultures thereof, are inoculated, or seeded on a three-dimensional framework or matrix, such as a scaffold, a foam or hydrogel. The framework may be configured into various shapes such as generally flat, generally cylindrical or tubular, or can be completely free-form as may be required or desired for the corrective structure under consideration. In some embodiments, the amnion derived adherent cells grow on the three dimensional structure, while in other embodiments, the cells only survive, or even die, but stimulate or promote ingrowth of new tissue or vascularization in a recipient.

The cells of the invention can be grown freely in culture, removed from the culture and inoculated onto a three-dimensional framework. Inoculation of the three-dimensional framework with a concentration of cells, e.g., approximately $10^6$ to $5\times10^7$ cells per milliliter, preferably results in the establishment of the three-dimensional support in relatively shorter periods of time. Moreover in some application it may be preferably to use a greater or lesser number of cells depending on the result desired.

In a specific embodiment, the matrix can be cut into a strip (e.g., rectangular in shape) of which the width is approximately equal to the inner circumference of a tubular organ into which it will ultimately be inserted. The amnion derived adherent cells can be inoculated onto the scaffold and incubated by floating or suspending in liquid media. At the appropriate stage of confluence, the scaffold can be rolled up into a tube by joining the long edges together. The seam can then be closed by suturing the two edges together using fibers of a suitable material of an appropriate diameter. In order to prevent cells from occluding the lumen, one of the open ends of the tubular framework can be affixed to a nozzle. Liquid media can be forced through the nozzle from a source chamber connected to the incubation chamber to create a current through the interior of the tubular framework. The other open end can be affixed to an outflow aperture which leads into a collection chamber from which the media can be recirculated through the source chamber. The tube can be detached from the nozzle and outflow aperture when incubation is complete. See, e.g., International Application No. WO 94/25584.

In general, two three-dimensional frameworks can be combined into a tube in accordance with the invention using any of the following methods. Two or more flat frameworks can be laid atop another and sutured together. The resulting two-layer sheet can then be rolled up, and, as described above, joined together and secured. In certain embodiments, one tubular scaffold that is to serve as the inner layer can be inoculated with amnion derived adherent cells and incubated. A second scaffold can be grown as a flat strip with width slightly larger than the outer circumference of the tubular framework. After appropriate growth is attained, the flat framework is wrapped around the outside of the tubular scaffold followed by closure of the seam of the two edges of the flat framework and securing the flat framework to the inner tube. In another embodiment, two or more tubular meshes of slightly differing diameters can be grown separately. The framework with the smaller diameter can be inserted inside the larger one and secured. For each of these methods, more layers can be added by reapplying the method to the double-layered tube. The scaffolds can be combined at any stage of growth of the amnion derived adherent cells, and incubation of the combined scaffolds can be continued when desirable.

In conjunction with the above, the cells and therapeutic compositions provided herein can be used in conjunction with implantable devices. For example the amnion derived adherent cells can be coadminstered with, for example, stents, artificial valves, ventricular assist devices, Guglielmi detachable coils and the like. As the devices may constitute the dominant therapy provided to an individual in need of such therapy, the cells and the like may be used as supportive or secondary therapy to assist in, stimulate, or promote proper healing in the area of the implanted device. The cells and therapeutic compositions of the invention may also be used to pretreat certain implantable devices, to minimize problems when they are used in vivo. Such pretreated devices, including coated devices, may be better tolerated by patients receiving them, with decrease risk of local or systemic infection, or for example, restenosis or further occlusion of blood vessels.

5.8.3 Media Conditioned by Amnion Derived Adherent Cells

Further provided herein is medium that has been conditioned by amnion derived adherent cells, that is, medium comprising one or more biomolecules secreted or excreted by the adherent cells. In various embodiments, the conditioned medium comprises medium in which the cells have grown for at least 1, 2, 3, 4, 5, 6, 7, 8, 9, 10, 11, 12, 13, 14 or more days, or for at least 1, 2, 3, 4, 5, 6, 7, 8, 9, 10, 11, 12, 13, 14, 15, 16, 17, 18, 19, or 20 population doublings, or more. In other embodiments, the conditioned medium comprises medium in which amnion derived adherent cells have grown to at least 30%, 40%, 50%, 60%, 70%, 80%, 90% confluence, or up to 100% confluence. Such conditioned medium can be used to support the culture of a population of cells, e.g., stem cells, e.g., placental stem cells, embryonic stem cells, embryonic germ cells, adult stem cells, or the like. In another embodiment, the conditioned medium comprises medium in which amnion derived adherent cells, and cells that are not amnion derived adherent cells, have been cultured together.

The conditioned medium can comprise the adherent cells provided herein. Thus, provided herein is a cell culture comprising amnion derived adherent cells. In a specific embodiment, the conditioned medium comprises a plurality, e.g., a population, of amnion derived adherent cells.

5.9 Modified Amnion Derived Adherent Cells 5.9.1 Genetically Modified Amnion Derived Adherent Cells In another aspect, the amnion derived adherent cells described herein can be genetically modified, e.g., to produce a nucleic acid or polypeptide of interest, or to produce a differentiated cell, e.g., an osteogenic cell, myocytic cell, pericytic cell, or angiogenic cell, that produces a nucleic acid or polypeptide of interest. For example, the amnion derived adherent cells can be modified to produce angiogenic factors, such as proangiogenic molecules, soluble factors and receptors or promigratory molecules such as chemokines, e.g., stromal cell derived factor 1 (SDF-1) or chemokine receptors. Genetic modification can be accomplished, e.g., using virus-based vectors including, but not limited to, non-integrating replicating vectors, e.g., papilloma virus vectors, SV40 vectors, adenoviral vectors; integrating viral vectors, e.g., retrovirus vector or adeno-associated viral vectors; or replicationdefective viral vectors. Other methods of introducing DNA into cells include the use of liposomes, electroporation, a particle gun, direct DNA injection, or the like.

The adherent cells provided herein can be, e.g., transformed or transfected with DNA controlled by or in operative association with, one or more appropriate expression control elements, for example, promoter or enhancer sequences, transcription terminators, polyadenylation sites, internal ribosomal entry sites. Preferably, such a DNA incorporates a selectable marker. Following the introduction of the foreign DNA, engineered adherent cells can be, e.g., grown in enriched media and then switched to selective media. In one embodiment, the DNA used to engineer a amnion derived adherent cell comprises a nucleotide sequence encoding a polypeptide of interest, e.g., a cytokine, growth factor, differentiation agent, or therapeutic polypeptide.

The DNA used to engineer the adherent cell can comprise any promoter known in the art to drive expression of a nucleotide sequence in mammalian cells, e.g., human cells. For example, promoters include, but are not limited to, CMV promoter/enhancer, SV40 promoter, papillomavirus promoter, Epstein-Barr virus promoter, elastin gene promoter, and the like. In a specific embodiment, the promoter is regulatable so that the nucleotide sequence is expressed only when desired. Promoters can be either inducible (e.g., those associated with metallothionein and heat shock proteins) or constitutive.

In another specific embodiment, the promoter is tissue-specific or exhibits tissue specificity. Examples of such promoters include but are not limited to myosin light chain-2 gene control region (Shani, 1985, Nature 314:283) (skeletal muscle).

The amnion derived adherent cells disclosed herein may be engineered or otherwise selected to "knock out" or "knock down" expression of one or more genes in such cells. The expression of a gene native to a cell can be diminished by, for example, inhibition of expression by inactivating the gene completely by, e.g., homologous recombination. In one embodiment, for example, an exon encoding an important region of the protein, or an exon 5' to that region, is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084). Antisense, morpholinos, DNAzymes, small interfering RNA, short hairpin RNA, and ribozyme molecules that inhibit expression of the target gene can also be used to reduce the level of target gene activity in the adherent cells. For example, antisense RNA molecules which inhibit the expression of major histocompatibility gene complexes (HLA) have been shown to be most versatile with respect to immune responses. Triple helix molecules can be utilized in reducing the level of target gene activity. See, e.g., L. G. Davis et al. (eds), 1994, BASIC METHODS IN MOLECULAR BIOLOGY, 2nd ed., Appleton & Lange, Norwalk, Conn., which is incorporated herein by reference.

In a specific embodiment, the amnion derived adherent cells disclosed herein can be genetically modified with a nucleic acid molecule comprising a nucleotide sequence encoding a polypeptide of interest, wherein expression of the polypeptide of interest is controllable by an exogenous factor, e.g., polypeptide, small organic molecule, or the like. The polypeptide of interest can be a therapeutic polypeptide. In a more specific embodiment, the polypeptide of interest is IL-12 or interleukin-1 receptor antagonist (IL-Ra). In another more specific embodiment, the polypeptide of interest is a fusion of interleukin-1 receptor antagonist and dihydrofolate reductase (DHFR), and the exogenous factor is an antifolate, e.g., methotrexate. Such a construct is useful in the engineering of amnion derived adherent cells that express IL-1Ra, or a fusion of IL-1Ra and DHFR, upon contact with methotrexate. Such a construct can be used, e.g., in the treatment of rheumatoid arthritis. In this embodiment, the fusion of IL-1Ra and DHFR is translationally upregulated upon exposure to an antifolate such as methotrexate. Therefore, in another specific embodiment, the nucleic acid used to genetically engineer an amnion derived adherent cell can comprise nucleotide sequences encoding a first polypeptide and a second polypeptide, wherein said first and second polypeptides are expressed as a fusion protein that is translationally upregulated in the presence of an exogenous factor. The polypeptide can be expressed transiently or long-term (e.g., over the course of weeks or months). Such a nucleic acid molecule can additionally comprise a nucleotide sequence encoding a polypeptide that allows for positive selection of engineered cells, or allows for visualization of the engineered cells. In another more specific embodiment, the nucleotide sequence encodes a polypeptide that is, e.g., fluorescent under appropriate visualization conditions, e.g., luciferase (Luc). In a more specific embodiment, such a nucleic acid molecule can comprise IL-1Ra-DHFR-IRES-Luc, where IL-Ra is interleukin-1 receptor antagonist, IRES is an internal ribosomal entry site, and DHFR is dihydrofolate reductase.

5.9.2 Immortalized Amnion Derived Adherent Cell Lines

Mammalian amnion derived adherent cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus. In another embodiment, amnion derived adherent cells can be immortalized using cre-lox recombination, as exemplified for a human pancreatic β-cell line by Narushima, M., et al (*Nature Biotechnology*, 2005, 23(10:1274-1282).

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present methods. Cells carrying neo$^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized amnion derived adherent cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized adherent cell line prepared as described above. In general, such clonal cell lines may be isolated using standard techniques, such as by limit dilution or using cloning rings, and expanded. Clonal cell lines may generally be fed and passaged as described above.

Conditionally-immortalized human amnion derived adherent cells lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.10 Methods of Treatment Using Amnion Derived Adherent Cells 5.10.1 Circulatory System Diseases The amnion derived adherent cells, populations of such cells, and populations of cells comprising amnion derived adherent cells, provided herein, can be used to treat individuals exhibiting a variety of disease states or conditions that would benefit from angiogenesis. Examples of such disease states or conditions include myocardial infarction, stroke, congestive heart failure, peripheral artery disease, hypoplastic left heart syndrome, diabetic ulcer, decubitus ulcer, venous ulcer, arterial ulcer, burn, non-union fracture, tumor-associated bone loss, osteoarthritis and maxillofacial bone repair. The amnion derived adherent cells, and populations of such cells, can also be used to promote angiogenesis in individuals exhibiting traumatic tissue loss or to prevent scar formation, or in individuals having total joint replacement or dental prosthetics.

In a more specific embodiment, the amnion derived adherent cells, and populations of such cells, provided herein, can be used to treat an individual having an insufficiency of the circulatory system, e.g., and individual having peripheral vascular disease or coronary artery disease.

In one aspect, provided herein are methods for treating a patient with a heart disease or injury comprising administering a therapeutic cell composition to a patient with a disease or injury of the heart or circulatory system, and evaluating the patient for improvements in cardiac function, wherein said cell composition comprises amnion derived adherent cells as described herein. In one embodiment, the heart disease is a cardiomyopathy. In specific embodiments, the cardiomyopathy is either idiopathic or a cardiomyopathy with a known cause. In other specific embodiments, the cardiomyopathy is either ischemic or nonischemic in nature. In another embodiments, the disease of the heart or circulatory system comprises one or more of angioplasty, aneurysm, angina (angina pectoris), aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, cardiomyopathy, carditis, carotid artery disease, coarctation of the aorta, congenital heart diseases (congenital heart defects), congestive heart failure (heart failure), coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocardial infarction (heart attacks), myocarditis, paroxysmal atrial tachycardia (PAT), periarteritis nodosa (polyarteritis, polyarteritis nodosa), pericarditis, peripheral vascular disease, critical limb ischemia, diabetic vasculopathy, phlebitis, pulmonary valve stenosis (pulmonic stenosis), Raynaud's Disease, renal artery stenosis, renovascular hypertension, rheumatic heart disease, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, or endocardial cushion defect.

In other embodiments, the disease of the heart or circulatory system comprises one or more of acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, diseases of pulmonary circulation (acute pulmonary heart disease, pulmonary embolism, chronic pulmonary heart disease), kyphoscoliotic heart disease, myocarditis, endocarditis, endomyocardial fibrosis, endocardial fibroelastosis, atrioventricular block, cardiac dysrhythmias, myocardial degeneration, diseases of the circulatory system including cerebrovascular disease, occlusion and stenosis of precerebral arteries, occlusion of cerebral arteries, diseases of arteries, arterioles and capillaries (atherosclerosis, aneurysm), or diseases of veins and lymphatic vessels.

In one embodiment, treatment comprises treatment of a patient with a cardiomyopathy with a therapeutic cell composition comprising amnion derived adherent cells, either with or without another cell type. In other preferred embodiments, the patient experiences benefits from the therapy, for example from the ability of the cells to support the growth of other cells, including stem cells or progenitor cells present in the heart, from the tissue ingrowth or vascularization of the tissue, and from the presence of beneficial cellular factors, chemokines, cytokines and the like, but the cells do not integrate or multiply in the patient. In another embodiment, the patient benefits from the therapeutic treatment with the cells, but the cells do not survive for a prolonged period in the patient. In one embodiment, the cells gradually decline in number, viability or biochemical activity, in other embodiments, the decline in cells may be preceded by a period of activity, for example growth, division, or biochemical activity. In other embodiments, senescent, nonviable or even dead cells are able to have a beneficial therapeutic effect.

Improvement in an individual having a disease or disorder of the circulatory system, wherein the individual is administered the amnion derived adherent cells or therapeutic compositions provided herein, can be assessed or demonstrated by detectable improvement in one or more symptoms of the disease or disorder of the circulatory system.

In another embodiment, improvement in an individual having a disease or disorder of the circulatory system, wherein the individual is administered the amnion derived adherent cells or therapeutic compositions provided herein, can be assessed or demonstrated by detectable improvement in one or more, indicia of cardiac function, for example, demonstration of detectable improvement in one or more of chest cardiac output (CO), cardiac index (CI), pulmonary artery wedge pressures (PAWP), and cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (e.g. dP/dt), pressure-volume loops, measurements of cardiac work, an increase in atrial or ventricular functioning; an increase in pumping efficiency, a decrease in the rate of loss of pumping efficiency, a decrease in loss of hemodynamic functioning; and a decrease in complications associated with cardiomyopathy, as compared to the individual prior to administration of amnion derived adherent cells.

Improvement in an individual receiving the therapeutic compositions provided herein can also be assessed by subjective metrics, e.g., the individual's self-assessment about his or her state of health following administration.

Success of administration of the cells is not, in certain embodiments, based on survival in the individual of the administered amnion derived adherent cells. Success is, instead, based on one or more metrics of improvement in cardiac or circulatory health, as noted above. Thus, the cells need not integrate and beat with the patient's heart, or into blood vessels.

In certain embodiments, the methods of treatment provided herein comprise inducing the therapeutic amnion derived adherent cells to differentiate along mesenchymal lineage, e.g., towards a cardiomyogenic, angiogenic or vasculogenic phenotype, or into cells such as myocytes, cardiomyocytes, endothelial cells, myocardial cells, epicardial cells, vascular endothelial cells, smooth muscle cells (e.g. vascular smooth muscle cells).

Administration of amnion derived adherent cells, or therapeutic compositions comprising such cells, to an individual in need thereof, can be accomplished, e.g., by transplantation, implantation (e.g., of the cells themselves or the cells as part of a matrix-cell combination), injection (e.g., directly to the site of the disease or condition, for example, directly to an ischemic site in the heart of an individual who has had a myocardial infarction), infusion, delivery via catheter, or any other means known in the art for providing cell therapy.

In one embodiment, the therapeutic cell compositions are provided to an individual in need thereof, for example, by injection into one or more sites in the individual. In a specific embodiment, the therapeutic cell compositions are provided by intracardiac injection, e.g., to an ischemic area in the heart. In other specific embodiments, the cells are injected onto the surface of the heart, into an adjacent area, or even to a more remote area. In preferred embodiments, the cells can home to the diseased or injured area.

An individual having a disease or condition of the coronary or vascular systems can be administered amnion derived adherent cells at any time the cells would be therapeutically beneficial. In certain embodiments, for example, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of the myocardial infarction. Administration proximal in time to a myocardial infarction, e.g., within 1-3 or 1-7 days, is preferable to administration distal in time, e.g., after 3 or 7 days after a myocardial infarction. In other embodiments, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of initial diagnosis of the disease or condition.

Also provided herein are kits for use in the treatment of myocardial infarction. The kits provide the therapeutic cell composition which can be prepared in a pharmaceutically acceptable form, for example by mixing with a pharmaceutically acceptable carrier, and an applicator, along with instructions for use. Ideally the kit can be used in the field, for example in a physician's office, or by an emergency care provider to be applied to a patient diagnosed as having had a myocardial infarction or similar cardiac event.

In specific embodiments of the methods of treatment provided herein, the amnion derived adherent cells are administered with stem cells (that is, stem cells that are not amnion derived adherent cells), myoblasts, myocytes, cardiomyoblasts, cardiomyocytes, or progenitors of myoblasts, myocytes, cardiomyoblasts, and/or cardiomyocytes.

In a specific embodiment, the methods of treatment provided herein comprise administering amnion derived adherent cells, e.g., a therapeutic composition comprising the cells, to a patient with a disease of the heart or circulatory system; and evaluating the patient for improvements in cardiac function, wherein the therapeutic cell composition is administered as a matrix-cell complex. In certain embodiments, the matrix is a scaffold, preferably bioabsorbable, comprising at least the cells.

To this end, provided herein are populations of amnion derived adherent cells incubated in the presence of one or more factors which stimulate stem or progenitor cell differentiation along a cardiogenic, angiogenic, hemangiogenic, or vasculogenic pathway. Such factors are known in the art; determination of suitable conditions for differentiation can be accomplished with routine experimentation. Such factors include, but are not limited to factors, such as growth factors, chemokines, cytokines, cellular products, demethylating agents, and other stimuli which are now known or later determined to stimulate differentiation, for example of stem cells, along cardiogenic, angiogenic, hemangiogenic, or vasculogenic pathways or lineages.

Amnion derived adherent cells may be differentiated along cardiogenic, angiogenic, hemangiogenic, or vasculogenic pathways or lineages by culture of the cells in the presence of factors comprising at least one of a demethylation agent, a BMP, FGF, Wnt factor protein, Hedgehog, and/or anti-Wnt factors.

Inclusion of demethylation agents tends to allow the cells to differentiate along mesenchymal lines, toward a cardiomyogenic pathway. Differentiation can be determined by, for example, expression of at least one of cardiomyosin, skeletal myosin, or GATA4; or by the acquisition of a beating rhythm, spontaneous or otherwise induced; or by the ability to integrate at least partially into a patient's cardiac muscle without inducing arrhythmias. Demethylation agents that can be used to initiate such differentiation include, but are not limited to, 5-azacytidine, 5-aza-2'-deoxycytidine, dimethylsulfoxide, chelerythrine chloride, retinoic acid or salts thereof, 2-amino-4-(ethylthio)butyric acid, procainamide, and procaine.

In certain embodiments herein, cells induced with one or more factors as identified above may become cardiomyogenic, angiogenic, hemangiogenic, or vasculogenic cells, or progenitors. Preferably at least some of the cells can integrate at least partially into a recipient's cardiovascular system, including but not limited to heart muscle, vascular and other structures of the heart, cardiac or peripheral blood vessels, and the like. In certain other embodiments, the differentiated amnion derived adherent cells differentiate into cells acquiring two or more of the indicia of cardiomyogenic cells or their progenitors, and able to partially or fully integrate into a recipient's heart or vasculature. In specific embodiments, the cells, which administered to an individual, result in no increase in arrhythmias, heart defects, blood vessel defects or other anomalies of the individual's circulatory system or health. In certain embodiments, the amnion derived adherent cells act to promote the differentiation of stem cells naturally present in the patient's cardiac muscle, blood vessels, blood and the like to themselves differentiate into for example, cardiomyocytes, or at least along cardiomyogenic, angiogenic, hemangiogenic, or vasculogenic lines.

Amnion derived adherent cells, and populations of such cells, can be provided therapeutically or prophylactically to an individual, e.g., an individual having a disease, disorder or condition of, or affecting, the heart or circulatory system. Such diseases, disorders or conditions can include congestive heart failure due to atherosclerosis, cardiomyopathy, or cardiac injury, e.g., an ischemic injury, such as from myocardial infarction or wound (acute or chronic).

In certain embodiments, the individual is administered a therapeutically effective amount of amnion derived adherent cells, e.g., in a population of cells that comprise the amnion derived adherent cells. In a specific embodiment, the population comprises about 50% amnion derived adherent cells. In another specific embodiment, the population is a substantially homogeneous population of amnion derived adherent cells. In other embodiments the population comprises at least about 5%, 10%, 20%, 25%, 30%, 33%, 40%, 60%, 66%, 70%, 75%, 80%, or 90% amnion derived adherent cells.

The amnion derived adherent cells may be administered to an individual in the form of a therapeutic composition comprising the cells and another therapeutic agent, such as insulin-like growth factor (IGF), platelet-derived growth factor (PDGF), epidermal growth factor (EGF), fibroblast growth factor (FGF), vascular endothelial growth factor (VEGF), hepatocyte growth factor (HGF), IL-8, an antithrombogenic agent (e.g., heparin, heparin derivatives, urokinase, and PPack (dextrophenylalanine proline arginine chloromethylketone); antithrombin compounds, platelet receptor antagonists, anti-thrombin antibodies, anti-platelet receptor antibodies, aspirin, dipyridamole, protamine, hirudin, prostaglandin inhibitors, and/or platelet inhibitors), an antiapoptotic agent (e.g., EPO, EPO derivatives and analogs, and their salts, TPO, IGF-I, IGF-II, hepatocyte growth factor (HGF), or caspase inhibitors), an anti-inflammatory agent (e.g., P38 MAP kinase inhibitors, statins, IL-6 and IL-1 inhibitors, Pemirolast, Tranilast, Remicade, Sirolimus, nonsteroidal anti-inflammatory compounds, for example, acetylsalicylic acid, ibuprofen, Tepoxalin, Tolmetin, or Suprofen), an immunosuppressive or immunomodulatory agent (e.g., calcineurin inhibitors, for example cyclosporine, Tacrolimus, mTOR inhibitors such as Sirolimus or Everolimus; anti-proliferatives such as azathioprine and mycophenolate mofetil; corticosteroids, e.g., prednisolone or hydrocortisone; antibodies such as monoclonal anti-IL-2Ra receptor antibodies, Basiliximab, Daclizuma, polyclonal anti-T-cell antibodies such as anti-thymocyte globulin (ATG), anti-lymphocyte globulin (ALG), and the monoclonal anti-T cell antibody OKT3, or adherent placental stem cells as described in U.S. Pat. No. 7,468,276, and U.S. Patent Application Publication No. and 2007/0275362, the disclosures of which are incorporated herein by reference in their entireties), and/or an antioxidant (e.g., probucol; vitamins A, C, and E, coenzyme Q-10, glutathione, L cysteine, N-acetylcysteine, or antioxidant derivative, analogs or salts of the foregoing). In certain embodiments, therapeutic compositions comprising the amnion derived adherent cells further comprise one or more additional cell types, e.g., adult cells (for example, fibroblasts or endodermal cells), or stem or progenitor cells. Such therapeutic agents and/or one or more additional cells, can be administered to an individual in need thereof individually or in combinations or two or more such compounds or agents.

In certain embodiments, the individual to be treated is a mammal. In a specific embodiment the individual to be treated is a human. In specific embodiments, the individual is a livestock animal or a domestic animal. In other specific embodiments, the individual to be treated is a horse, sheep, cow or steer, pig, dog or cat.

5.10.2 Stroke and Other Ischemic Disease

In certain embodiments, provided herein is a method of treating an individual having a disruption of blood flow, e.g., in or around the brain, or in the peripheral vasculature, comprising administering to the individual a therapeutically-effective amount of AMDACs. In certain specific embodiments, the ischemia is peripheral arterial disease (PAD), e.g., is critical limb ischemia (CLI). In certain other embodiments, the ischemia is an ischemia of the central nervous system (CNS). In certain other embodiments, the ischemia is peripheral arterial disease, ischemic vascular disease, ischemic heart disease, ischemic brain disease, or ischemic renal disease.

In a specific embodiment, said disruption of flow of blood is a stroke. In a more specific embodiment, said stroke is an ischemic stroke. In another more specific embodiment, said stroke is a hemorrhagic stroke, e.g., an intracranial cerebral hemorrhage or spontaneous subarachnoid hemorrhage. In another specific embodiment, said disruption is a hematoma. In more specific embodiments, the hematoma is a dural hematoma, a subdural hematoma or a subarachnoid hematoma. In another specific embodiment, said hematoma is caused by external force on the skull, e.g., a head injury. In another specific embodiment, said disruption is a Transient Ischemic Attack (TIA), e.g., recurrent TIA. In another specific embodiment, said disruption is a vasospasm, e.g., a vasospasm following a hemorrhagic stroke.

In another specific embodiment of the method, said therapeutically effective amount is a number of AMDACs that results in elimination of, a detectable improvement in, lessening of the severity of, or slowing of the progression of one or more symptoms of, or neurological deficits attributable to, a disruption of the flow of blood in or around the brain or CNS exhibited by said individual, e.g., anoxic injury or hypoxic injury. In another specific embodiment, said therapeutically effective amount of isolated AMDACs is administered to said individual prophylactically, e.g., to reduce or eliminate neurological damage caused by a second or subsequent disruption of flow of blood in or around the brain or CNS following said disruption of flow of blood.

In another specific embodiment, said symptom of disruption of blood flow in or around the brain, e.g., stroke, anoxic injury or hypoxic injury, is one or more of hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting.

In another specific embodiment, the methods of treatment described above comprise administering a second therapeutic agent to said individual. In a more specific embodiment, said second therapeutic agent is a neuroprotective agent. In a more specific embodiment, said second therapeutic agent is NXY-059 (a disulfonyl derivative of phenylbutylnitrone: disodium 4-((tert-butylimino)-methyl)benzene-1,3-disulfonate N-oxide, or disodium 4-((oxido-tert-butyl-azaniumylidene)methyl)benzene-1,3-disulfonate; also known as disufenton). In another more specific embodiment, the second therapeutic agent is a thrombolytic agent. In a more specific embodiment, said thrombolytic agent is tissue plasminogen activator (tPA). In embodiments in which the disruption of flow of blood in or around the brain is a hemorrhage, the second therapeutic agent can be an antihypertensive drug, e.g., a beta blocker or diuretic drug, a combination of a diuretic drug and a potassium-sparing diuretic drug, a combination of a beta blocker and a diuretic drug, a combination of an angiotensin-converting enzyme (ACE) inhibitor and a diuretic, an angiotensin-II antagonist and a diuretic drug, and/or a calcium channel blocker and an ACE inhibitor. In another more specific embodiment, the second therapeutic agent is a calcium channel blocker, glutamate antagonist, gamma aminobutyric acid (GABA) agonist, an antioxidant or free radical scavenger.

In another specific embodiment of the method of treatment, said isolated AMDACs are administered to said individual within 21-30, e.g., 21 days of development of one or more symptoms of a disruption of the flow of blood in or around the brain of said individual, e.g., within 21-30, e.g., 21 days of development of symptoms of stroke, anoxic injury or hypoxic injury. In another specific embodiment of the method of treatment, said isolated AMDACs are administered to said individual within 14 days of development of one or more symptoms of a disruption of the flow of blood in or around the brain of said individual. In another specific embodiment of the method of treatment, said isolated AMDACs are administered to said individual within 7 days of development of one or more symptoms of a disruption of the flow of blood in or around the brain of said individual. In another specific embodiment of the method of treatment, said isolated AMDACs are administered to said individual within 48 hours of development of one or more symptoms of a disruption of the flow of blood in or around the brain of said individual. In another specific embodiment, said isolated AMDACs are administered to said individual within 24 hours of development of one or more symptoms of a disruption of the flow of blood in or around the brain of said individual. In another specific embodiment, said isolated AMDACs are administered to said individual within 12 hours of development of one or more symptoms of a disruption of the flow of blood in or around the brain of said individual. In another specific embodiment, said isolated AMDACs are administered to said individual within 3 hours of development of one or more symptoms of a disruption of the flow of blood in or around the brain of said individual.

In a specific embodiment, said disruption of flow of blood is critical limb ischemia. In another more specific embodiment, said CLI is a severe blockage in the arteries of the lower extremities, which markedly reduces blood-flow. In another more specific embodiment said CLI is characterized by ischemic rest pain, severe pain in the legs and feet while a person is not moving, non-healing sores on the feet or legs, pain or numbness in the feet, shiny, smooth, dry skin of the legs or feet, thickening of the toenails, absent or diminished pulse in the legs or feet, open sores, skin infections or ulcers that will not heal, dry gangrene (dry, black skin) of the legs or feet. In another specific embodiment, CLI can lead to loss of digits and or whole limbs. In another specific embodiment of the method, said therapeutically effective amount is a number of AMDACs that results in elimination of, a detectable improvement in, lessening of the severity of, or slowing of the progression of one or more symptoms of, loss of limb function and or oxygen deprivation (hypoxia/anoxia) attributable to, a disruption of the flow of blood in or around the brain or CNS exhibited by said individual, e.g., anoxic injury or hypoxic injury. In another specific embodiment, said therapeutically effective amount of isolated AMDACs is administered to said individual prophylactically, e.g., to reduce or eliminate tissue damage caused by a second or subsequent disruption of flow of blood in or around the limb following said disruption of flow of blood.

5.10.3 Dosages and Routes of Administration

Administration of AMDACs to an individual in need thereof can be by any medically-acceptable route relevant for the disease or condition to be treated. In another specific embodiment of the methods of treatment described above, said AMDACs are administered by bolus injection. In another specific embodiment, said isolated AMDACs are administered by intravenous infusion. In a specific embodiment, said intravenous infusion is intravenous infusion over about 1 to about 8 hours. In another specific embodiment, said isolated AMDACs are administered intracranially. In another specific embodiment, said isolated AMDACs are administered intramulscularly. In another specific embodiment, said isolated AMDACs are administered intraperitoneally. In another specific embodiment, said isolated AMDACs are administered intra-arterially. In a more specific embodiment, said isolated AMDACs are administered within an area of ischemia. In another more specific embodiment, said isolated AMDACs are administered to an area peripheral to an ischemia. In another specific embodiment of the method of treatment, said isolated AMDACs are administered intramuscularly, intradermally, or subcutaneously.

In another specific embodiment of the methods of treatment described above, said AMDACs are administered once to said individual. In another specific embodiment, said isolated AMDACs are administered to said individual in two or more separate administrations. In another specific embodiment, said administering comprises administering between about $1\times10^4$ and $1\times10^5$ isolated AMDACs, e.g., AMDACs per kilogram of said individual. In another specific embodiment, said administering comprises administering between about $1\times10^5$ and $1\times10^6$ isolated AMDACs per kilogram of said individual. In another specific embodiment, said administering comprises administering between about $1\times10^6$ and $1\times10^7$ isolated AMDACs per kilogram of said individual. In another specific embodiment, said administering comprises administering between about $1\times10^7$ and $1\times10^8$ isolated placental cells per kilogram of said individual. In other specific embodiments, said administering comprises administering between about $1\times10^6$ and about $2\times10^6$ isolated placental cells per kilogram of said individual; between about $2\times10^6$ and about $3\times10^6$ isolated placental cells per kilogram of said individual; between about $3\times10^6$ and about $4\times10^6$ isolated placental cells per kilogram of said individual; between about $4\times10^6$ and about $5\times10^6$ isolated placental cells per kilogram of said individual; between about $5\times10^6$ and about $6\times10^6$ isolated placental cells per kilogram of said individual; between about $6\times10^6$ and about $7\times10^6$ isolated placental cells per kilogram of said individual; between about $7\times10^6$ and about $8\times10^6$ isolated placental cells per kilogram of said individual; between about $8\times10^6$ and about $9\times10^6$ isolated placental cells per kilogram of said individual; or between about $9\times10^6$ and about $1\times10^7$ isolated placental cells per kilogram of said individual. In another specific embodiment, said administering comprises administering between about $1\times10^7$ and about $2\times10^7$ isolated placental cells per kilogram of said individual to said individual. In another specific embodiment, said administering comprises administering between about $1.3\times10^7$ and about $1.5\times10^7$ isolated placental cells per kilogram of said individual to said individual. In another specific embodiment, said administering comprises administering up to about $3\times10^7$ isolated placental cells per kilogram of said individual to said individual. In a specific embodiment, said administering comprises administering between about $5\times10^6$ and about $2\times10^7$ isolated placental cells to said individual. In another specific embodiment, said administering comprises administering about $150\times10^6$ isolated placental cells in about 20 milliliters of solution to said individual.

In a specific embodiment, said administering comprises administering between about $5\times10^6$ and about $2\times10^7$ isolated placental cells to said individual, wherein said cells are contained in a solution comprising 10% dextran, e.g., dextran-40, 5% human serum albumin, and optionally an immunosuppressant. In another specific embodiment, said administering comprises administering between about $5\times10^7$ and $3\times10^9$ isolated placental cells intravenously. In more specific embodiments, said administering comprises administering about $9\times10^8$ isolated placental cells or about $1.8\times10^9$ isolated placental cells intravenously. In another specific embodiment, said administering comprises administering between about $5\times10^7$ and $1\times10^8$ isolated placental cells intracranially. In a more specific embodiment, said administering comprises administering about $9\times10^7$ isolated placental cells intracranially.

5.11 Differentiation of Amnion Derived Adherent Cells

The amnion derived adherent cells provided herein can be differentiated. In one embodiment, the cell has been differentiated sufficiently for said cell to exhibit at least one characteristic of an endothelial cell, a myogenic cell, or a pericytic cell, e.g., by contacting the cell with vascular endothelial growth factor (VEGF), or as described in Sections 5.11.2, 6.3.3, or 6.3.4, below. In more specific embodiments, said characteristic of an endothelial cell, myogenic cell or pericytic cell is expression of one or more of CD9, CD31, CD54, CD102, NG2 (neural/glial antigen 2) or alpha smooth muscle actin, which is increased compared to an amniotic cell that is OCT-4$^-$, VEGFR2/KDR$^+$, CD9$^+$, CD54$^+$, CD105$^+$, CD200, and VE-cadherin$^-$. In other more specific embodiments, said characteristic of an endothelial cell, myogenic cell or pericytic cell is expression of one or more of CD9, CD31, CD54, CD102, NG2 (neural/glial antigen 2) or alpha smooth muscle actin, which is increased compared to an amniotic cell that is OCT-4$^-$, VEGFR2/KDR, and VEGFR1/Flt-1.

5.11.1 Induction of Angioenesis

Angiogenesis from the amnion derived adherent cells provided herein can be accomplished as follows. The amnion derived adherent cells, are cultured, e.g., in an endothelial cell medium, e.g., EGM®-2 (Lonza) or a medium comprising 60% DMEM-LG (Gibco), 40% MCDB-201 (Sigma); 2% fetal calf serum (Hyclone Labs.); 1× insulin-transferrin-selenium (ITS); 1× linoleic acid-bovine serum albumin (LA-BSA); $5\times10^{-9}$ M dexamethasone (Sigma); $10^{-4}$ M ascorbic acid 2-phosphate (Sigma); epidermal growth factor 10 ng/mL (R&D Systems); and platelet-derived growth factor (PDGF-BB) 10 ng/mL (R&D Systems), to passage 3. The cells are then plated onto MATRIGEL™ or a substrate comprising collagen-1, e.g., in 96-well plates at a density of, e.g., about $1.5\times10^4$ cells per well in the same medium or DMEM with FBS (0-5% v/v) comprising vascular endothelial growth factor (VEGF) at, e.g., about 10 to 50 ng per milliliter. Medium can be changed about twice a week. Angiogenesis is evidenced by visual inspection of the cells for sprouting of vessel-like structures and tube formation, visible under a microscope at a magnification of, e.g., 50× to 100×.

5.11.2 Induction of Differentiation into Cardiac Cells

Myogenic (cardiogenic) differentiation of the amnion derived adherent cells provided herein can be accomplished, for example, by placing the cells in cell culture conditions that induce differentiation into cardiomyocytes. A preferred cardiomyocytic medium comprises DMEM/20% CBS supplemented with retinoic acid, 1 µM; basic fibroblast growth factor, 10 ng/mL; and transforming growth factor beta-1, 2 ng/mL; and epidermal growth factor, 100 ng/mL. KnockOut Serum Replacement (Invitrogen, Carlsbad, Calif.) may be used in lieu of CBS. Alternatively, the amnion derived adherent cells are cultured in DMEM/20% CBS supplemented with 1 to 100, e.g., 50 ng/mL Cardiotropin-1 for 24 hours. In another embodiment, amnion derived adherent cells can be cultured 10-14 days in protein-free medium for 5-7 days, then stimulated with human myocardium extract, e.g., produced by homogenizing human myocardium in 1% HEPES buffer supplemented with 1% cord blood serum.

Differentiation can be confirmed by demonstration of cardiac actin gene expression, e.g., by RT/PCR, or by visible beating of the cell. An adherent cell is considered to have differentiated into a cardiac cell when the cell displays one or more of these characteristics.

6. EXAMPLES

6.1 Example 1

Isolation and Expansion of Adherent Cells from Amniotic Membrane

This Example demonstrates the isolation and expansion of amnion derived adherent cells.

6.1.1 Isolation

Amnion derived adherent cells were isolated from amniotic membrane as follows. Amnion/chorion were cut from the placenta, and amnion was manually separated from the chorion. The amnion was rinsed with sterile PBS to remove residual blood, blood clots and other material. Sterile gauze was used to remove additional blood, blood clots or other material that was not removed by rinsing, and the amnion was rinsed again with PBS. Excess PBS was removed from the membrane, and the amnion was cut with a scalpel into 2" by 2" segments. For epithelial cell release, a processing vessel was set up by connecting a sterile jacketed glass processing vessel to a circulating 37° C. water bath using tubing and connectors, and set on a stir plate. Trypsin (0.25%, 300 mL) was warmed to 37° C. in the processing vessel; the amnion segments were added, and the amnion/trypsin suspension was agitated, e.g., at 100 RPM-150 RPM at 37° C. for 15 minutes. A sterile screening system was assembled by placing a sterile receptacle on a sterile field next to the processing vessel and inserting a sterile 75 µm to 125 µm screen into the receptacle (Millipore, Billerica, Mass.). After agitating the amnion segments for 15 minutes, the contents of the processing vessel were transferred to the screen, and the amnion segments were transferred, e.g., using sterile tweezers back into the processing vessel; the trypsin solution containing the epithelial cells was discarded. The amnion segments were agitated again with 300 mL trypsin solution (0.25%) as described above. The screen was rinsed with approximately 100-150 mL of PBS, and the PBS solution was discarded. After agitating the amnion segments for 15 minutes, the contents of the processing vessel were transferred to the screen. The amnion segments were then transferred back into the processing vessel; the trypsin solution containing the epithelial cells was discarded. The amnion segments were agitated again with 300 mL trypsin solution (0.25%) as described above. The screen was rinsed with approximately 100-150 mL of PBS, and the PBS solution was discarded. After agitating the amnion segments for 15 minutes, the contents of the processing vessel were transferred to the screen. The amnion segments were then transferred back into the processing vessel, and the trypsin solution containing the epithelial cells was discarded. The amnion segments were agitated in PBS/5% FBS (1:1 ratio of amnion to PBS/5% FBS solution by volume) at 37° C. for approximately 2-5 minutes to neutralize the trypsin. A fresh sterile screen system was assembled. After neutralizing the trypsin, the contents of the processing vessel were transferred to the new screen, and the amnion segments were transferred back into the processing vessel. Room temperature, sterile PBS (400 mL) was added to the processing vessel, and the contents of the processing vessel were agitated for approximately 2-5 minutes. The screen was rinsed with approximately 100-150 mL of PBS. After agitation, the contents of the processing vessel were transferred to the screen; the processing flask was rinsed with PBS, and the PBS solution was discarded. The processing vessel was then filled with 300 mL of pre-warmed DMEM, and the amnion segments were transferred into the DMEM solution.

For release of the amnion derived adherent cells, the treated amniotic membrane was further treated with collagenase as follows. A sterile collagenase stock solution (500 U/mL) was prepared by dissolving the appropriate amount of collagenase powder (varied with the activity of the collagenase lot received from the supplier) in DMEM. The solution was filtered through a 0.22 µm filter and dispensed into individual sterile containers. $CaCl_2$ solution (0.5 mL, 600 mM) was added to each 100 mL dose, and the doses were frozen. Collagenase (100 mL) was added to the amnion segments in the processing vessel, and the processing vessel was agitated for 30-50 minutes, or until amnion digestion was complete by visual inspection. After amnion digestion was complete, 100 mL of pre-warmed sterile PBS/5% FBS was added to the processing vessel, and the processing vessel was agitated for an additional 2-3 minutes. Following agitation, the contents of the flask were transferred to a sterile 60 µm screen, and the liquid was collected by vacuum filtration. The processing vessel was rinsed with 400 mL of PBS, and the PBS solution was sterile-filtered. The filtered cell suspension was then centrifuged at 300×g for 15 minutes at 20° C., and the cell pellets were resuspended in pre-warmed PBS/2% FBS (approximately 10 mL total).

6.1.2 Establishment

Freshly isolated angiogenic amniotic cells were added to growth medium containing 60% DMEM-LG (Gibco); 40% MCBD-201 (Sigma); 2% FBS (Hyclone Labs), 1× insulin-transferrin-selenium (ITS); 10 ng/mL linoleic acid-bovine serum albumin (LA-BSA); 1 n-dexamethasone (Sigma); 100 µM ascorbic acid 2-phosphate (Sigma); 10 ng/mL epidermal growth factor (R & D Systems); and 10 ng/mL platelet-derived growth factor (PDGF-BB) (R & D Systems) and were plated in a T-Flask at a seeding density of 10,000 cells per $cm^2$. The culture device(s) were then incubated at 37° C., 5% $CO_2$ with >90% humidity. Cellular attachment, growth, and morphology were monitored daily. Non-adherent cells and debris were removed by medium exchange. Medium exchange was performed twice per week. Adherent cells with typical fibroblastoid/spindle shape morphology appeared at several days after initial plating. When confluency reached 40%-70% (at 4-11 days after initial plating), the cells were harvested by trypsinization (0.25% trypsin—EDTA) for 5 minutes at room temperature (37° C.). After neutralization with PBS-5% FBS, the cells were centrifuged at 200-400 g for 5-15 minutes at room temperature, and then were resuspended in growth medium. At this point, an AMDAC line was considered to be successfully established at the initial passage. Initial passage amnion derived adherent cells were, in some cases, cryopreserved or expanded.

6.1.3 Culture Procedure

Amnion derived adherent cells were cultured in the growth medium described above and seeded at a density of 2000-4000 per $cm^2$ in an appropriate tissue culture-treated culture device(s). The culture device(s) were then incubated at 37° C., 5% $CO_2$ with >90% humidity. During culture, AMDACs would adhere and proliferate. Cellular growth, morphology, and confluency were monitored daily. Medium exchange was performed twice a week to replenish fresh nutrients if the culture extended to 5 days or more. When confluency reached 40%-70% (at 3-7 days after seeding), the cells were harvested by trypsinization (0.05%-0.25% trypsin—EDTA) for 5 minutes at room temperature (37° C.). After neutralization with PBS-5% FBS, the cells were centrifuged at 200-400 g for 5-15 minutes at room temperature, then were resuspended in growth medium.

AMDACs isolated and cultured in this manner typically produced 33530+/−15090 colony-forming units (fibroblast) (CFU-F) out of 1×10⁶ cells plated.

6.2 Example 2

Phenotypic Characterization of Amnion Derived Adherent Cells 6.2.1 Gene and Protein Expression Profiles This Example describes phenotypic characterization of amnion derived adherent cells, including characteristic cell surface marker, mRNA, and proteomic expression.

Sample Preparation:

Amnion derived adherent cells were obtained as described in Example 1. The cells at passage 6 were grown to approximately 70% confluence in growth medium as described in Example 1, above, trypsinized, and washed in PBS. NTERA-2 cells (American Type Culture Collection, ATCC Number CRL-1973) were grown in DMEM containing 4.5 g/L glucose, 2 mM glutamine and 10% FBS. Nucleated cell counts were performed to obtain a minimum of 2×10⁶ to 1×10⁷ cells. The cells were then lysed using a Qiagen RNeasy kit (Qiagen, Valencia, Calif.), utilizing a QIAshredder, to obtain the lysates. The RNA isolation was then performed using a Qiagen RNeasy kit. RNA quantity and quality were determined using a Nanodrop ND 1000 spectrophotometer, 25 ng/μL of RNA/reaction. The cDNA reactions were prepared using an Applied Biosystems (Foster City, Calif.) High Capacity cDNA Archive Kit. Real time PCR reactions were performed using TAQMAN® universal PCR master mixes from Applied Biosystems. Reactions were run in standard mode on an Applied Biosystems 7300 Real time PCR system for 40 cycles.

Sample Analysis and Results:

Using the real time PCR methodology and specific TAQMAN® gene expression probes and/or the TAQMAN® human angiogenesis array (Applied Biosystems), cells were characterized for expression of stem cell-related, angiogenic and cardiomyogenic markers. Results were expressed either as the relative expression of a gene of interest in comparison to the pertinent cell controls, or the relative expression (delta Ct) of the gene of interest in comparison to a ubiquitously expressed housekeeping gene (for example, GAPDH, 18S, or GUSB).

Figure 1:
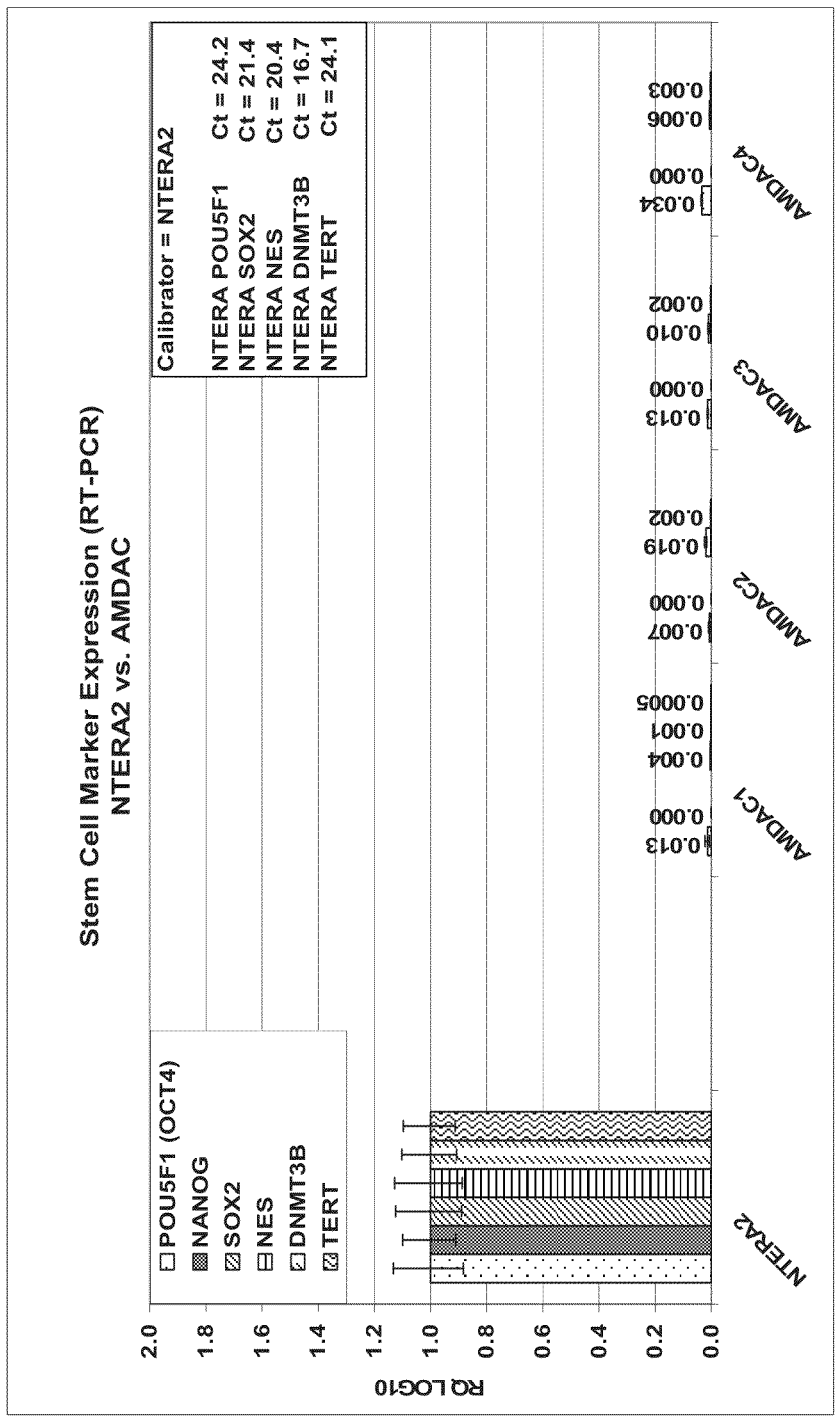
FIG. 1 shows expression of stem cell-related genes by amnion derived adherent cells and NTERA-2 cells.
Figure 3A:
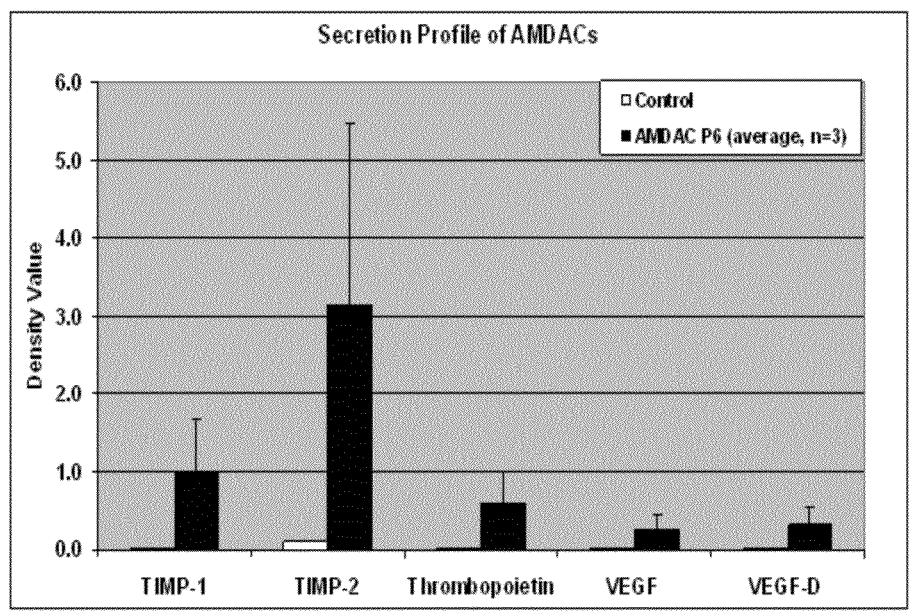
Figure 3B:
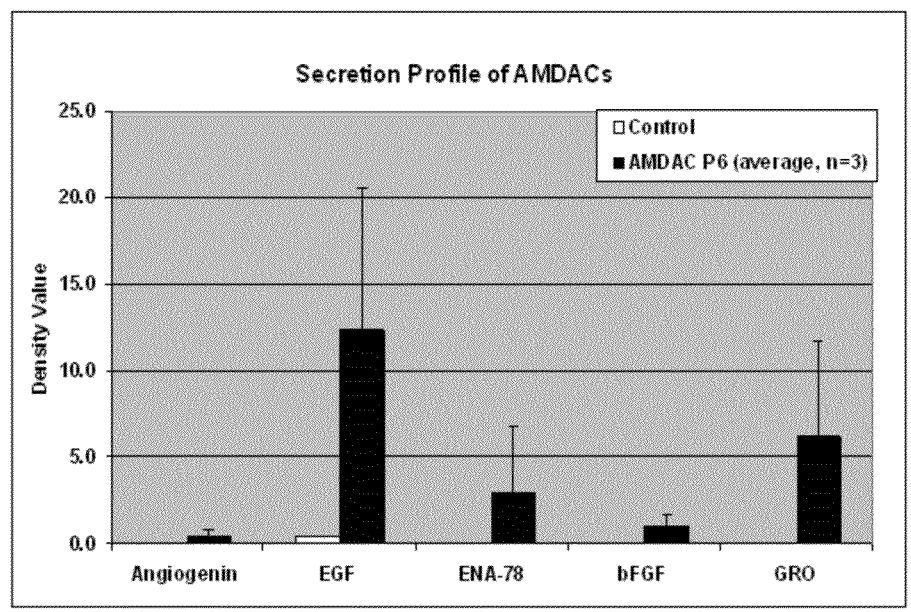
Figure 3C:
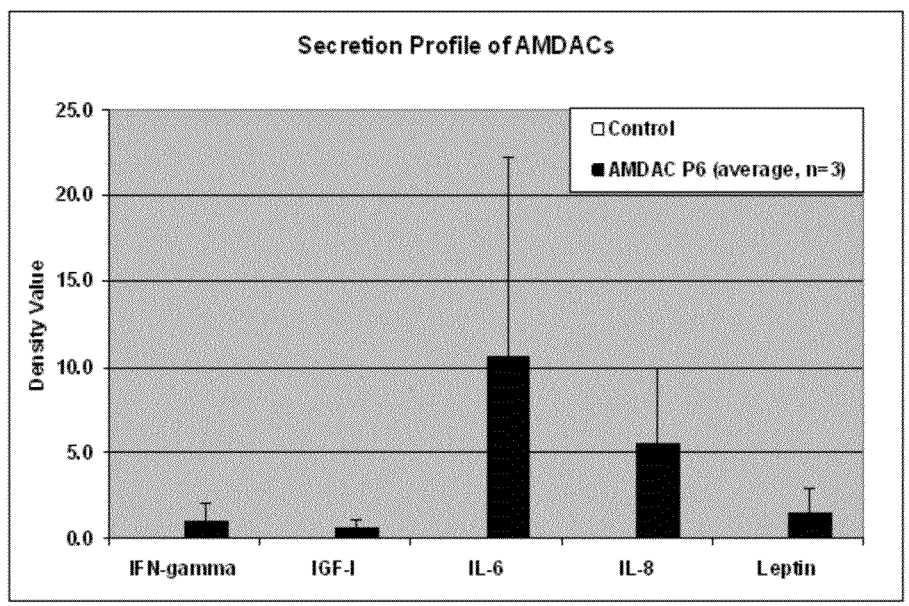
Figure 3D:
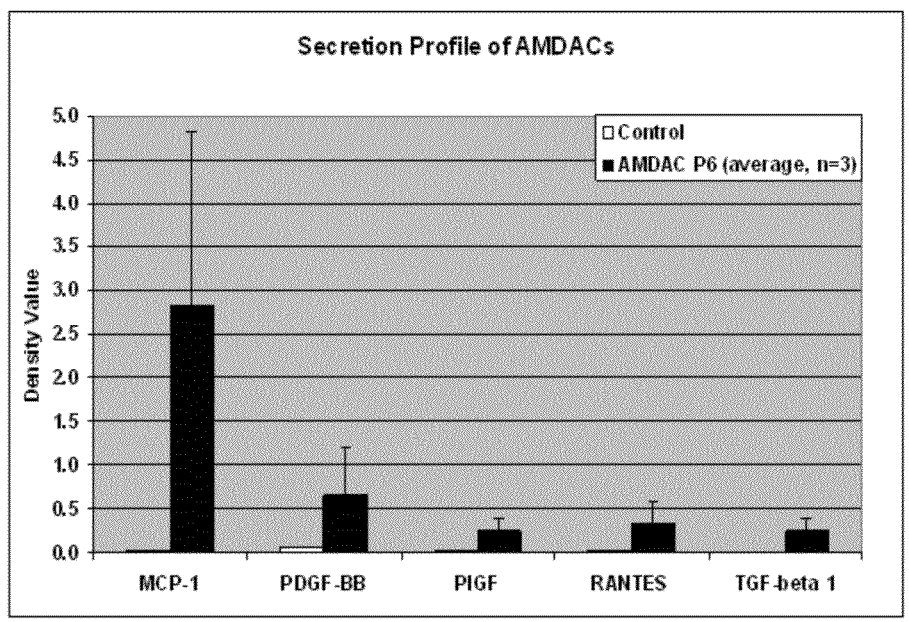

Amnion derived adherent cells expressed various, stem-cell related, angiogenic and cardiomyogenic genes and displayed a relative absence of OCT-4 expression in comparison to NTERA-2 cells. Table 1 summarizes the expression of selected angiogenic, cardiomyogenic, and stem cell genes, and FIG. 1 demonstrates the lack of expression in AMDACs of the stem cell-related genes POU5F1 (OCT-4), NANOG, SOX2, NES, DNMT3B, and TERT.

TABLE 1

Gene expression profile of amnion derived adherent cells as determined by RT-PCR.

| AMDAC Marker | Positive | Negative | mRNA |
|---|---|---|---|
| ACTA2 | X | | X |
| ACTC1 | X | | X |
| ADAMTS1 | X | | X |
| AMOT | X | | X |
| ANG | X | | X |
| ANGPT1 | X | | X |
| ANGPT2 | X | | X |
| ANGPT4 | | X | X |
| ANGPTL1 | X | | X |
| ANGPTL2 | X | | X |
| ANGPTL3 | | X | X |
| ANGPTL4 | X | | X |
| BAI1 | X | | X |
| BGLAP | | X | X |
| c-myc | X | | X |
| CD31 | | X | X |
| CD34 | | X | X |
| CD44 | X | | X |
| CD140a | X | | X |
| CD140b | X | | X |
| CD200 | X | | X |
| CD202b | X | | X |
| CD304 | X | | X |
| CD309 (VEGFR2/KDR) | X | | X |
| CDH5 | | X | X |
| CEACAM1 | X | | X |
| CHGA | X | | X |
| COL15A1 | X | | X |
| COL18A1 | X | | X |
| COL4A1 | X | | X |
| COL4A2 | X | | X |
| COL4A3 | X | | X |
| Connexin-43 | X | | X |
| CSF3 | X | | X |
| CTGF | X | | X |
| CXCL10 | | X | X |
| CXCL12 | X | | X |
| CXCL2 | X | | X |
| DLX5 | | X | X |
| DNMT3B | X | | X |
| ECGF1 | X | | X |
| EDG1 | X | | X |
| EDIL3 | X | | X |
| ENPP2 | X | | X |
| EPHB2 | X | | X |
| F2 | X | | X |
| FBLN5 | X | | X |
| FGA | | X | X |
| FGF1 | X | | X |
| FGF2 | X | | X |
| FGF4 | | X | X |
| FIGF | X | | X |
| FLT3 | | X | X |
| FLT4 | X | | X |
| FN1 | X | | X |
| FOXC2 | X | | X |
| Follistatin | X | | X |
| Galectin-1 | X | | X |
| GRN | X | | X |
| HEY1 | X | | X |
| HGF | X | | X |
| HLA-G | | X | X |
| HSPG2 | X | | X |
| IFNB1 | X | | X |
| IFNG | | X | X |
| IL-8 | X | | X |
| IL-12A | X | | X |
| ITGA4 | X | | X |
| ITGAV | X | | X |
| ITGB3 | X | | X |
| KLF-4 | X | | X |
| LECT1 | | X | X |
| LEP | | X | X |
| MDK | X | | X |

TABLE 1-continued

Gene expression profile of amnion derived adherent cells as determined by RT-PCR.

| AMDAC Marker | Positive | Negative | mRNA |
|---|---|---|---|
| MMP-13 |  | X | X |
| MMP-2 | X |  | X |
| MYOZ2 | X |  | X |
| NANOG |  | X | X |
| NESTIN |  | X | X |
| NRP2 | X |  | X |
| PDGFB | X |  | X |
| PF4 | X |  | X |
| PGK1 | X |  | X |
| PLG |  | X | X |
| POU5F1 (OCT-4) |  | X | X |
| PRL |  | X | X |
| PROK1 |  | X | X |
| PROX1 | X |  | X |
| PTN | X |  | X |
| SEMA3F | X |  | X |
| SERPINB5 | X |  | X |
| SERPINC1 | X |  | X |
| SERPINF1 | X |  | X |
| SOX2 |  | X | X |
| TERT |  | X | X |
| TGFA | X |  | X |
| TGFB1 | X |  | X |
| THBS1 | X |  | X |
| THBS2 | X |  | X |
| TIE1 | X |  | X |
| TIMP2 | X |  | X |
| TIMP3 | X |  | X |
| TNF | X |  | X |
| TNFSF15 | X |  | X |
| TNMD |  | X | X |
| TNNC1 | X |  | X |
| TNNT2 | X |  | X |
| VASH1 | X |  | X |
| VEGF | X |  | X |
| VEGFB | X |  | X |
| VEGFC | X |  | X |
| VEGFR1/FLT-1 | X |  | X |
| XLKD1 |  | X | X |

Column "mRNA" indicates that the presence or absence of mRNA for particular markers were determined in each instance.

In a separate experiment, AMDACs were additionally found to express genes for Aryl hydrocarbon receptor nuclear translocator 2 (ARNT2), nerve growth factor (NGF), brain-derived neurotrophic factor (BDNF), glial-derived neurotrophic factor (GDNF), neurotrophin 3 (NT-3), NT-5, hypoxia-Inducible Factor 1α (HIF1A), hypoxia-inducible protein 2 (HIG2), heme oxygenase (decycling) 1 (HMOX1), Extracellular superoxide dismutase [Cu—Zn](SOD3), catalase (CAT), transforming growth factor β1 (TGFB1), transforming growth factor β1 receptor (TGFB1R), and hepatoycte growth factor receptor (HGFR/c-met).

6.2.2 Flow Cytometry for Evaluation of Angiogenic Potency of Amnion Derived Adherent Cells Flow cytometry was used as a method to quantify phenotypic markers of amnion derived adherent cells to define the identity of the cells. Cell samples were obtained from frozen stocks. Prior to thaw and during reagent preparation, cell vials were maintained on dry ice. Subsequently, samples were thawed rapidly using a 37° C. water bath. Pre-freeze cell counts were used for calculations for initial post-thaw cell number-dependent dilutions. Briefly, cryovials were thawed in a 37° C. water bath for approximately 30 seconds with gentle agitation. Immediately following thawing, approximately 100-200 μL of cold (2 to 8° C.) thawing solution (PBS with 2.5% albumin and 5% Gentran 40) was added to the cryovial and mixed. After gentle mixing, the total volume in the cryovials was transferred into a 15 mL conical tube containing an equal volume of cold (2 to 8° C.) thawing solution. The cells were centrifuged in a conical tube at 400 g for 5 minutes at room temperature before removing the supernatant. The residual volume was measured with a pipette (estimation); the residual volume and cell pellet were resuspended at room temperature in 1% FBS in PBS to achieve a cell concentration of $250 \times 10^3$ cells/100 μL buffer. For example, $1 \times 10^6$ cells would be resuspended in 400 μL 1% FBS. The cell suspension was placed into pre-labeled 5 mL FACS tubes (Becton Dickinson (BD), Franklin Lakes, N.J.). For each primary antibody isotype, 100 μL of cell suspension was aliquoted into one isotype control tube. Prior to phenotype analysis, the concentrations of all antibodies were optimized to achieve good signal to noise ratios and adequate detection of CD antigens across a potential four-log dynamic range. The volume of each isotype and sample antibody that was used to stain each sample was determined. To standardize the amount of antibody (in μg) in the isotype and sample tubes, the concentration of each antibody was calculated as (1/actual antibody concentration (μg/μL))×(desired final quantity of antibody in μg for $2.5 \times 10^5$ cells)=#μL of antibody added. A master mix of antibodies for both the isotype and the sample was made with the appropriate amount of antibody added to each tube. The cells were stained for 15-20 minutes at room temperature in the dark. After staining, unbound antibody in each sample was removed by centrifugation (400 g×5 minutes) followed by washing using 2 mL 1% FBS PBS (room temperature) before resuspension in 150 μL of room temperature 1% FBS PBS. The samples were then analyzed on Becton Dickinson FACSCalibur, FACSCantoI or BD FACSCantoII flow cytometers prepared for use per manufacturer's instructions. Multi-parametric flow cytometry data sets (side scatter (SSC), forward scatter (FSC) and integrated fluorescence profiles (FL)) were acquired without setting on-the-fly instrument compensation parameters. Compensation parameters were determined after acquisition using the FACSDiva software according to the manufacturer's instructions. These instrument settings were applied to each sample. Fluorophore conjugates used in these studies were Allophycocyanin (APC), AlexaFluor 647 (AF647), Fluorescein isothiocyanate (FITC), Phycoerythrin (PE) and Peridinin chlorophyll protein (PerCP), all from BD Biosciences. Table 2 summarizes the expression of selected cell-surface markers, including angiogenic markers.

TABLE 2

Cell surface marker expression in amnion derived adherent cells as determined by flow cytometry.

| AMDAC Marker | Positive | Negative | Immuno-localization Flow Cytometry |
|---|---|---|---|
| CD6 |  | X | X |
| CD9 | X |  | X |
| CD10 | X |  | X |
| CD31 |  | X | X |
| CD34 |  | X | X |
| CD44 | X |  | X |
| CD45 |  | X | X |
| CD49b | X |  | X |
| CD49c | X |  | X |
| CD49d | X |  | X |
| CD54 | X |  | X |
| CD68 | X |  | X |
| CD90 | X |  | X |
| CD98 | X |  | X |

TABLE 2-continued

Cell surface marker expression in amnion derived adherent cells as determined by flow cytometry.

| AMDAC Marker | Positive | Negative | Immunolocalization Flow Cytometry |
|---|---|---|---|
| CD105 | X | | X |
| CD117 | | X | X |
| CD133 | | X | X |
| CD143 | | X | X |
| CD144 (VE-cadherin) | | X | X |
| CD146 | | X | X |
| CD166 | X | | X |
| CD184 | | X | X |
| CD200 | X | | X |
| CD202b | X | | X |
| CD271 | | X | X |
| CD304 | X | | X |
| CD309 (VEGFR2/KDR) | X | | X |
| CD318 | X | | X |
| CD349 | X | | X |
| CytoK | X | | X |
| HLA-ABC+ B2 Micro+ | X | | X |
| Invariant Chain+ HLA-DR-DP-DQ+ | | X | X |
| PDL-1 | X | | X |
| VEGFR1/FLT-1 | X | | X |
| | | | X |

Column "Immunolocalization Flow Cytometry" indicates that the presence or absence of particular markers were determined by immunolocalization, specifically flow cytometry.

In another experiment, AMDAC cells were labeled with anti-human CD49f (Clone GoH3, phycoerythrin-conjugated; BD Pharmingen Part No. 555736), and analyzed by flow cytometry. Approximately 96% of the AMDACs labeled with anti-CD49f (that is, were CD49f).

In other experiments, AMDACs were additionally found by immunolocalization to express CD49a, CD106, CD119, CD130, c-met (hepatocyte growth factor receptor; HGFR), CXC chemokine receptor 1 (CXCR1), PDGFRA, and PDG-FRB by immunolocalization. AMDACs were also found, by immunolocalization, to lack expression of CD49e, CD62E, fibroblast growth factor receptor 3 (FGFR3), tumor necrosis factor receptor superfamily member 12A (TNFRSF12A), insulin-like growth factor 1 receptor (IGF-1R), CXCR2, CXCR3, CXCR4, CXCR6, chemokine receptor 1 (CCR1), CCR2, CCR3, CCR4, CCR5, CCR6, CCR7, CCR8, CCR9, epidermal growth factor receptor (EGF-R), insulin receptor (CD220), interleukin receptor 4 (IL4-R; CD124), IL6-R (CD126), TNF-R1a and 1b (CD120a, b), and erbB2/Her2.

6.2.3 Immunohistochemistry (IHC)/Immunofluorochemistry (IFC) for Evaluation of Angiogenic Potency of Amnion Derived Adherent Cells Amnion derived adherent cells from passage 6 were grown to approximately 70% confluence on 4-well chamber slides and fixed with a 4% formalin solution for 30 minutes each. After fixation, the slides were rinsed with PBS two times for 5 minutes. The slides were then incubated with 10% normal serum from the same host as the secondary antibody, 2× casein, and 0.3% Triton X100 in PBS, for 20 minutes at room temperature in a humid chamber. Excess serum was blotted off and the slides were incubated with primary antibody (goat polyclonal IgG (Santa Cruz; Santa Cruz, Calif.) in a humidified chamber. Time and temperature for incubations were determined by selecting the optimal conditions for the antibody being used. In general, incubation times were 1 to 2 hours at 37° C. or overnight at 4° C. The slides were then rinsed with PBS three times for 5 minutes each and incubated for 20-30 minutes at room temperature in a humid chamber with fluorescent-conjugated anti-immunoglobulin secondary antibody directed against the host of the primary antibody (rabbit anti-goat antibody (Santa Cruz)). Thereafter, the slides were rinsed with PBS three times for 5 minutes each, mounted with a coverslip utilizing DAPI VECTASHIELD® (Vector Labs) mounting solution to counterstain nuclei. Cell staining was visualized utilizing a Nikon fluorescence microscope. All pictures were taken at equal exposure time normalized against the background of the corresponding isotype (goat IgG (Santa Cruz)). Table 3 summarizes the results for the expression of angiogenic proteins by amnion derived adherent cells.

TABLE 3

Angiogenic markers present or absent on amnion derived adherent cells.

| AMDAC Marker | Positive | Negative | Immunolocalization Immunofluorescence Immunohistochemistry |
|---|---|---|---|
| CD31 | | X | X |
| CD34 | | X | X |
| (VEGFR2/KDR) | X | | X |
| Connexin-43 | X | | X |
| Galectin-1 | X | | X |
| TEM-7 | X | | X |

Amnion derived adherent cells expressed the angiogenic marker tumor endothelial marker 7 (TEM-7), one of the proteins shown in Table 3. See FIG. 2.

6.2.4 Membrane Proteomics for Evaluation of Angiogenic Potency of Amnion Derived Adherent Cells Membrane Protein Purification:

Cells at passage 6 were grown to approximately 70% confluence in growth medium, trypsinized, and washed in PBS. The cells were then incubated for 15 minutes with a solution containing protease inhibitor cocktail (P8340, Sigma Aldrich, St. Louis, Mo.) prior to cell lysis. The cells were then lysed by the addition of a 10 mM HCl solution (thus avoiding the use of detergents) and centrifuged for 10 minutes at 400 g to pellet and remove the nuclei. The post-nuclear supernatant was transferred to an ultracentrifugation tube and centrifuged using a WX80 ultracentrifuge with a T-1270 rotor (Thermo Fisher Scientific, Asheville, N.C.) at 100,000 g for 150 minutes generating a membrane protein pellet.

Generation, Immobilization and Digestion of Proteoliposomes:

The membrane protein pellet was washed several times using Nanoxis buffer (10 mM Tris, 300 mM NaCl, pH 8). The membrane protein pellet was suspended in 1.5 mL of Nanoxis buffer and then tip-sonicated using a VIBRA-CELL™ VC505 ultrasonic processor (Sonics & Materials, Inc., Newtown, Conn.) for 20 minutes on ice. The size of the proteoliposomes was determined by staining with FM 1-43 dye (Invitrogen, Carlsbad, Calif.) and visualization with fluorescence microscopy. The protein concentration of the proteoliposome suspension was determined by a BCA assay (Thermo Scientific). The proteoliposomes were then injected onto an LPI™ Flow Cell (Nanoxis AB, Gothenburg, Sweden) using a standard pipette tip and allowed to immobilize for 1 hour. After immobilization, a series of washing steps were carried out and trypsin at 5 µg/mL (Princeton Separations, Adelphi, N.J.) was injected directly onto the LPI™ Flow Cell. The chip was incubated overnight at 37° C. and the tryptic peptides were eluted from the LPI™ chip and then desalted using a Sep-Pak cartridge (Waters Corporation, Milford, Mass.).

LTQ Linear Ion Trap LC/MS/MS Analysis:

Each tryptic digest sample was separated on a 0.2 mm×150 mm 3 μm 200 Å MAGIC C18 column (Michrom Bioresources, Inc., Auburn, Calif.) that was interfaced directly to an axial desolvation vacuum-assisted nanocapillary electrospray ionization (ADVANCE) source (Michrom Bioresources, Inc.) using a 180 minute gradient (Buffer A: Water, 0.1% Formic Acid; Buffer B: Acetonitrile, 0.1% Formic Acid). The ADVANCE source achieves a sensitivity that is comparable to traditional nanoESI while operating at a considerably higher flow rate of 3 μL/min. Eluted peptides were analyzed on an LTQ linear ion trap mass spectrometer (Thermo Fisher Scientific, San Jose, Calif.) that employed ten data-dependent MS/MS scans following each full scan mass spectrum. Seven analytical replicate datasets were collected for each biological sample.

Bioinformatics:

Seven RAW files corresponding to the 7 analytical replicate datasets that were collected for each cell line were searched as a single search against the IPI Human Database using an implementation of the SEQUEST algorithm on a Sorcerer Solo™ workstation (Sage-N Research, San Jose, Calif.). A peptide mass tolerance of 1.2 amu was specified, oxidation of methionine was specified as a differential modification, and carbamidomethylation was specified as a static modification. Scaffold software implementation of the Trans-Proteomic Pipeline (TPP) was used to sort and parse the membrane proteomic data. Proteins were considered for analysis if they were identified with a peptide probability of 95%, protein probability of 95% and 1 unique peptide. Comparisons between membrane proteomic datasets were made using custom Perl scripts developed in-house.

Results:

As shown in Table 4, amnion derived adherent cells expressed various angiogenic and cardiomyogenic markers.

TABLE 4

Cardiomyogenic or angiogenic markers expressed by amnion derived adherent cells.

| AMDAC Marker | Positive | Negative | Immunolocalization Membrane Proteomics |
|---|---|---|---|
| Activin receptor type IIB | X | | X |
| ADAM 17 | X | | X |
| Alpha-actinin 1 | X | | X |
| Angiotensinogen | X | | X |
| Filamin A | X | | X |
| Macrophage acetylated LDL receptor I and II | X | | X |
| Megalin | X | | X |
| Myosin heavy chain non muscle type A | X | | X |
| Myosin-binding protein C cardiac type | X | | X |
| Wnt-9 | X | | X |

6.2.5 Secretome Profiling for Evaluation of Angioenic Potency of Amnion Derived Adherent Cells Protein Arrays:

Amnion derived adherent cells at passage 6 were plated at equal cell numbers in growth medium and conditioned media were collected after 4 days. Simultaneous qualitative analysis of multiple angiogenic cytokines/growth factors in cell-conditioned media was performed using RayBiotech Angiogenesis Protein Arrays (Norcross, Ga.). In brief, protein arrays were incubated with 2 mL 1× Blocking Buffer (Ray Biotech) at room temperature for 30 minutes (min) to block membranes. Subsequently, the Blocking Buffer was decanted and the membranes were incubated with 1 mL of sample (growth medium conditioned by the respective cells for 4 days) at room temperature for 1 to 2 hours. The samples were then decanted and the membranes were washed 3×5 min with 2 mL of 1× Wash Buffer I (Ray Biotech) at room temperature with shaking. Then, the membranes were washed 2×5 min with 2 mL of 1× Wash Buffer II (Ray Biotech) at room temperature with shaking. Thereafter, 1 mL of diluted biotin-conjugated antibodies (Ray Biotech) was added to each membrane and incubated at room temperature for 1-2 hours and washed with the Wash Buffers as described above. Diluted HRP-conjugated streptavidin (2 mL) was then added to each membrane and the membranes were incubated at room temperature for 2 hours. Finally, the membranes were washed again, incubated with the ECL™ detection kit (Amersham) according to specifications and the results were visualized and analyzed using the Kodak Gel Logic 2200 Imaging System. The secretion of various angiogenic proteins by AMDACs is shown in FIG. 3.

ELISAs:

Quantitative analysis of single angiogenic cytokines/growth factors in cell-conditioned media was performed using commercially available kits from R&D Systems (Minneapolis, Minn.). In brief, ELISA assays were performed according to manufacturer's instructions and the amount of the respective angiogenic growth factors in the conditioned media was normalized to $1\times10^6$ cells. Amnion derived adherent cells (n=6) exhibited approximately 4500 μg VEGF per million cells and approximately 17,200 μg IL-8 per million cells.

TABLE 5

ELISA results for angiogenic markers

| AMDAC Marker | Positive | Negative | Secretome Analysis ELISA, Protein Arrays |
|---|---|---|---|
| ANG | X | | X |
| EGF | X | | X |
| ENA-78 | X | | X |
| FGF2 | X | | X |
| Follistatin | X | | X |
| G-CSF | X | | X |
| GRO | X | | X |
| HGF | X | | X |
| IL-6 | X | | X |
| IL-8 | X | | X |
| Leptin | X | | X |
| MCP-1 | X | | X |
| MCP-3 | X | | X |
| PDGFB | X | | X |
| PLGF | X | | X |
| Rantes | X | | X |
| TGFB1 | X | | X |
| Thrombopoietin | X | | X |
| TIMP1 | X | | X |
| TIMP2 | X | | X |
| uPAR | X | | X |
| VEGF | X | | X |
| VEGFD | X | | X |

In a separate experiment, AMDACs were confirmed to also secrete angiopoietin-1, angiopoietin-2, PECAM-1 (CD31; platelet endothelial cell adhesion molecule), laminin and fibronectin.

6.2.6 AMDAC MicroRNA Expression Confirms Angiogenic Activity

This Example demonstrates that AMDACs express higher levels of certain micro-RNAs (miRNAs), and lower levels of certain other miRNAs, each of which correlated with angiogenic function, than bone marrow-derived mesenchymal stem cells.

It is known that pro-angiogenic miR-296 regulates angiogenic function through regulating levels of growth factor receptors. For example, miR-296 in endothelial cells contributes significantly to angiogenesis by directly targeting the hepatocyte growth factor-regulated tyrosine kinase substrate (HGS) mRNA, leading to decreased levels of HGS and thereby reducing HGS-mediated degradation of the growth factor receptors VEGFR2 and PDGFRb. See Würdinger et al., *Cancer Cell* 14:382-393 (2008). In addition, miR-15b and miR-16 have been shown to control the expression of VEGF, a key pro-angiogenic factor involved in angiogenesis, and that hypoxia-induced reduction of miR-15b and miR-16 contributes to an increase in VEGF, a pro-angiogenic cytokine. See Kuelbacher et al., Trends in Pharmacological Sciences, 29(1):12-15 (2007).

AMDACs were prepared as described in Example 1, above. AMDACs and BM-MSC cells (used as a comparator) were subjected to microRNA (miRNA) preparation using a MIRVANA™ miRNA Isolation Kit (Ambion, Cat#1560). $0.5 \times 10^6$ to $1.5 \times 10^6$ cells were disrupted in a denaturing lysis buffer. Next, samples were subjected to acid-phenol+chloroform extraction to isolate RNA highly enriched for small RNA species. 100% ethanol was added to bring the samples to 25% ethanol. When this lysate/ethanol mixture was passed through a glass fiber filter, large RNAs were immobilized, and small RNA species were collected in the filtrate. The ethanol concentration of the filtrate was then increased to 55%, and the mixture was passed through a second glass fiber filter where the small RNAs became immobilized. This RNA was washed, and eluted in a low ionic strength solution. The concentration and purity of the recovered small RNA was determined by measuring its absorbance at 260 and 280 nm.

AMDACs were found to express the following angiogenic miRNA: miR-17-3p, miR-18a, miR-18b, miR-19b, miR-92, miR-20a, miR-20b, (members of the of the angiogenic miRNA cluster 17-92), miR-296, miR-221, miR-222, miR-15b, miR-16. AMDACs were also found to express higher levels of the following angiogenic miRNA when compared to bone marrow-derived mesenchymal stem cells (BM-MSCs): miR-17-3p, miR-18a, miR-18b, miR-19b, miR-92 (members of the of the angiogenic miRNA cluster 17-92), miR-296. These results correlate well with the observation that AMDACs express high levels of VEGFR2/KDR (see above). Conversely, AMDACs were found to express lower levels of the following angiogenic miRNA when compared to BM-MSCs: miR-20a, miR-20b, (members of the of the angiogenic miRNA cluster 17-92), miR-221, miR-222, miR-15b, miR-16. The reduced expression of miR-15b and miR-16 correlated with the higher levels of expression of VEGF seen in AMDACs.

6.3 Example 3

Functional Characterization of Amnion Derived Adherent Cells

This Example demonstrates different characteristics of AMDACs associated with angiogenesis and differentiation capability.

6.3.1 HUVEC Tube Formation for Evaluation of Angiogenic Potency of Amnion Derived Adherent Cells Human Umbilical Vein Endothelial Cells (HUVEC) were subcultured at passage 3 or less in EGM-2 medium (Cambrex, East Rutherford, N.J.) for 3 days, and harvested at a confluency of approximately 70%-80%. HUVEC were washed once with basal medium/antibiotics (DMEM/F12 (Gibco)) and resuspended in the same medium at the desired concentration. HUVEC were used within 1 hour of preparation. Human placental collagen (HPC) was brought to a concentration of 1.5 mg/mL in 10 mM HCl (pH 2.25), was "neutralized" with buffer to pH 7.2 and kept on ice until used. The HPC was combined with the HUVEC suspension at a final cell concentration of 4000 cells/µl. The resulting HUVEC/HPC suspension was immediately pipetted into 96-well plates at 3 µl per well (plate perimeter must be pre-filled with sterile PBS to avoid evaporation, n=5 per condition). HUVEC drops were incubated at 37° C. and 5% $CO_2$ for 75-90 minutes without medium addition to allow for collagen polymerization. Upon completion of "dry" incubation, each well was gently filled with 200 µl of conditioned AMDAC medium (n=5 cell lines) or control medium (e.g., DMEM/F12 as the negative control, and EGM-2 as the positive control) and incubated at 37° C. and 5% $CO_2$ for 20 hrs. Conditioned medium was prepared by incubating amnion derived adherent cells at passage 6 in growth medium for 4-6 hours; after attachment and spreading, the medium was changed to DMEM/F12 for 24 hours. After incubation, the medium was removed from the wells without disturbing the HUVEC drops and the wells were washed once with PBS. The HUVEC drops were then fixed for 10 seconds and stained for 1 minute using a Diff-Quik cell staining kit and subsequently rinsed 3× times with sterile water. The stained drops were allowed to air dry and images of each well were acquired using the Zeiss SteReo Discovery V8 microscope. The images were then analyzed using the computer software package, "ImageJ" and/or MatLab. Images were converted from color to 8-bit grayscale images and thresholded to convert to a black and white image. The image was then analyzed using the particle analysis features, which provided pixel density data, including count (number of individual particles), total area, average size (of individual particles), and area fraction, which equates to the amount endothelial tube formation in the assay.

The conditioned medium exerted an angiogenic effect on endothelial cells, as demonstrated by the induction of proliferation tube formation (see FIG. 4).

6.3.2 HUVEC Migration Assay

This experiment demonstrated the angiogenic capacity of amnion derived adherent cells. HUVECs were grown to confluence in a fibronectin (FN)-coated 12-well plate and the monolayer was "wounded" with a 1 mL plastic pipette tip to create an acellular line across the well. HUVEC migration was tested by incubating the "wounded" cells with serum-free conditioned medium (EBM2; Cambrex) obtained from 5 amnion derived adherent cell lines after 3 days of growth. EBM2 medium without cells was used as the control. After 15 hours, the cell migration into the acellular area was recorded (n=3) using an inverted microscope. The pictures were then analyzed using the computer software package, "ImageJ" and/or MatLab. Images were converted from color to 8-bit grayscale images and thresholded to convert to a black and white image. The image was then analyzed using the particle analysis features, which provided pixel density data, including count (number of individual particles), total area, average size (of individual particles), and area fraction, which equates to the amount endothelial migration in the assay. The degree of cell migration was scored against the size of the initially recorded wound line and the results were normalized to $1 \times 10^6$ cells.

The trophic factors secreted by amnion derived adherent cells exerted angiogenic effects on endothelial cells, as demonstrated by the induction of cell migration (FIG. 5).

In a separate experiment, HUVECs were grown to subconfluence in a FN-coated 96-well plate, and induction of proliferation was tested by incubating the cells with serum-free conditioned medium from each of 5 amnion derived adherent cell lines (EBM-2 medium, 3 days). EBM-2 medium was used as the negative control, and EGM-2 was used as the positive control. After 48 hours, the cell proliferation was scored by DNA content measurements using a Promega Cell Titer 96® AZ One Solution Cell Proliferation Assay (Promega, Madison, Wis.). Error bars denote standard deviations of analytical replicates (n=3) and the results were normalized to $1 \times 10^6$ cells.

The trophic factors secreted by amnion derived adherent cells resulted in an increase in DNA concentration, which is indicative of HUVEC proliferation. See FIG. 6, where "CM" is conditioned medium.

6.3.3 Acetylated Low Density Lipoprotein (AcLDL) Uptake for Evaluation of Angiogenic Potency of Amnion Derived Adherent Cells Endothelial cells and microglial cells in culture can be identified by their ability to take up fluorescent AcLDL. If the lysine residues of LDL's apoprotein are acetylated, the LDL complex no longer binds to the LDL receptor, and instead can be taken up by endothelial cells and macrophages in a highly cell specific manner.

Amnion derived adherent cells were grown either in growth medium without VEGF, or in EGM2-MV (Cambrex) with VEGF, to evaluate the angiogenic potency of amnion derived adherent cells in general, as well as the effect of VEGF on the differentiation potential of amnion derived adherent cells. The cells were cultured in their respective media in 12-well plates for 4 to 7 days until they reached 70-80% confluence and subsequently were incubated with a 10 µg/mL acetylated LDL (Invitrogen) overnight. The cells were then counterstained with Calcein AM (Invitrogen) and evaluated for their acetylated LDL uptake using fluorescence microscopy. HUVECs as control cells for acetylated LDL uptake were grown in EGM2-MV and analyzed as described above. Amnion derived adherent cells displayed minimal uptake of acetylated LDL under normal growth conditions, but were induced/differentiated to increase their uptake through stimulation with VEGF. See FIG. 7.

6.3.4 Tube Formation for Evaluation of Angiogenic Potency of Amnion Derived Adherent Cells Amnion derived adherent cells were grown either in growth medium without VEGF or EGM2-MV with VEGF to evaluate the angiogenic potency of the cells in general, as well as the effect of VEGF on the differentiation potential of the cells. HUVECs, as control cells for tube formation, were grown in EGM2-MV. The cells were cultured in the respective media for 4 to 7 days until they reached 70-80% confluence. Cold (4° C.) MATRIGEL™ solution (50 µL; BD Biosciences) was dispensed into wells of a 12-well plate and the plate was incubated for 60 min at 37° C. to allow the solution to gel. The AMDACs and HUVEC cells were trypsinized, resuspended in the appropriate media (with and without VEGF) and 100 µl of diluted cells (1 to $3 \times 10^4$ cells) were added to each of the MATRIGEL™-containing wells. The cells on the polymerized MATRIGEL™, in the presence or absence of 0.5 to 100 ng VEGF, were placed for 4 to 24 hours in a 5% $CO_2$ incubator at 37° C. After incubation the cells were evaluated for signs of tube formation using standard light microscopy.

Amnion derived adherent cells displayed minimal tube formation in the absence of VEGF, but were induced/differentiated to form tube-like structures through stimulation with VEGF. See FIG. 8.

6.3.5 Hypoxia Responsiveness for Evaluation of Angiogenic Potency of Amnion Derived Adherent Cells To evaluate the angiogenic functionality of endothelial cells and/or endothelial progenitors, cells can be assessed in regard to their capability to secrete angiogenic growth factors under hypoxic and normoxic conditions. Culture under hypoxic conditions usually induces an increased secretion of angiogenic growth factors by either endothelial cells or endothelial progenitor cells, which can be measured in the conditioned media. Amnion derived adherent cells were plated at equal cell numbers in their standard growth medium and grown to approximately 70-80% confluence. Subsequently, the cells were switched to serum-free medium (EBM-2) and incubated under normoxic (21% $O_2$) or hypoxic (1% $O_2$) conditions for 48 h. The conditioned media were collected and the secretion of angiogenic growth factors was analyzed using commercially available ELISA kits from R&D Systems. The ELISA assays were performed according to manufacturer's instructions and the amount of the respective angiogenic growth factors (VEGF and IL-8) in the conditioned media was normalized to $1 \times 10^6$ cells.

Amnion derived adherent cells displayed elevated secretion of various angiogenic growth factors under hypoxic conditions. See FIG. 9.

In a separate experiment, AMDACs were plated at equal cell numbers in standard growth medium and grown to approximately 70-80% confluence. Subsequently, the cells were switched to serum-free medium (EBM-2) and incubated under normoxic (21% $O_2$) or hypoxic (1% $O_2$) conditions for 48 h. The cells were subjected to flowcytometric analyses for the cellular marker CD202b (also known as Tie2, Tek, or angiopoietin-1 receptor), a receptor involved in vascular development and angiogenesis. Conditioned media were collected, and the secretion of angiogenic growth factors was analyzed using commercially available ELISA kits (R&D Systems). Flow cytometric analyses were performed according as described above, and the ELISA assays were performed according to manufacturer's instructions. The amount of the respective angiogenic growth factors in the conditioned media was normalized to $1 \times 10^6$ cells. AMDACs displayed elevated expression of CD202b under hypoxic conditions, as compared to normoxic conditions. See FIG. 10.

6.3.6 Cardiomyogenic Differentiation for Evaluation of Angiogenic Potency of Amnion Derived Adherent Cells To induce the differentiation of progenitor cells towards a cardiomyocyte lineage, a combination of hanging drop culture (HD, to halt proliferation of the cells and start the differentiation process) with subsequent treatment of the growth-arrested cells with specific factors was performed in several stages. Following hanging drop culture, the cells were induced with combinations of activin A, bone morphogenetic protein 4 (BMP4), basic fibroblast growth factor (bFGF, also known as FGF2), vascular endothelial growth factor (VEGF, also known as VEGFA) and dickkopf homolog 1 (DKK1) over a period of 16 days. In brief, amnion derived adherent cells were grown to approximately 70% confluence in standard growth medium. The cells were then trypsinized, and washed in buffer as previously described. Drops of 20 µl containing 700 cells were suspended in the relevant medium and placed on the inner side of the lid of a 100 mm Petri dish using a multi-channel pipette. The lid was carefully inverted and placed on the top of the dish, which contained 25 mL of sterile PBS to keep the drops from drying out. The hanging drop cultures were incubated for 48 h at 37° C. in a 5% $CO_2$ incubator. Subsequently, the aggregate bodies of the cells were re-seeded into culture plates coated with 0.1% gelatin containing lineage specific differentiation medium for further induction.

Stimulation steps proceeded as follows: Stage 1, 4 days BMP4 (0.5 ng/mL); Stage 2, 5 days BMP4 (10 ng/mL), bFGF (5 ng/mL), Activin A (3 ng/mL); Stage 3, 3 days VEGF (10 ng/mL), DKK1 (150 ng/mL); Stage 4, 4 days VEGF (10 ng/mL), DKK1 (150 ng/mL), bFGF (5 g/mL) (+/−5-10 nM 5-aza-cytidine). Subsequently, total RNA of the treated cells was prepared and qRT-PCR analyses for cardiomyogenic markers were performed as previously described.

The results showed that amnion derived adherent cells can be induced/differentiated to express various cardiomyocytic markers. See FIG. 11.

6.3.7 HUVEC Response to AMDAC-Conditioned Medium

AMDACs were cultured for 48 hours in growth medium containing 60% DMEM-LG (Gibco); 40% MCBD-201 (Sigma); 2% FBS (Hyclone Labs), 1× insulin-transferrin-selenium (ITS); 10 ng/mL linoleic acid-bovine serum albumin (LA-BSA); 1 n-dexamethasone (Sigma); 100 µM ascorbic acid 2-phosphate (Sigma); 10 ng/mL epidermal growth factor (R & D Systems); and 10 ng/mL platelet-derived growth factor (PDGF-BB) (R & D Systems), and then cultured for an additional 48 hrs in serum-free media. Conditioned medium from AMDAC culture was collected and used to stimulate serum-starved HUVECs for 5, 15, and 30 minutes. The HUVECs were subsequently lysed and stained with a BD™ CBA (Cytometric Bead Assay) Cell Signaling Flex Kit (BD Biosciences) for phosphoproteins known to play a role in angiogenic pathway signaling. AMDACs were found to be strong activators of AKT-1 (which inhibits apoptotic processes), AKT-2 (which is an important signaling protein in the insulin signaling pathway, and ERK 1/2 cell proliferation pathways in HUVECs. These results further demonstrate the angiogenic capability of AMDACs.

6.4 Example 4

Induction of Angiogenesis by AMDACs

This Example demonstrates that AMDACs promote angiogenesis in an in vivo assay using chick chorioallantoic membrane (CAM).

Two separate CAM assays were conducted. In the first CAM assay, intact cell pellets from different preparations of AMDACs were evaluated. In the second CAM assay, supernatants of different AMDACs preparations were evaluated. Fibroblast growth factor (bFGF) was used as a positive control, and MDA-MB-231 human breast cancer cells as a reference (negative control). The endpoint of the study was to determine the blood vessel densities of all treatment and control groups.

6.4.1 CAM Assay Using Cells

Three AMDACs cell preparations, referred to herein at Lot 1, Lot 2 and Lot 3, prepared as described above and cryopreserved, were used. AMDACs were thawed for dosing and the number of cells dosed on the CAM was determined.

Study Design: The study included 7 groups with 10 embryos in each group. The design of the study is described in Table 6.

TABLE 6

Study groups, chick chorioallantoic membrane angiogenesis assay.

| Group No. | # of Embryos | Treatment | End Point |
|---|---|---|---|
| 1 | 10 | Vehicle control (40 µl of PBS/ MATRIGEL ™ mixture, 1:1 by volume) | Blood vessel density score |
| 2 | 10 | Positive control, treated with bFGF (100 ng/CAM in 40 µl of DMEM/ MATRIGEL ™ mixture, 1:1) | Same as group 1 |
| 3 | 10 | Medium control (40 µl of DMEM) | Same as group 1 |
| 4 | 10 | AMDACS, Lot 1 | Same as group 1 |
| 5 | 10 | AMDACS, Lot 2 | Same as group 1 |
| 6 | 10 | AMDACS, Lot 3 | Same as group 1 |
| 7 | 10 | MDA-MB-231 cells P34, Lot No. 092608 | Same as group 1 |

CAM Assay Procedure: Fresh fertile eggs were incubated for 3 days in a standard egg incubator at 37° C. for 3 days. On Day 3, eggs were cracked under sterile conditions and embryos were placed into twenty 100 mm plastic plates and cultivated at 37° C. in an embryo incubator with a water reservoir on the bottom shelf. Air was continuously bubbled into the water reservoir using a small pump so that the humidity in the incubator was kept constant. On Day 6, a sterile silicon "O" ring was placed on each CAM, and then AMDACs at a density of $7.69 \times 10^5$ cells/40 µL of medium/ MATRIGEL™ mixture (1:1) were delivered into each "O" ring in a sterile hood. Tables 2A and 2B represent the number of cells used and the amount of medium added to each cell preparation for dosing. Vehicle control embryos received 40 µL of vehicle (PBS/MATRIGEL™, 1:1), positive controls received 100 ng/ml bFGF in 40 µl of DMEM medium/ MATRIGEL™ mixture (1:1), and medium controls received 40 µl of DMEM medium alone. Embryos were returned to the incubator after each dosing was completed. On Day 8, embryos were removed from the incubator and kept at room temperature while blood vessel density was determined under each "O" ring using an image capturing system at a magnification of 100×.

Blood vessel density was measured by an angiogenesis scoring system that used arithmetic numbers 0 to 5, or exponential numbers 1 to 32, to indicate the number of blood vessels present at the treatment sites on the CAM. Higher scoring numbers represented higher vessel density, while 0 represented no angiogenesis. The percent of inhibition at each dosing site was calculated using the score recorded for that site divided by the mean score obtained from control samples for each individual experiment. The percent of inhibition for each dose of a given compound was calculated by pooling all results obtained for that dose from 8-10 embryos.

TABLE 7

Amount of medium added to each cell preparation for normalization of the final cell suspension for dosing

| Cell Line | Pellet size | Normalization with DMEM and MATRIGEL ™ | Final Volume of Cell Suspension |
|---|---|---|---|
| AMDACs Lot 1 | 260 µL | 0 µL + 260 µL MATRIGEL ™ | 520 µL |
| AMDACs Lot 2 | 170 µL | 90 µL + 260 µL MATRIGEL ™ | 520 µL |
| AMDACs Lot 3 | 170 µL | 90 µL + 260 µL MATRIGEL ™ | 520 µL |
| MDA-MB-231 | 40 µL | 220 µL + 260 µL MATRIGEL ™ | 520 µL |

Results

The results of blood vessel density scores are presented in FIG. 12. The results clearly indicate that the blood vessel density scores of chick chorioallantoic membranes treated with each of the stem cell suspensions, or 100 ng/mL of bFGF, or MDAMB231 breast cancer cell suspensions were statistically significantly higher compared to those of the vehicle control CAMs (P<0.001, Student's "t" test). The medium used for culturing the stem cells did not have any effect on the blood vessel density. Further, the induction of blood vessel density of AMDACs preparations showed some variation, but the variations were not statistically significant. This concludes that the induction potency of each of the 5 stem cell preparations was approximately the same.

6.4.2 CAM Assay Using AMDACs Cell Supernatants

Supernatant samples from MDA-MB-231 cells and from each of the different stem cell preparations described in the AMDACs CAM assay above were used in a second CAM assay. As with the AMDACs CAM assay, bFGF and MDA-MB-231 cells were used as positive controls.

Study Design: The study included 7 groups with 10 embryos in each group. The design of the study is described in Table 8.

TABLE 8

Study Design - CAM assay using cell supernatants

| Group No. | # of Embryos | Treatment | End Point |
|---|---|---|---|
| 1 | 10 | Vehicle control (40 µl of PBS/MATRIGEL ™ mixture, 1:1 by volume) | Blood vessel density score |
| 2 | 10 | Positive control, treated with bFGF (100 ng/CAM in 40 µl of DMEM/MATRIGEL ™ mixture, 1:1) | Same as group 1 |
| 3 | 10 | Medium control (40 µl of DMEM) | Same as group 1 |
| 4 | 10 | Supernatant of AMDACs Lot 1 | Same as group 1 |
| 5 | 10 | Supernatant of AMDACs Lot 2 | Same as group 1 |
| 6 | 10 | Supernatant of AMDACs Lot 3 | Same as group 1 |
| 7 | 10 | Supernatant of MDAMB231 cells (P34) | Same as group 1 |

AMDACs cells were used as Passage 6.

CAM Assay Procedure: The assay procedure was the same as described above in the AMDACs CAM assay. The only difference was that supernatant from each stem cell preparation or from MDA-MB-231 cells was used as test material. For dosing, each supernatant was mixed with MATRIGEL™ (1:1 by volume) and 40 µL of the mixture was dosed to each embryo.

Results

Blood vessel density scores (see FIG. 13) indicate that the induction of blood vessel formation by the supernatant of each stem cell preparation differed. Supernatant samples from the three lots of AMDACs showed significant effect on blood vessel induction with P<0.01, P<0.001, and P<0.02 (Student's "t" test) respectively. As expected, positive control bFGF also showed potent induction of blood vessel formation as seen above in CAM assay no. 1 (P<0.001, Student's "t" test). However, supernatant from MDA-MB-231 human breast cancer cells did not show significant induction on blood vessel formation compared to the vehicle controls. As previously shown, culture medium alone did not have any effect.

6.5 Example 5

AMDACs Exhibit Neuroprotective Effect

This Example demonstrates that AMDACs have a neuroprotective effect in low-oxygen and low-glucose conditions using an oxygen-glucose deprivation (OGD) insult assay, and reduce reactive oxygen species. As such, these results indicate that AMDACs would be useful in treating ischemic conditions such as stroke or peripheral vascular disease, and would protect against reperfusion injuries resulting from ischemic conditions.

Human neurons (ScienCell, catalog #1520) were cultured as per manufacturer's recommendations. Briefly, culture vessels were coated with Poly-L-Lysine (2 µg/mL) in sterile distilled water for 1 hour at 37° C. The vessel was washed with double distilled $H_2O$ three times. Neuron Medium (ScienCell) was added to vessel and equilibrated to 37° C. in an incubator. Neurons were thawed, and added directly into the vessels without centrifugation. During subsequent culture, medium was changed the day following culture initiation, and every other day thereafter. The neurons were typically ready for insult by day 4.

OGD medium (Dulbecco's Modified Eagle's Medium-Glucose Free) was prepared by first warming the medium in a water bath, in part to reduce the solubility of oxygen in the liquid medium. 100% nitrogen was bubbled for 30 minutes through the medium using a 0.5 µm diffusing stone to remove dissolved oxygen. HEPES buffer was added to a final concentration of 1 mM. Medium was added directly to the neurons at the end of the sparge. A small sample of the medium was aliquoted for confirmation of oxygen levels using a dip-type oxygen sensor. Oxygen levels were typically reduced to 0.9% to about 5.0% oxygen.

A hypoxia chamber was prepared by placing the chamber in an incubator at 37° C. for at least 4 hours (overnight preferred) prior to gassing. Medium in the culture vessels was removed and replaced with de-gassed medium, and the culture vessels were placed in the hypoxia chamber. The hypoxia chamber was then flushed with 95% $N_2$/5% $CO_2$ gas through the system at a rate of 20-25 Lpm for at least 5 minutes. The system was incubated in the incubator at 37° C. for 4 hours, with degassing of the chamber once more after 1 hour.

At the conclusion of the insult procedure, OGD medium was aspirated and warm medium was added to the neurons. 24-28 hours later, AMDACs and neurons were plated at equal numbers at 100,000 cells each per well of a 6-well plate suspended in Neuronal Medium were added to the neurons and co-cultured for 6 days.

Photomicrographs were taken of random fields in a 6-well plate for each condition. Cells having a typical neuron morphology were identified, and neurite lengths were recorded. The average length of the neurites positively correlated to neuronal health, and were longer in co-cultures of neurons and AMDACs, indicating that the AMDACs were protecting the cells from the insult.

Reactive Oxygen Species Assay

AMDACs were determined to express superoxide dismutase, catalase, and heme oxygenase gene during hypoxia. The ability of AMDACs to scavenge reactive oxygen species, and to protect cells from such species, was determined in an assay using hydrogen peroxide as a reactive oxygen species generator.

Assay Description: Target cells (Astrocytes, ScienCell Research Laboratories) were seeded in 96-well black well plates pre-coated with poly-L-lysine at 6000/cm². The astrocytes are allowed to attach overnight in growth medium at 37° C. with 5% carbon dioxide. The following day, the culture media was removed and the cells were incubated with cell permeable dye DCFH-DA (Dichlorofluorescin diacetate), which is a fluorogenic probe. Excess dye was removed by washing with Dulbecco's Phosphate Buffered Saline or Hank's Buffered Salt Solution. The cells were then insulted with reactive oxygen species by addition of 1000 µM hydrogen peroxide for 30-60 minutes. The hydrogen peroxide-containing medium was then removed, and replaced with serum-free, glucose-free growth medium. AMDACs (either cells designated as Lot 1 or Lot 2), or BM-MSCs, were added at 6000/cm$^2$, and the cells were cultured for another 24 hours. The cells were then read in a standard fluorescence plate reader at 480Ex and 530Em. The reactive oxygen species content of the medium was directly proportional to the levels of DCFH-DA in the cell cytosol. The reactive oxygen species content was measured by comparison to pre-determined DCF standard curve. All experiments were done with N=24.

For the assay, 1×DCFH-DA was prepared immediately prior to use by diluting a 20×DCFH-DA stock solution to 1× in cell culture media without fetal bovine serum, and stirring to homogeneity. Hydrogen Peroxide ($H_2O_2$) dilutions were prepared in DMEM or DPBS as necessary. A standard curve was prepared as a 1:10 dilution series in concentration range 0 µM to 10 µM by diluting 1 mM DCF standard in cell culture media, transferring 100 µl of DCF standard to a 96 well plate suitable for fluorescent measurement, and adding 100 µl of cell lyses buffer. Fluorescence was read at 480Ex and 530Em.

Results: Both lots of AMDACs used significantly reduced the concentration of reactive oxygen species in the astrocyte co-cultures. See FIGS. 14A and 14B. In contrast, BM-MSCs failed to significantly reduce reactive oxygen species in the astrocyte co-cultures.

6.6 Methods of Treatment Using Amnion Derived Adherent Cells

6.6.1 Treatment of Myocardial Infarction

A male individual in his middle '50s presents with chest pain radiating to the left arm for more than 20 minutes, shortness of breath, nausea, palpitations, sweating. With electrocardiogram results and a rise and fall of blood levels of creatine kinase, a differential diagnosis of myocardial infarction (transmural) of the anterior wall of the heart is made. After stabilization of the individual with nitroglycerin and streptokinase, the individual is administered $1\times10^8$ to $5\times10^8$ AMDACs in 0.9% saline directly to the affected area using a cardiac syringe with local anesthetic. The individual is monitored on an emergency basis for the next 72 hours. The individual is further monitored over the next three months port-treatment by electrocardiogram and/or dye visualization techniques to assess the extent of revascularization of the infarcted area. Therapeutic effectiveness is established if electrocardiogram results are discernably closer to normal than before administration of the AMDACs, or if the infarcted area, as visualized, is discernably revascularized.

6.6.2 Treatment of Cardiomyopathy

An individual presents with breathlessness, swelling of the legs and ankles, and irregular heartbeats. After excluding other causes, and with a confirmatory electrocardiogram, a diagnosis of cardiomyopathy is made. A sonogram confirms that the individual has congestive cardiomyopathy. The individual is administered $1\times10^8$ to $5\times10^8$ AMDACs in 0.9% saline directly to the cardiac artery using a cardiac syringe with local anesthetic. The individual is monitored over the next three months for changes in sonogram readings indicating more normal blood flow, and for improvement in sensation of breathlessness and reduction in swelling of the legs and ankles. Therapeutic effectiveness is established for the individual if any of these sings show improvement during the monitoring period.

6.6.3 Treatment of Peripheral Vascular Disease

An individual presents with cold, tingling feet that turn red upon dangling, and pain, weakness and tiredness in the legs. After excluding diabetes, a diagnosis of peripheral artery disease is made. The individual is administered individual is administered $1\times10^9$ to $5\times10^9$ AMDACs intravenously in 450 mL 0.9% saline, and is monitored biweekly for the next three months. Therapeutic effectiveness is established if any of the symptoms described above improve during the monitoring period.

6.6.4 Treatment of Peripheral Vascular Disease

An individual presents with cold, tingling feet that turn red upon dangling, and pain, weakness and tiredness in the legs. After excluding diabetes, a diagnosis of peripheral artery disease is made. The individual is administered individual is administered $1\times10^8$ to $5\times10^8$ AMDACs intramuscularly in 5 mL 0.9% saline, and/or an equivalent amount intravenously or intraarterially, locally between the digits of the foot, and is monitored biweekly for the next three months. Therapeutic effectiveness is established if any of the symptoms described above improve during the monitoring period.

6.6.5 Combination Treatment of Peripheral Vascular Disease

An individual presents with cold, tingling feet that turn red upon dangling, and pain, weakness and tiredness in the legs. After excluding diabetes, a diagnosis of peripheral artery disease is made. The individual is administered individual is administered $1\times10^9$ to $5\times10^9$ AMDACs intravenously in 450 mL 0.9% saline, and is monitored biweekly for the next three months. The individual is also prescribed Cilostazol, 100 mg, to be taken twice daily. Therapeutic effectiveness is established if any of the symptoms described above improve during the monitoring period.

6.6.6 Combination Therapy of Peripheral Vascular Disease

An individual presents with a cold, tingling right foot that turns red upon dangling, and pain, weakness and tiredness in the right leg. After excluding diabetes, a diagnosis of peripheral artery disease is made. The individual is administered individual undergoes angioplasty, and surgery to implant a stent in the femoral artery. The individual is subsequently administered $1\times10^9$ to $5\times10^9$ AMDACs intravenously in 450 mL 0.9% saline, and is monitored biweekly for the next three months. Therapeutic effectiveness is established if any of the symptoms described above improve during the monitoring period.

6.6.7 Treatment of Stroke Using AMDACs

A 52 year old male presents with hemiplegia on the left side of the body, and partial aphasia. A diagnosis of ischemic stoke is made. After locating the area of ischemia using magnetic resonance imaging, the individual is prepared for surgery to create an opening in the skull on the affected side. Once the opening is made, $5\times10^7$ to $1\times10^8$ AMDACs in 1-2 mL 0/9% saline solution are administered to the ischemic area. The individual is monitored over the next 7-14 days for signs of improvement in any symptom of the stroke, particularly hemiplegia or aphasia. Therapeutic effectiveness is established if any of the symptoms described above improve during the monitoring period.

6.6.8 Treatment of Stroke Using AMDACs

A 52 year old male presents with hemiplegia on the left side of the body, and partial aphasia. A diagnosis of ischemic stoke is made. After locating the area of ischemia using magnetic resonance imaging, the individual is prepared for surgery to create an opening in the skull on the affected side. Once the opening is made, $1\times10^9$ to $5\times10^9$ AMDACs in 450 mL 0/9% saline solution are administered intravenously. The individual is monitored over the next 7-14 days for signs of improvement in any symptom of the stroke, particularly hemiplegia or aphasia. Therapeutic effectiveness is established if any of the symptoms described above improve during the monitoring period.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method of treating an individual having a disruption of blood flow in or around a limb comprising administering to said individual a population of cells, wherein at least 50% of the cells in said population are human amnion derived adherent cells, wherein said amnion derived adherent cells are adherent to tissue culture plastic, and wherein said amnion derived adherent cells are OCT-4- as determinable by RT-PCR, and CD49f+, CD90+, and HLA-G- as determinable by flow cytometry, wherein said cells promote angiogenesis and blood flow is improved in or around said limb.

2. The method of claim 1, wherein at least 70%, 80%, 90%, 95%, or 99% of the cells in said population are said amnion derived adherent cells.

3. The method of claim 1, wherein said population of cells 4 is formulated in a hydrogel solution.

4. The method of claim 1, wherein said disruption of blood flow in or around a limb is peripheral arterial disease.

5. The method of claim 1, wherein said disruption of blood flow in or around a limb is critical limb ischemia.

6. The method of claim 1, wherein at least 70% of the cells in said population are said amnion derived adherent cells.

7. The method of claim 1, wherein at least 80% of the cells in said population are said amnion derived adherent cells.

8. The method of claim 1, wherein at least 90% of the cells in said population are said amnion derived adherent cells.

9. The method of claim 1, wherein at least 95% of the cells in said population are said amnion derived adherent cells.

10. The method of claim 1, wherein at least 99% of the cells in said population are said amnion derived adherent cells.

11. The method of claim 4, wherein at least 70% of the cells in said population are said amnion derived adherent cells.

12. The method of claim 4, wherein at least 80% of the cells in said population are said amnion derived adherent cells.

13. The method of claim 4, wherein at least 90% of the cells in said population are said amnion derived adherent cells.

14. The method of claim 4, wherein at least 95% of the cells in said population are said amnion derived adherent cells.

15. The method of claim 4, wherein at least 99% of the cells in said population are said amnion derived adherent cells.

16. The method of claim 5, wherein at least 70% of the cells in said population are said amnion derived adherent cells.

17. The method of claim 5, wherein at least 80% of the cells in said population are said amnion derived adherent cells.

18. The method of claim 5, wherein at least 90% of the cells in said population are said amnion derived adherent cells.

19. The method of claim 5, wherein at least 95% of the cells in said population are said amnion derived adherent cells.

20. The method of claim 5, wherein at least 99% of the cells in said population are said amnion derived adherent cells.

* * * * *